United States Patent
Zender et al.

(10) Patent No.: US 10,441,577 B2
(45) Date of Patent: Oct. 15, 2019

(54) MEDICAMENT FOR TREATMENT OF LIVER CANCER

(75) Inventors: Lars Zender, Braunschweig (DE); Ramona Rudalska, Braunschweig (DE); Daniel Dauch, Braunschweig (DE)

(73) Assignee: HELMHOLTZ ZENTRUM FUER INFEKTIONSFORSCHUNG, Braunschweig (DE)

(*) Notice: Subject to any disclaimer, the term of this patent is extended or adjusted under 35 U.S.C. 154(b) by 256 days.

(21) Appl. No.: 14/131,059

(22) PCT Filed: Jul. 9, 2012

(86) PCT No.: PCT/EP2012/063445
§ 371 (c)(1),
(2), (4) Date: Apr. 10, 2014

(87) PCT Pub. No.: WO2013/007708
PCT Pub. Date: Jan. 17, 2013

(65) Prior Publication Data
US 2015/0079154 A1     Mar. 19, 2015

Related U.S. Application Data

(60) Provisional application No. 61/508,368, filed on Jul. 15, 2011.

(30) Foreign Application Priority Data

| Jul. 8, 2011 | (EP) | 11173379 |
| Mar. 23, 2012 | (EP) | 12161141 |
| Apr. 2, 2012 | (EP) | 12162905 |

(51) Int. Cl.
| A61K 31/4412 | (2006.01) |
| A61K 31/4439 | (2006.01) |
| A61K 31/513 | (2006.01) |
| A61K 31/5513 | (2006.01) |
| A61K 31/5377 | (2006.01) |
| A61K 31/519 | (2006.01) |
| A61K 38/08 | (2019.01) |
| A61K 31/713 | (2006.01) |
| A61K 31/444 | (2006.01) |
| A61K 45/06 | (2006.01) |
| A61K 31/44 | (2006.01) |

(52) U.S. Cl.
CPC .......... *A61K 31/4412* (2013.01); *A61K 31/44* (2013.01); *A61K 31/444* (2013.01); *A61K 31/4439* (2013.01); *A61K 31/513* (2013.01); *A61K 31/519* (2013.01); *A61K 31/5377* (2013.01); *A61K 31/5513* (2013.01); *A61K 31/713* (2013.01); *A61K 38/08* (2013.01); *A61K 45/06* (2013.01)

(58) Field of Classification Search
None
See application file for complete search history.

(56) References Cited

U.S. PATENT DOCUMENTS

2012/0108641 A1   5/2012  Demers et al.
2012/0115862 A1*  5/2012  Laufer et al. ............. 514/232.8

FOREIGN PATENT DOCUMENTS

| CN | 101 317 832 | 8/2011 |
| WO | WO 2000/042012 | 7/2000 |
| WO | WO 2005/009961 | 2/2005 |
| WO | WO 2010/128259 | 11/2010 |

OTHER PUBLICATIONS

Abou-Alfa et al. (JCO Sep. 10, 2006 vol. 24 No. 26 4293-4300).*
Balkwill (Cancer and Metastasis Reviews Sep. 2006, vol. 25, Issue 3, pp. 409-416).*
Wagner et al. (Nature Reviews Cancer vol. 9 Aug. 2009 p. 537-549).*
Liu Cancer Res 2006; 66: (24). Dec. 15, 2006, (Year: 2006).*
Huynh, Hung, "Molecularly targeted therapy in hepatocellular carcinoma", *Biochemical Pharmacology*, 80 (2010) pp. 550-560.
Llovel, J. et al., "6519 Efficacy and safety of sorafenib in patients with advanced hepatocellular carcinoma (HCC): collective results from the phase III sorafenib HCC assessment randomized protocol (SHARP) and Asia-Pacific trials", Joint ECCO 15—34th ESMO Multidisciplinary Congress, Sep. 2009, vol. 7, No. 2, p. 367.
Min, Lihua, et al., "Mitogen-activated protein kinases in hepatocelluclar carcinoma development", *Seminars in Cancer Biology*, 21, (2011) pp. 10-20.
Noel, J. Kay, et al., "Systematic review to establish the safety profiles for direct and indirect inhibitors of p38 Mitogen-activated protein kinases for treatment of cancer", *Med Oncol*, (2008) 25, pp. 323-330.
Parekh, Palak, et al., "Downregulation of cyclin D1 is associated with decreased levels of p38 MAP kinases, Akt/PKB and Pak1 during chemopreventive effects of resveratrol in liver cancer cells", *Experimental and Toxicological Pathology*, 63 (2011) pp. 167-173.
Unknown: "Nexavar: EPAR—all authorized publications", Internet Mar. 4, 2007, Retrieved from the Internet: http://www.ema.europa.eu/docs/en_GB/document_library/EPAR—All Authorised_presentations/human/000690/WC500027706.pdf [retrieved on Nov. 24, 2011] (1 page).
Hui et al, 2007, Cell Cycle 6:20, pp. 2429-2433.
Stepniak et al, 2006, Genes & Development, 20:2306-2314.

* cited by examiner

*Primary Examiner* — Jeffrey S Lundgren
*Assistant Examiner* — William Y Lee
(74) *Attorney, Agent, or Firm* — Dvorah Graeser; Graeser Associates International Inc

(57) ABSTRACT

The invention provides a pharmaceutical composition comprising Sorafenib in combination with an inhibitor of a specific kinase inhibitor as a medicament for the treatment or prevention of liver cancer.

Figure 1:
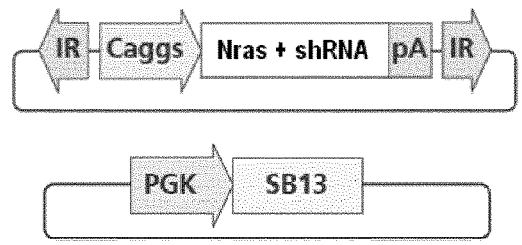

7 Claims, 8 Drawing Sheets
Specification includes a Sequence Listing.

MEDICAMENT FOR TREATMENT OF LIVER CANCER

The present invention relates to a medicament and to a pharmaceutical composition, respectively, which is suitable for the treatment or prevention of liver cancer, especially hepatocellular carcinoma (HCC) in human patients.

Further, the invention relates to a method for the treatment of liver cancer by administration of the pharmaceutical composition to a patient, and to a process for producing a medicament or pharmaceutical composition, respectively, which is suitable for the treatment of liver cancer.

STATE OF THE ART

Today, the only curative options for the treatment of liver cancer are surgical resection or liver transplantation. However, at the time of diagnosis the majority of patients present with advanced tumor growth and are therefore not eligible for these treatment options. Liver cancer is a primarily chemoresistant tumor and only recently Llovet and coworkers described the multikinase inhibitor Sorafenib as the first systemic treatment which can prolong survival of patients with HCC. However, the treatment is costly and only yields a survival advantage of less than three month. Therefore, there is an urgent clinical need for the development of medicaments which increase efficiency over Sorafenib.

WO 2010/128259 A1 describes a pharmaceutical combination of Sorfenib with a vascular disrupting agent.

WO2005/009961 A2 describes a fluoro derivative of Sorafenib.

Huynh et al, Biochemical Pharmacology, 550-560 (2010), describe Sorafenib for use as a medicament in the treatment of liver cancer.

Noel et al, Med Oncol 323-330 (2008) report on studies on cancer treatment using Sorafenib or Thalidomid (Contergan).

Parekh et al, Experimental and Toxicologic Pathology 167-173 (2011) describe that resveratrol treatment down-regulated cyclin D1 and p38 MAP kinase, Akt and Pak1 expression and activity in HepG2 cells, and that resveratrol treated cells showed an increase in ERK activity.

Min et al, Seminars in Cancer Biology, 10-20 (2011), quote that p38α has a negative regulatory role in tumorigenesis, especially of the liver, and that the p38α signalling pathway has a suppressive role in tumorigenesis. Sorafenib is described to inhibit proliferation of HCC cells and to induce apoptosis by inhibiting the phosphorylation of MEK, ERK and down-regulating cyclin D1 levels.

OBJECTS OF THE INVENTION

It is an object of the invention to provide a pharmaceutical composition for the treatment of liver cancer with an increased efficacy. It is a preferred object of the invention to provide for a pharmaceutical composition for use against liver cancer, the composition having an increased efficacy in comparison to a composition containing the same amount of Sorafenib.

GENERAL DESCRIPTION OF THE INVENTION

The invention achieves these objects by the features as defined by the claims, especially by providing a pharmaceutical composition, the composition comprising Sorafenib and, in addition to Sorafenib, an inhibitor of Mapk14 (p38α kinase inhibitor) as a medicament for use in the treatment and/or in the prevention of cancer, especially liver cancer. The inhibitor of Mapk14 activity is a pharmaceutical active agent which in combination with Sorafenib is used as a medicament for the treatment and/or prevention of liver cancer. In the combination, Sorafenib and the inhibitor of Mapk14 can be provided for joint administration, e.g. as a composition containing both Sorafenib and an inhibitor of Mapk14, or Sorafenib and the inhibitor of Mapk14 can be provided for separate administration, e.g. firstly Sorafenib and secondly an inhibitor of Mapk14, or firstly an inhibitor of Mapk14 and secondly Sorafenib. Accordingly, the invention provides a combination of Sorafenib with an inhibitor of Mapk14 as a medicament for the treatment and/or prevention of liver cancer for joint or separate administration, as well as for a composition comprising a combination of Sorafenib and of an inhibitor of Mapk14, e.g. each of Sorafenib and an inhibitor of the activity of Mapk14 contained in a separate formulation for use in separate administration, or a formulation containing both Sorafenib and an inhibitor of the activity of Mapk14 in combination. Further, the invention relates to the treatment of cancer, especially of liver cancer, by administration of this pharmaceutical composition, e.g by separate or simultaneous administration of Sorafenib and of the inhibitor of Mapk14 to a human suffering from cancer, especially from liver cancer. Optionally, the liver cancer is non-viral liver cancer or virally caused liver cancer.

It has been demonstrated during the preparation of the invention that an agent which inhibits the activity of Mapk14 increases the efficacy of Sorafenib, as a medicament in the treatment or prevention of liver cancer. As the inhibition of the activity of Mapk14 can be obtained by the inhibition of the expression of Mapk14 gene product or protein, inhibitors of the translation of the mRNA encoding Mapk14, and inhibitors of Mapk14 protein activity, e.g. kinase inhibitors, are comprised in the group of inhibitors of the activity of Mapk14 which are used in a combination with Sorafenib for use as a medicament for the treatment or prevention of liver cancer.

Inhibitors of the activity of Mapk14, especially of the expression of Mapk14, are comprised in the group of small regulatory RNAs such as small inhibitory RNAs (siRNA), short hairpin RNA (shRNA) and microRNAs (miRNA), having a nucleic acid sequence hybridizing under physiological conditions, e.g. within a liver cell, to the mRNA encoding Mapk14 to reduce or inhibit the presence of Mapk14 in a hepatocyte or a liver cancer cell through RNA interference and accordingly inhibit the activity of Mapk14. Small regulatory RNA molecules comprise or consist of the group containing at least one of the following inhibitory RNAs: SEQ ID NO: 1 to SEQ ID NO: 1364.

ShRNA molecules, e.g. contained in microRNA molecules, hybridize to the mRNA encoding Mapk14. The Mapk14 encoding gene gives rise to four mRNAs, which are regarded as splice products. The splice product mRNAs are given as SEQ ID NO: 1365 to SEQ ID NO: 1368. The shRNA of the invention through RNA interference reduce the expression, and hence the activity of Mapk14 gene product. Alternatively, the inhibitory RNAs can be contained in classical antisense oligonucleotides for targeting the same mRNA regions for suppression of Mapk14 expression.

The specificity of shRNA, especially when the sequence encoding the shRNA was contained in a microRNA can also be shown in an vitro test using the reduction of the expression of a reporter gene product from a fusion gene, which produces a fusion mRNA that contains the coding sequence for both the reporter gene and for Mapk14. In this assay, it can be found that the mRNA of the fusion gene, which mRNA comprises the coding sequence for Mapk14 in combination with the coding sequence for the reporter gene, is reduced in the presence of an shRNA which is specific for the mRNA encoding Mapk14, whereas a control encoding an mRNA of the reporter gene only did not show a reduction of the reporter gene expression in the presence of an shRNA hybridizing to the mRNA encoding Mapk14.

The inactivation of Mapk14 by inhibiting or reducing the expression of Mapk14 in hepatocytes or liver cancer cells in experimental animals, both by suppression of the expression of Mapk14 via continuous expression of an shRNA specific for the mRNA encoding Mapk14 in the mouse model, and by administration of a pharmaceutical composition, in which the pharmaceutical active agent consists of an shRNA specific for the mRNA encoding Mapk14 of the mouse reduces the present liver cancer or prevents the generation of liver cancer upon administration of agents which in the absence of the combination of a Mapk14 inhibitor and Sorafenib would induce a liver cancer.

The reduction or repression of Mapk14 activity by reducing or suppressing the expression of Mapk14 using the continuous expression of an shRNA which is specifically directed against the mRNA encoding Mapk14, or by administration of a pharmaceutical composition containing as the active ingredient or agent an shRNA specifically directed against the mRNA encoding Mapk14 in the animal model reduces a previously established liver cancer with increased efficacy upon administration of Sorafenib in comparison to the treatment with Sorafenib as the only pharmaceutical active agent, i.e. Sorafenib without the combination with an agent reducing Mapk14 activity.

In a preferred embodiment, the inhibitor of the activity of Mapk14 is at least one of the group comprising or consisting of inhibitors which have preference or specificity for inactivating the Mapk14 gene product, which compounds are given in the following table 1. Generally, an inhibitor of Mapk14 according to the invention has an IC50 of at maximum 30 nM, preferably of at maximum 20 nM, more preferably of at maximum 10 nM or max. 5 nM or of at maximum 1 nM, most preferably of at maximum 0.1 or of at maximum 0.01 nM. Preferably, the IC50 is determined in an in vitro assay on Mapk14, e.g. determining the IC50 (inhibitory concentration for 50% inhibition) in dependence on the concentration of the inhibitor. For example, Mapk14, preferably having the human amino acid sequence and human structure, e.g. produced by expression of the human gene encoding Mapk14 in a human cell line, is isolated and incubated in a suitable buffer in the presence of a substrate to be phosphorylated, e.g. ATF-2, MAPKAPK-2 or Hsp27, $^{32}$P-γ-labelled ATP and the inhibitor. The $^{32}$P-γ-labelled ATP is separated from the substrate, and the amount of $^{32}$P-phosphorylation is determined, e.g. using scintillation counting. The preferred substrate are ATF-2, MAPKAPK-2 or Hsp27 and a preferred buffer is: 20 mM HEPES (pH 7.5), 10 mM $MgCl_2$, 1 mg/ml BSA and protease inhibitor e.g. Complete mini (Roche), using incubation at room temperature or 37° C. For comparison, the inhibitor of Mapk14 has a lower IC50 than Sorafenib, which has an IC50 for Mapk14 of approx. 38 nM.

Additionally or alternatively, the inhibitory activity of the inhibitor of Mapk14 is determined in a cell-based in vitro assay using e.g. cancer cells, e.g. Hep3B. In the assay, the inhibitory activity of p38 inhibitors is determined for substrate protein of Mapk14 in relation to a housekeeping gene, e.g. α-tubulin. In the assay, cells are incubated with various concentrations of the inhibitor or carrier only respectively, e.g. for 2-4 days, and protein is extracted, e.g. using NP40-containing buffer. In the extracted protein, phosphorylated substrate protein of Mapk14 is determined, e.g. by immunological detection of phosphorylated substrate protein, e.g. using a Western blot of SDS-PAGE separated cellular protein. For immunological detection, a phospho-specific antibody can be used. A preferred substrate protein is ATF-2, MAPKAPK-2 and/or Hsp27.

Additionally or alternatively, the combination of Sorafenib with the additional inhibitor of Mapk14 of the invention in a cell-based assay has a significant higher toxicity or inhibition of proliferation rate against cultivated cancer cells, especially against liver cancer cells, e.g. against Hep3B. In the assay, cultivated living cells are counted following incubation with a combination of Sorafenib and the inhibitor of Mapk14 or with the same concentration of Sorafenib or inhibitor against Mapk14 alone or carriers, respectively, e.g. at concentrations of at maximum 20 μM, preferably at maximum 12 μm, more preferably at max. 5 μm. Significance can be determined using the two-tailed student's T-test. Preferably, the combination of Sorafenib and the inhibitor of Mapk14 according to the invention reduce cell proliferation of has an inhibitory effect on the cultivated cancer cells higher by at least a factor of 2, preferably at least by a factor of 4, more preferably at least by a factor of 10, in comparison to Sorafenib of the same concentration by itself.

TABLE 1

Inhibitors of Mapk14 activity

| name | Chemical name or structure |
| --- | --- |
| SB 203580 | 4-[5-(4-fluorophenyl)-2-[4-(methylsulfonyl)phenyl]-1H-imidazol-4-yl]pyridine, IC50 = 48 nM |
| SB 202190 | 4-[4-(4-fluorophenyl)-5-(4-pyridinyl)-1H-imidazol-2-yl]phenol |
| SB 239063 | trans-4-[4-(4-fluorophenyl)-5-(2-methoxy-4-pyrimidinyl)-1H-imidazol-1-yl]cyclohexanol, IC50 = 44 nM |
| SB 220025 | 5-(2-amino-4-pyrimidinyl)-4-(4-fluorophenyl)-1-(4-piperidinlyl)imidazole, IC50 = 19 nM |
| SB203580 hydrochloride | 4-[5-(4-fluorophenyl)-2-[4-(methylsulphonyl)phenyl]-1H-imidazol-4-yl]pyridine hydrochloride, IC50 = 50 nM |
| SB 85635 | |
| SB 242235 | 4-[4-(4-fluorophenyl)-1-(piperidin-4-yl)-1H-imidazol-5-yl]-2-methoxypyrimidine::4-[4-(4-fluorophenyl)-1-piperidin-4-yl-1H-imidazol-5-yl]-2-methoxypyrimidine |

TABLE 1-continued
Inhibitors of Mapk14 activity
| name | Chemical name or structure |
|---|---|
| SB 681323 | 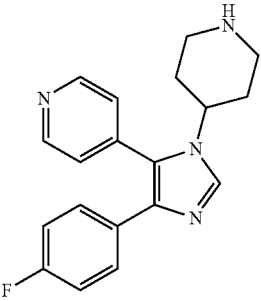 [SMILES: Fc1ccc(-c2ncn(C3CCNCC3)c2-c2ccncc2)cc1] |
| SB 210313 | 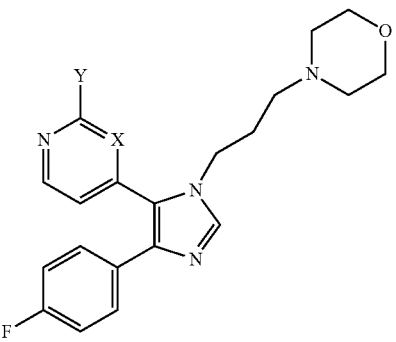<br>X = CH, Y = H<br>IC50 = 1300 nM |
| SB 216385 | 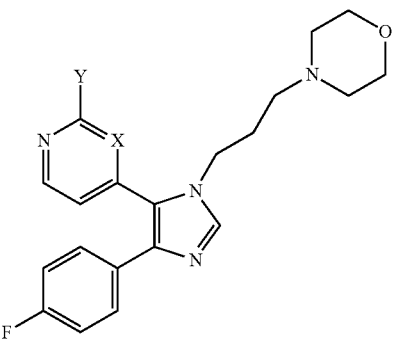<br>X = N, Y = NH$_2$<br>IC50 = 480 nM |
| Iosmapimod (856553) | |
| AW-814141 | 2-(hexahydrocyclopenta(c)pyrrol-2-ylamino)-8-methyl-6-o-tolyl-8H-pyrido(2,3-d)pyrimidine-7-one<br>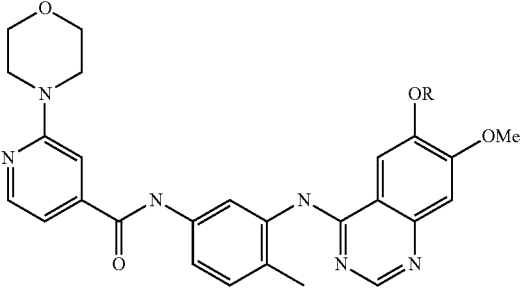 |

TABLE 1-continued

Inhibitors of Mapk14 activity

| name | Chemical name or structure |
|---|---|
| | 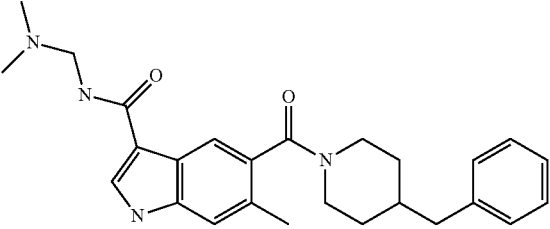 [SMILES: Cc1cc2[nH]cc(C(=O)NCN(C)C)c2cc1C(=O)N1CCC(Cc2ccccc2)CC1] |
| | 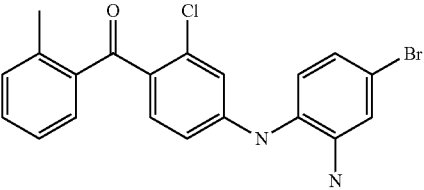 [SMILES: Cc1ccccc1C(=O)c1ccc(Nc2ccc(Br)cc2N)cc1Cl] |
| KR-003048 | 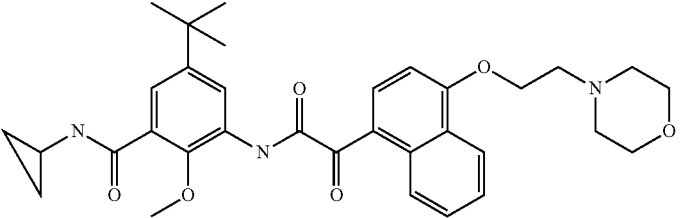 [SMILES: COc1c(NC(=O)C(=O)c2ccc(OCCN3CCOCC3)c3ccccc23)cc(C(C)(C)C)cc1C(=O)NC1CC1] |
| RWJ 67657 | 4-[4-(4-fluorophenyl)-1-(3-phenylpropyl)-5-(4-pyridinyl)-1H-imidazol-2-yl]-3-butyn-1-ol |
| SKF-86002 dihydrochloride | 6-(4-fluorophenyl)-2,3-dihydro-5-(4-pyridinyl)imidazo[2,1-b]thiazole dihydrochloride |
| TAK-715 | N-(4-(2-ethyl-4-(3-methylphenyl)-thiazol-5-yl)pyridin-2-yl)benzamide |
| JIP-1(153-163) | $C_{63}H_{108}N_{20}O_{16}$, corresponding to Arg-Pro-Lys-Arg-Pro-Thr-Thr-Leu-Asn-Leu-Phe-Nh2•AcOH (SEQ ID NO: 1369) |
| LY2228820 | 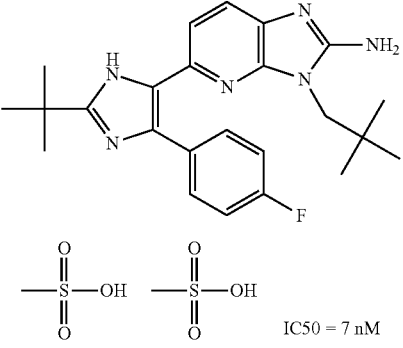 |
| RWJ67671 | 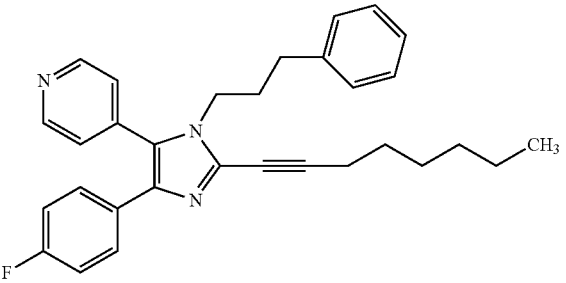 |

TABLE 1-continued
Inhibitors of Mapk14 activity
| name | Chemical name or structure |
|---|---|
| RWJ67568 | 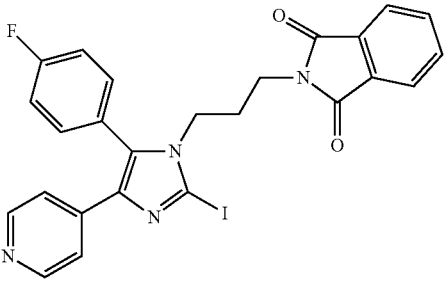 |
| RWJ67411 | 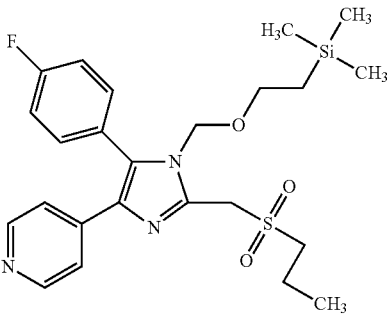 |
| RWJ66430 | 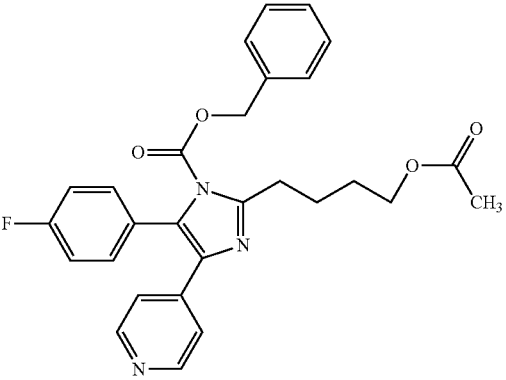 |
| SKF 86002 | 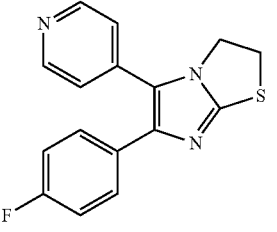<br>IC50 = 1500 nM |

TABLE 1-continued

Inhibitors of Mapk14 activity

| name | Chemical name or structure |
|------|---------------------------|
| L-167307 | 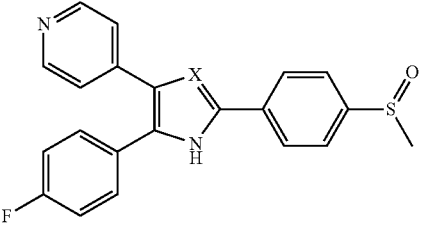 X = CH, IC50 = 5 nM |
| | (second structure, pyrazolone) |
| RWJ 68354 | 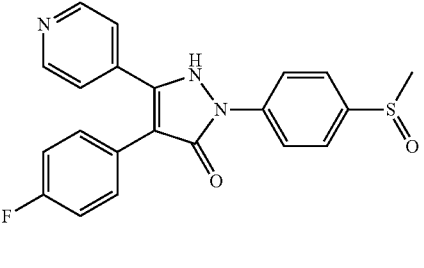 [SMILES: CS(=O)c1ccc(-n2[nH]c(-c3ccncc3)c(-c3ccc(F)cc3)c2=O)cc1] IC50 = 9 nM |
| JX 401 | 1-[2-methoxy-4-(methylthio)benzoyl]-4-(phenylmethyl)piperidine, IC50 = 32 nM |
| SC-68376 | 2-methyl-4-phenyl-5-(4-pyridyl)oxazole, IC50 = 2-5 μM |
| EO 1428 | (2-methylphenyl)-[4-[(2-amino-4-bromophenyl)amino]-2-chlorophenyl]methanone |
| CMPD-1 | 2'-fluoro-N-(4-hydroxyphenyl)-[1,1'-biphenyl]-4-butanamide |
| SD 169 | 1H-Indole-5-carboxamide, IC50 = 3.2 nM |
| R-130823 | 2-(4-fluorophenyl)-4-(1-phenethyl-1,2,3,6-tetrahydropyridin-4-yl)-3-(pyridin-4-yl)-1H-pyrrole, IC50 = 22 nM |
| SD282 | indole-5-carboxamide, IC50 = 0.0011 μM |
| | 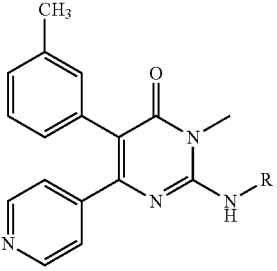 |

TABLE 1-continued
Inhibitors of Mapk14 activity
| name | Chemical name or structure |
|---|---|
| (WO2000031065) | 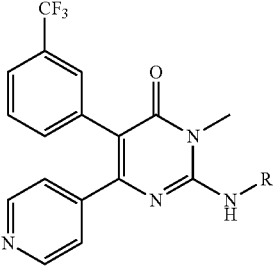 |
| (WO2000071535) | 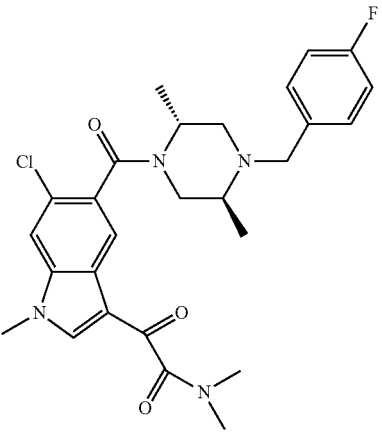 [SMILES: C[C@@H]1CN(Cc2ccc(F)cc2)[C@@H](C)CN1C(=O)c1cc2c(C(=O)C(=O)N(C)C)cn(C)c2cc1Cl] |
|  | 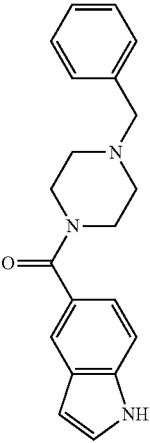 [SMILES: O=C(c1ccc2[nH]ccc2c1)N1CCN(Cc2ccccc2)CC1] |

TABLE 1-continued
Inhibitors of Mapk14 activity
| name | Chemical name or structure |
|---|---|
| | 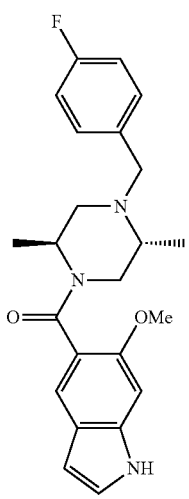 [SMILES: COc1cc2[nH]ccc2cc1C(=O)N1C[C@@H](C)N(Cc2ccc(F)cc2)C[C@@H]1C] |
| SCIO 469 (talmapimod) | 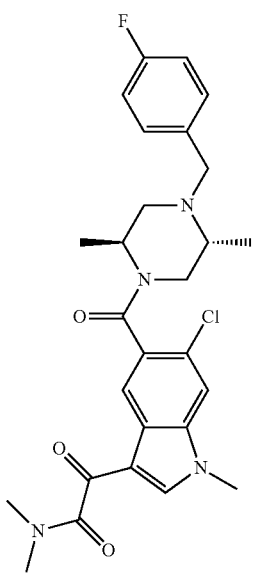<br>IC50 p38α = 9 nM<br><br>1H-indole-3-acetamide,6-chloro-5-[[(2R,5S)-4-[(4-fluorophenyl)methyl]-2,5-dimethyl-1-piperazinyl]carbonyl]-N,N,1-trimethyl-α-oxo-2-[6-chloro-5-[[(2R,5S)-4-(4-fluorobenzyl)-2,5-dimethylpiperazin-1-yl]carbonyl]-1-methyl-1H-indol-3-yl]-N,N-dimethyl-2-oxoacetamide |

TABLE 1-continued

Inhibitors of Mapk14 activity

| name | Chemical name or structure |
| --- | --- |

| | |
|---|---|
| name | Chemical name or structure |
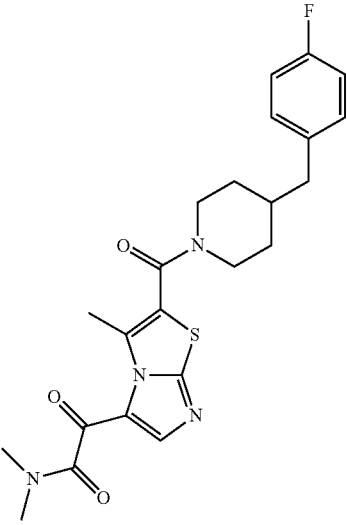 [SMILES: Cc1c(C(=O)N2CCC(Cc3ccc(F)cc3)CC2)sc2ncc(C(=O)C(=O)N(C)C)n12]
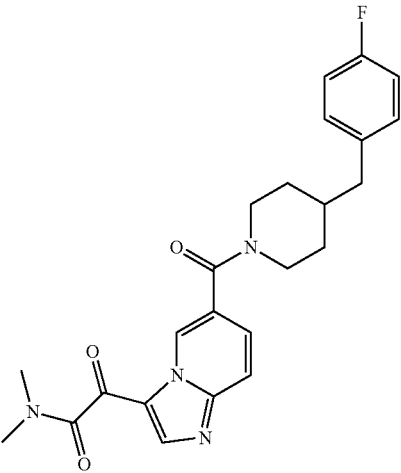 [SMILES: CN(C)C(=O)C(=O)c1cnc2ccc(C(=O)N3CCC(Cc4ccc(F)cc4)CC3)cn12]
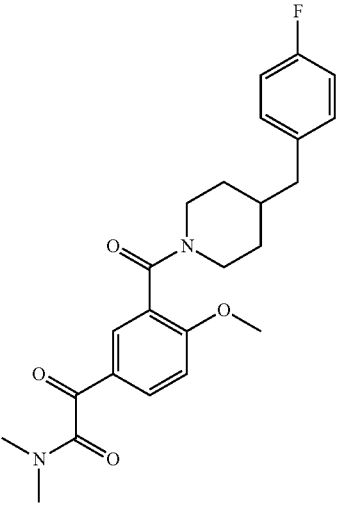 [SMILES: COc1ccc(C(=O)C(=O)N(C)C)cc1C(=O)N1CCC(Cc2ccc(F)cc2)CC1]

TABLE 1-continued
Inhibitors of Mapk14 activity
| name | Chemical name or structure |
|---|---|
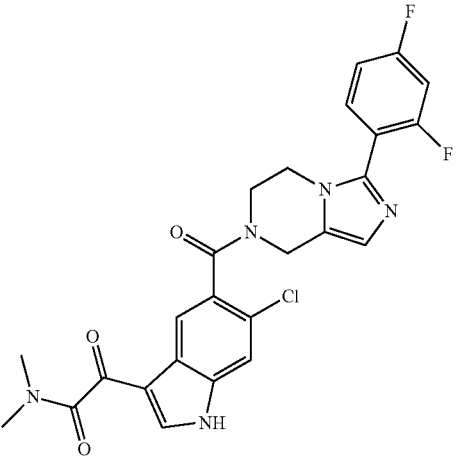
IC50 = 11 nM
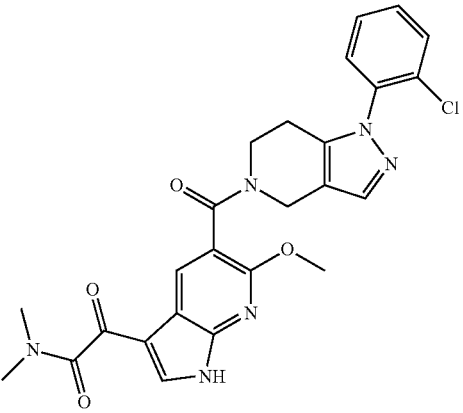
IC50 = 29 nM
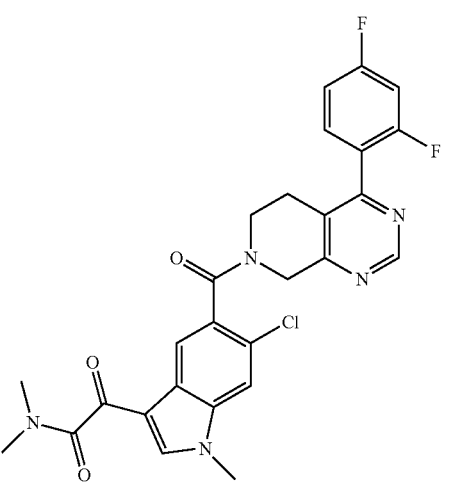 [SMILES: CN(C)C(=O)C(=O)c1cn(C)c2cc(Cl)c(C(=O)N3CCc4c(ncnc4-c4ccc(F)cc4F)C3)cc12]
SCIO 323
SCIO 469 hydrochloride  6-chloro-5-[[(2R,5S)-4-[(4-fluorophenyl)methyl]-2,5-dimethyl-1-piperazinyl]carbonyl]-N,N,1-trimethyl-α-oxo-1H-Indole-3-acetamide hydrochloride, IC50 = 9 nM TABLE 1-continued
Inhibitors of Mapk14 activity
| name | Chemical name or structure |
| --- | --- |
| SKF 86002 dihydrochloride | 6-(4-fluorophenyl)-2,3-dihydro-5-(4-pyridinyl)imidazo[2,1-b]thiazole dihydrochloride, IC50 = 0.1-1 µM |
| VX 702 | 6-[(aminocarbonyl)(2,6-difluorophenyl)amino]-2-(2,4-difluorophenyl)-3-pyridinecarboxamide, IC50 = 31 nM |
| VX 745 | 5-(2,6-dichlorophenyl)-2-[2,4-difluorophenyl)thio]-6H-pyrimido[1,6-b]pyridazin-6-one, IC50 = 5 nM |
| VX 850 | IC50 = 0.1 µM |
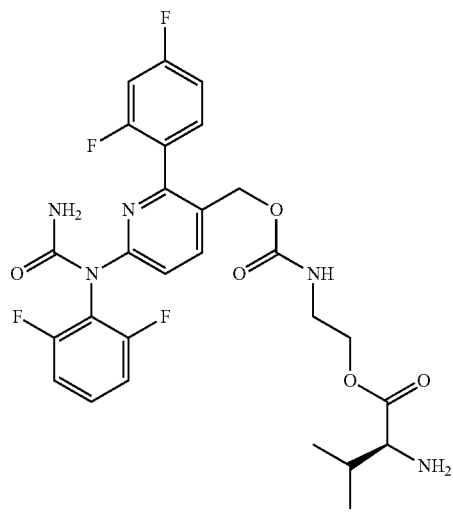
IC50 = 31 nM
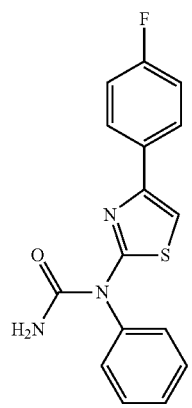 [SMILES: NC(=O)N(c1ccccc1)c1nc(-c2ccc(F)cc2)cs1]
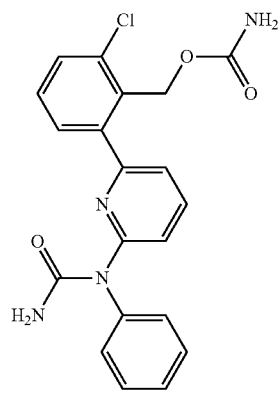 [SMILES: NC(=O)OCc1c(Cl)cccc1-c1cccc(N(C(N)=O)c2ccccc2)n1]

TABLE 1-continued
Inhibitors of Mapk14 activity
| name | Chemical name or structure |
| --- | --- |
| PH-797804 | 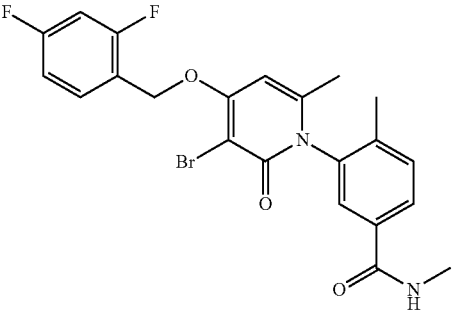<br>IC50 = 2.3 nM |
| SX 011 | 6-Chloro-5-[[4-[(4-fluorophenyl)methyl]-1-piperidinyl]carbonyl-N,N,1-trimethyl-α-oxo-1H-indole-3-acetamide, IC50 = 9 nM |
| BIRB 796 | 1-[5-tert-butyl-2-(4-methylphenyl)pyrazol-3-yl]-3-[4-(2-morpholin-4-ylethoxy)naphthalen-1-yl]urea, IC50 = 23 nM |
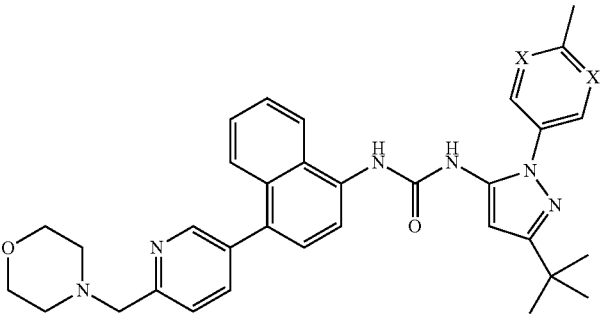
X = CH
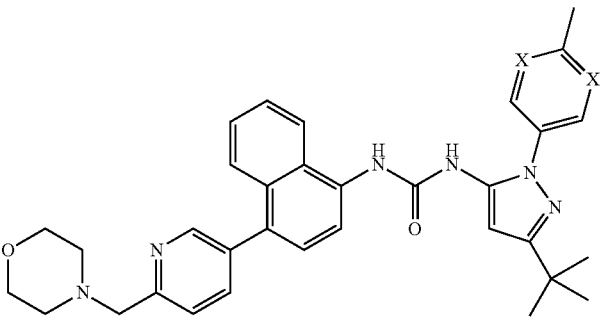
X = N
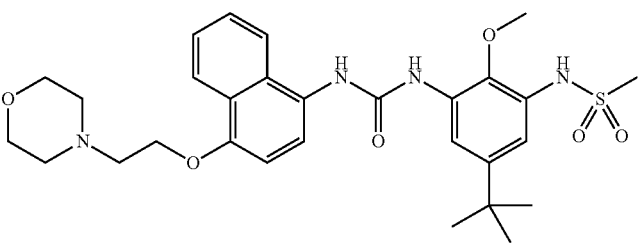 [SMILES: COc1c(NC(=O)Nc2ccc(OCCN3CCOCC3)c3ccccc23)cc(C(C)(C)C)cc1NS(C)(=O)=O]

TABLE 1-continued
Inhibitors of Mapk14 activity
| name | Chemical name or structure |
|---|---|
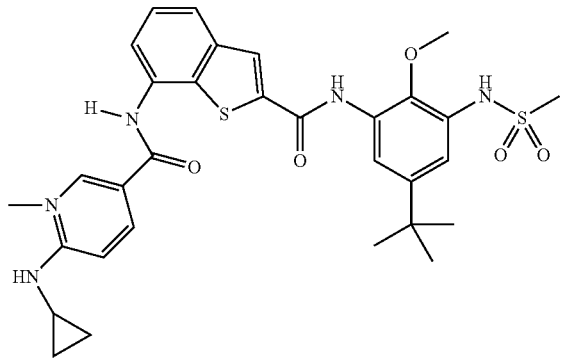
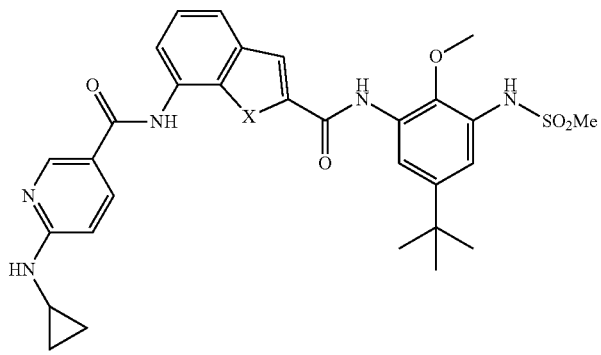
73 (X = NMe)
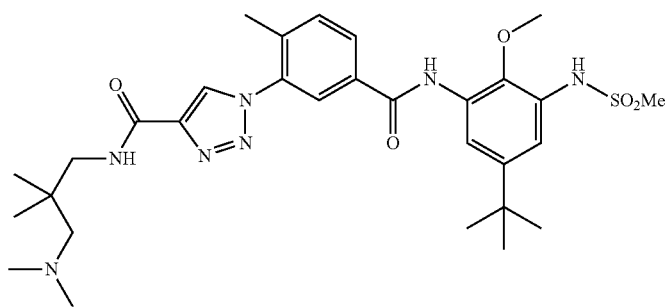 [SMILES: COc1c(NC(=O)c2ccc(C)c(-n3cc(C(=O)NCC(C)(C)CN(C)C)nn3)c2)cc(C(C)(C)C)cc1NS(C)(=O)=O]
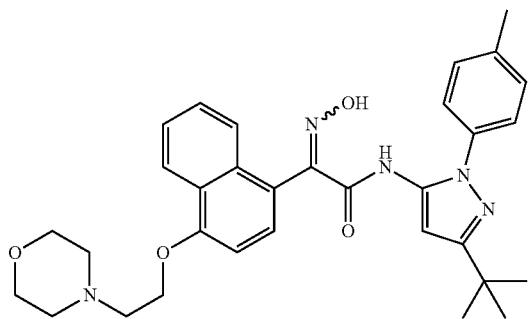 [SMILES: Cc1ccc(-n2nc(C(C)(C)C)cc2NC(=O)C(=NO)c2ccc(OCCN3CCOCC3)c3ccccc23)cc1]

TABLE 1-continued
Inhibitors of Mapk14 activity
| name | Chemical name or structure |
|---|---|
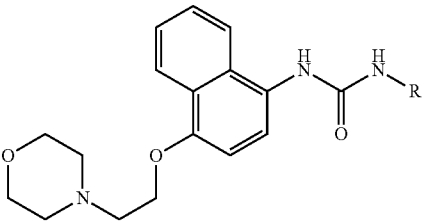
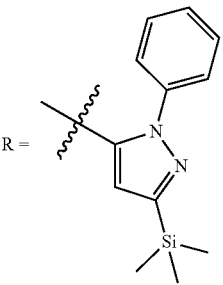 [SMILES: *c1cc([Si](C)(C)C)nn1-c1ccccc1]
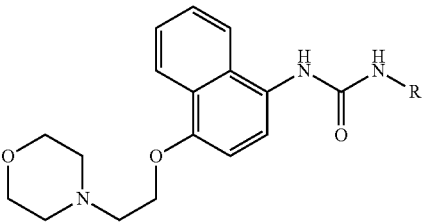
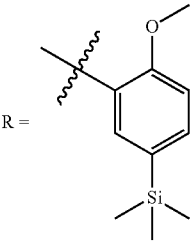 [SMILES: *c1cc([Si](C)(C)C)ccc1OC]
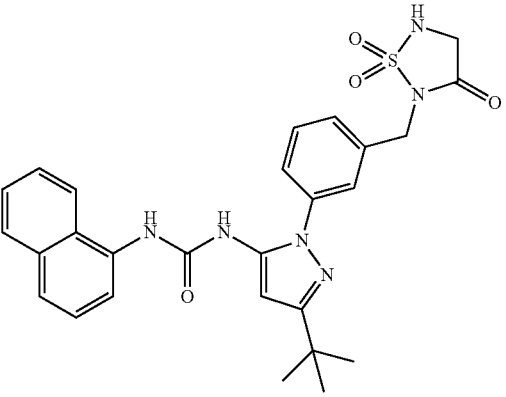
IC50 = 19 nM TABLE 1-continued
Inhibitors of Mapk14 activity
| name | Chemical name or structure |
|---|---|
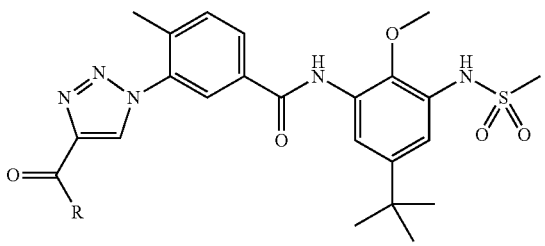
R = 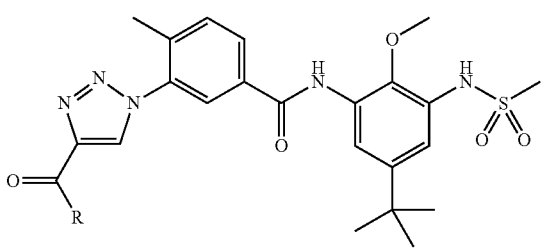
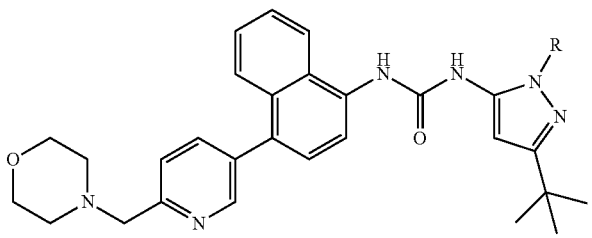
(R = 4-tolyl)
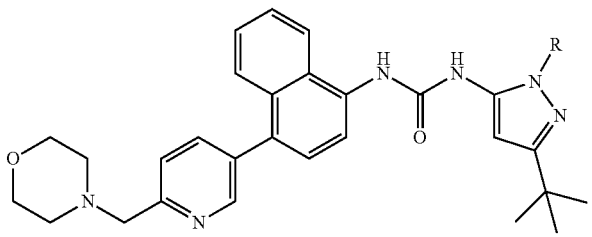
(R = 2-methylpyrimidin-5-yl)
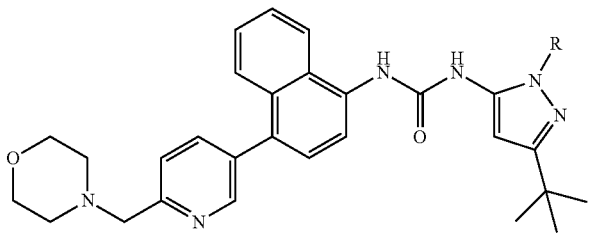
(R = 1-methyl-1H-pyrazol-4-yl)

TABLE 1-continued

Inhibitors of Mapk14 activity

| name | Chemical name or structure |
|---|---|

IC50 = 6 nM

TABLE 1-continued

Inhibitors of Mapk14 activity

| name | Chemical name or structure |
|------|---------------------------|

IC50 = 3.1 nM

IC50 = 0.98 nM (X = N)

X = CH

татв
TABLE 1-continued
Inhibitors of Mapk14 activity
| name | Chemical name or structure |
|---|---|
| | 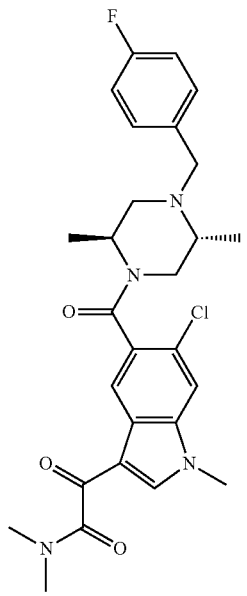 |
| | 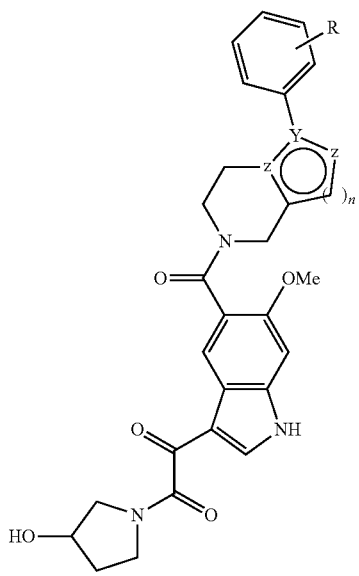 |

TABLE 1-continued
Inhibitors of Mapk14 activity
| name | Chemical name or structure |
|------|----------------------------|
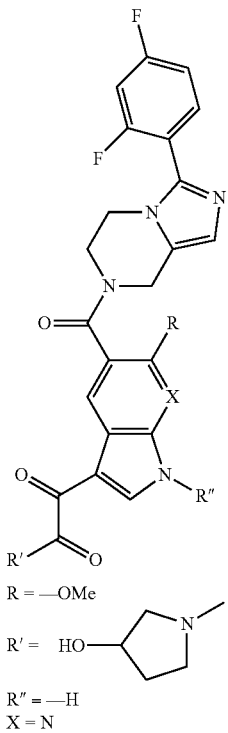
R = —OMe
R' = HO-[3-(1-methylpyrrolidinyl)]
R'' = —H
X = N
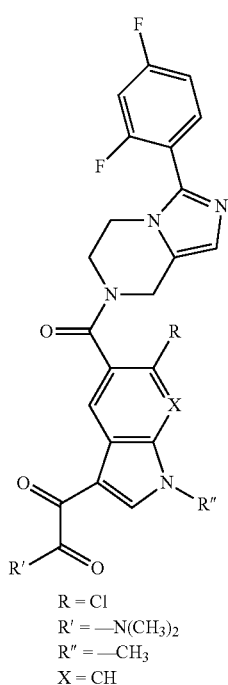
R = Cl
R' = —N(CH$_3$)$_2$
R'' = —CH$_3$
X = CH TABLE 1-continued
Inhibitors of Mapk14 activity
| name | Chemical name or structure |
| --- | --- |
|  | 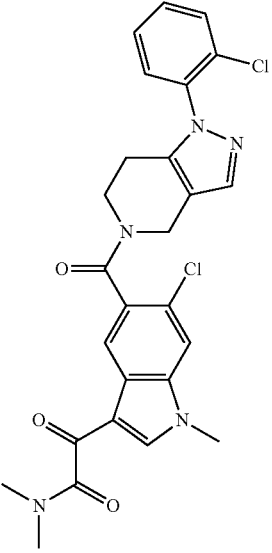 [SMILES: CN(C)C(=O)C(=O)c1cn(C)c2cc(Cl)c(C(=O)N3CCc4c(cnn4-c4ccccc4Cl)C3)cc12] |
|  | 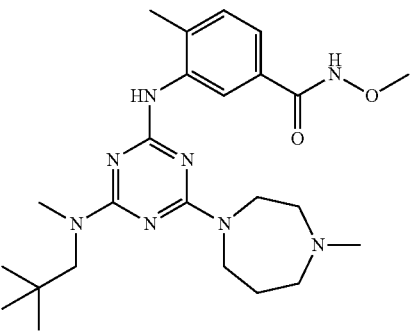<br>IC50 = 44 nM |
|  | 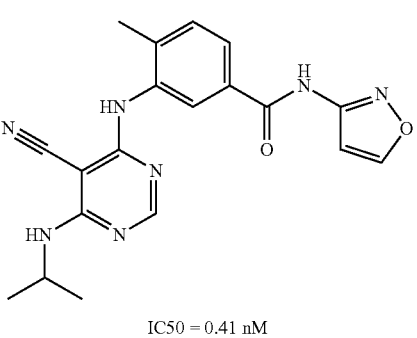 [SMILES: Cc1ccc(C(=O)Nc2ccon2)cc1Nc1ncnc(NC(C)C)c1C#N]<br>IC50 = 0.41 nM |
|  | 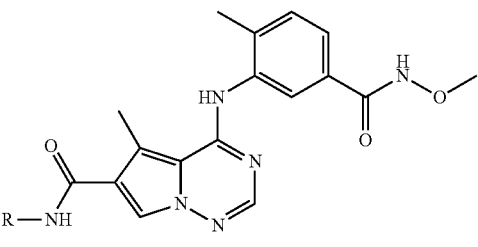<br>R = Et<br>IC50 = 3.1 nM |

TABLE 1-continued
Inhibitors of Mapk14 activity
| name | Chemical name or structure |
| --- | --- |
| | 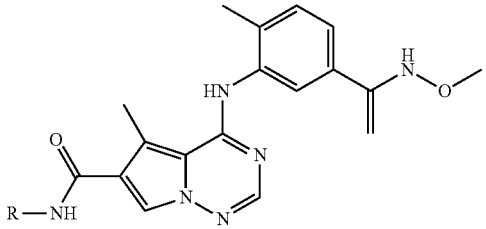
R = (S)-α-Me-benzyl
IC50 = 2.2 nM |
| | 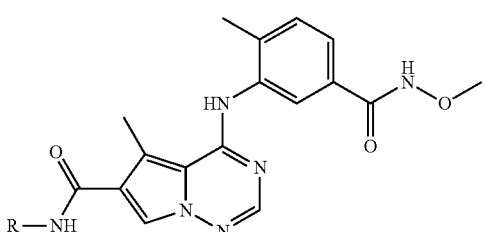
R = (S)-α-Me-benzyl
IC50 = 0.46 nM |
| | 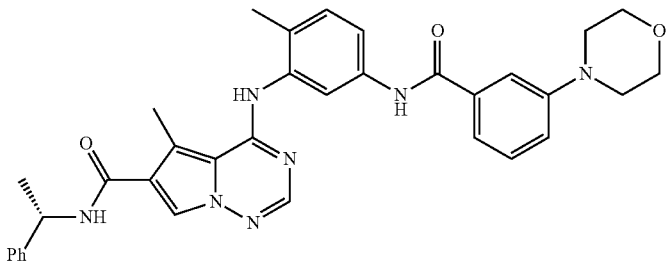 [SMILES: Cc1ccc(NC(=O)c2cccc(N3CCOCC3)c2)cc1Nc1ncnn2cc(C(=O)N[C@@H](C)c3ccccc3)c(C)c12] |
| BMS-640994 | 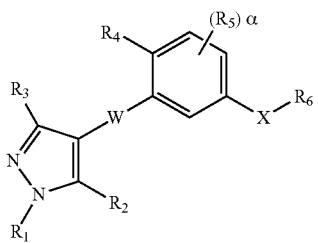
IC50 = 3.5 nM |

TABLE 1-continued

Inhibitors of Mapk14 activity

| name | Chemical name or structure |
|------|----------------------------|

TABLE 1-continued
Inhibitors of Mapk14 activity
| name | Chemical name or structure |
|------|----------------------------|
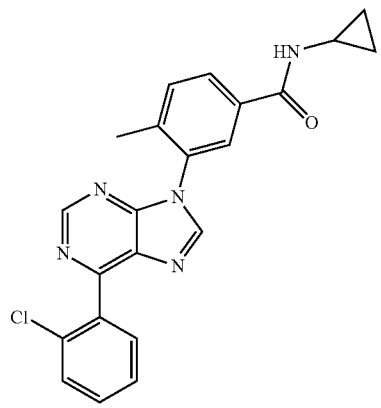 [SMILES: Cc1ccc(C(=O)NC2CC2)cc1-n1cnc2c(-c3ccccc3Cl)ncnc21]
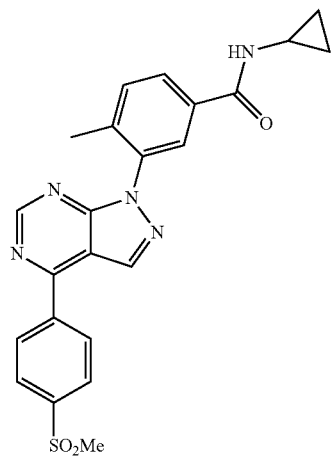 [SMILES: Cc1ccc(C(=O)NC2CC2)cc1-n1ncc2c(-c3ccc(S(C)(=O)=O)cc3)ncnc21]
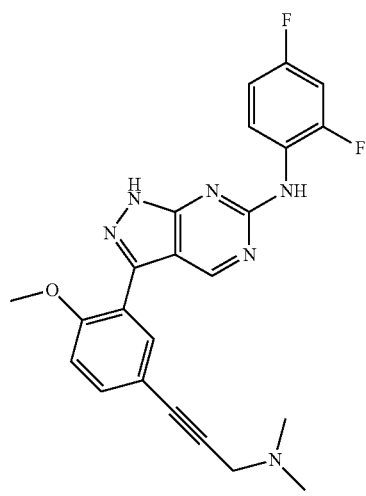
IC50 = 0.6 nM TABLE 1-continued
Inhibitors of Mapk14 activity
| name | Chemical name or structure |
| --- | --- |
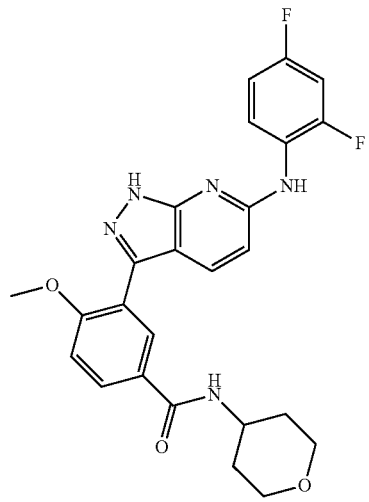
IC50 = 0.7 nM
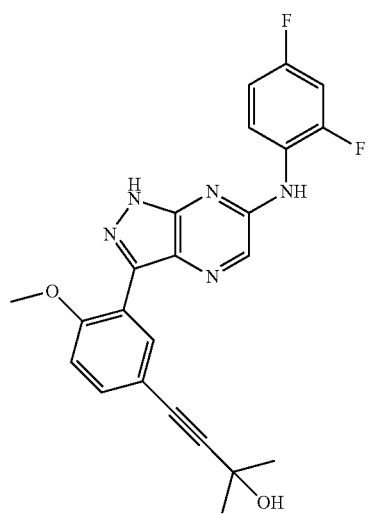
IC50 = 7 nM TABLE 1-continued Inhibitors of Mapk14 activity

| name | Chemical name or structure |
|---|---|

[Structure: 4-(2,4-difluorophenyl)-substituted tetrahydropyrido-pyrimidine linked via amide to chloro-N-methylindole bearing an α-ketoamide with N,N-dimethyl group]

[Structure: benzophenone with R₁ on one ring, R₂ on the other, linked via NH to a phenyl bearing R₃]

[Structure: dibenzo fused tricyclic ketone with X—Y bridge, NH-phenyl-R₂ substituent]

[Structure: fused tricyclic scaffold]

X, Y = CH, CH$_2$, O, S
A = CH$_2$, N, O
z = N, CH
IC50 = 6 nM

| | |
|---|---|
| BI 78D3 | 4-(2,3-Dihydro-1,4-benzodioxin-6-yl)-2,4-dihydro-5-[(5-nitro-2-thiazolyl)thio]-3H-1,2,4-triazol-3-one |
| CGH 2466 dihydrochloride | 4-(3,4-Dichlorophenyl)-5-(4-pyridinyl)-2-thiazolamine dihydrochloride |
| PD 169316 | 4-[5-(4-fluorophenyl)-2-(4-nitrophenyl)-1H-imidazol-4-yl]-pyridine, IC50 = 15 nM |

TABLE 1-continued
Inhibitors of Mapk14 activity
| name | Chemical name or structure |
|---|---|
| RO 3201195 | 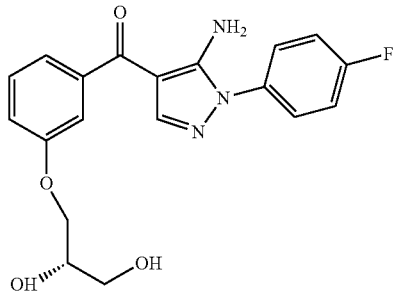 [SMILES: Nc1c(C(=O)c2cccc(OC[C@@H](O)CO)c2)cnn1-c1ccc(F)cc1] |
| RO4402257 | |
| AMG 548 | 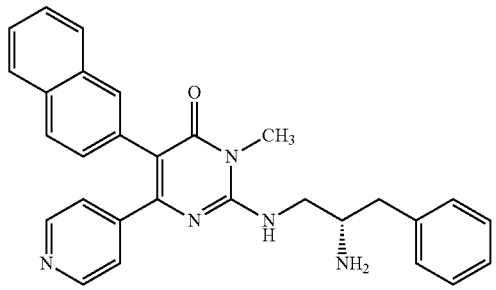 [SMILES: Cn1c(NC[C@@H](N)Cc2ccccc2)nc(-c2ccncc2)c(-c2ccc3ccccc3c2)c1=O] |
| GSK 681323 | |
| AVE 9940 | |
| PS 540446 | |
| PS 516895 | |
| SC 80036 | 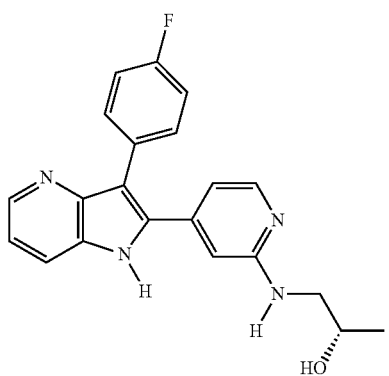 [SMILES: C[C@H](O)CNc1cc(-c2[nH]c3cccnc3c2-c2ccc(F)cc2)ccn1] |

TABLE 1-continued
Inhibitors of Mapk14 activity
| name | Chemical name or structure |
| --- | --- |
| PH 797804 | 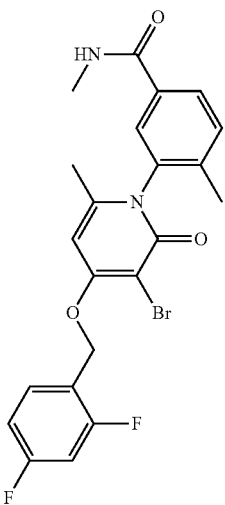 [SMILES: CNC(=O)c1ccc(C)c(-n2c(C)cc(OCc3ccc(F)cc3F)c(Br)c2=O)c1] |
| | 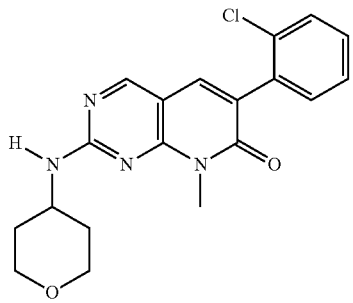 [SMILES: Cn1c(=O)c(-c2ccccc2Cl)cc2cnc(NC3CCOCC3)nc21] |
| TAK 715 | N-(4-(2-Ethyl-4-(3-methylphenyl)-thiazol-5-yl)31yridine-2-yl)benzamide, IC50 = 7.1 nM |
| R1487 | 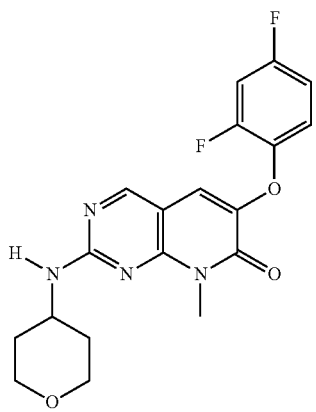<br>IC50 = 10 nM |

TABLE 1-continued
Inhibitors of Mapk14 activity
| name | Chemical name or structure |
|------|---------------------------|
|  | 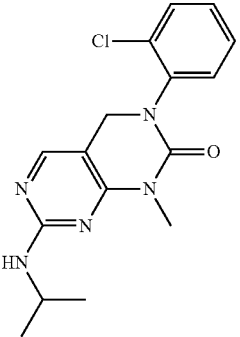 [SMILES: CC(C)Nc1ncc2c(n1)N(C)C(=O)N(c1ccccc1Cl)C2] |
|  | 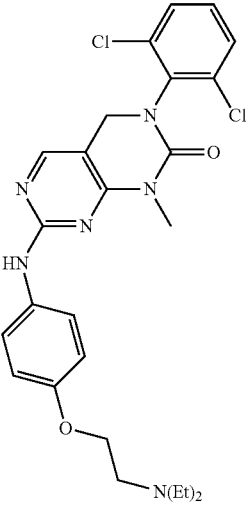 |
| Pamapimod | 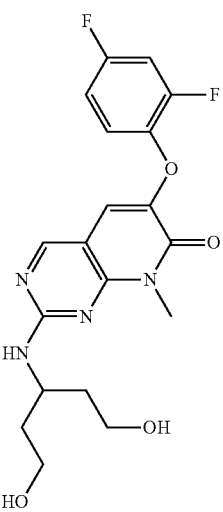<br>IC50 = 14 nM, |

TABLE 1-continued
Inhibitors of Mapk14 activity
| name | Chemical name or structure |
|---|---|
| | 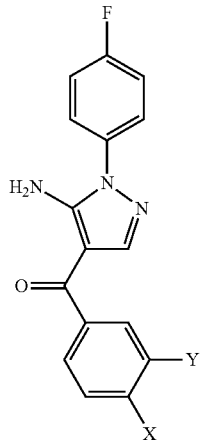 |
| | 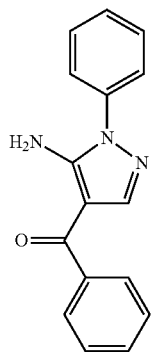 |
| | 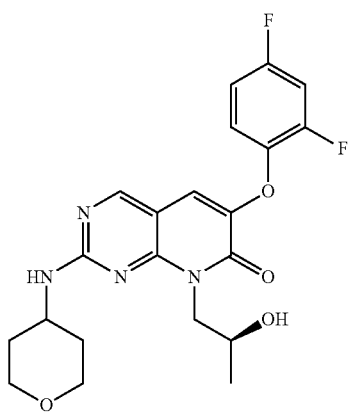 [SMILES: C[C@H](O)Cn1c(=O)c(Oc2ccc(F)cc2F)cc2cnc(NC3CCOCC3)nc21] |

US 10,441,577 B2
61
62
TABLE 1-continued
Inhibitors of Mapk14 activity
| name | Chemical name or structure |
|---|---|
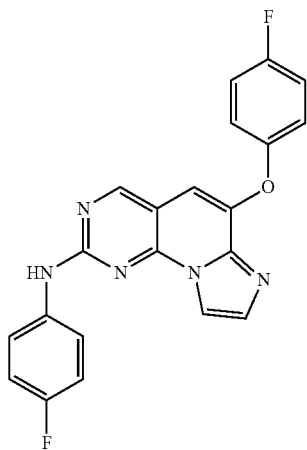 [SMILES: Fc1ccc(Nc2ncc3cc(Oc4ccc(F)cc4)c4nccn4c3n2)cc1]
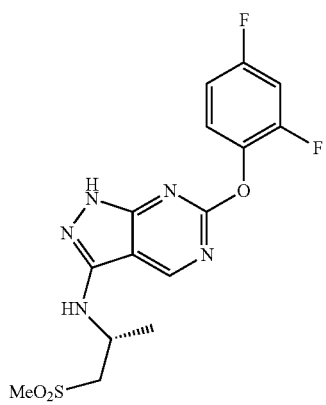 [SMILES: C[C@H](CS(C)(=O)=O)Nc1n[nH]c2nc(Oc3ccc(F)cc3F)ncc12]
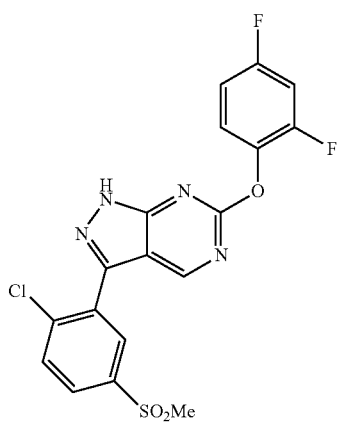 [SMILES: CS(=O)(=O)c1ccc(Cl)c(-c2n[nH]c3nc(Oc4ccc(F)cc4F)ncc23)c1]

TABLE 1-continued
Inhibitors of Mapk14 activity
| name | Chemical name or structure |
|---|---|
|  | 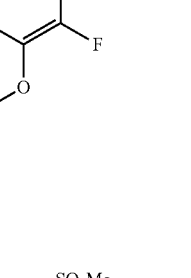 |
| SD-06 | 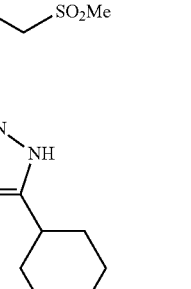 |
|  | 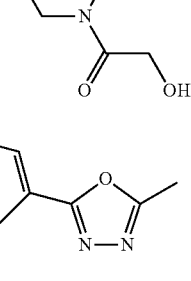 |
|  |  |

TABLE 1-continued
Inhibitors of Mapk14 activity
| name | Chemical name or structure |
|---|---|
| | 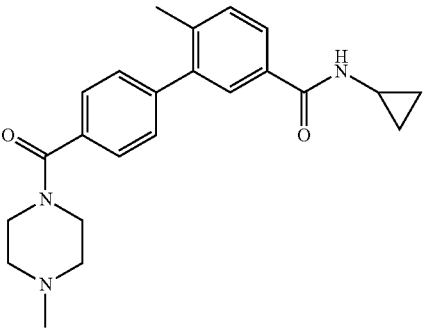 [SMILES: Cc1ccc(C(=O)NC2CC2)cc1-c1ccc(C(=O)N2CCN(C)CC2)cc1] |
| | 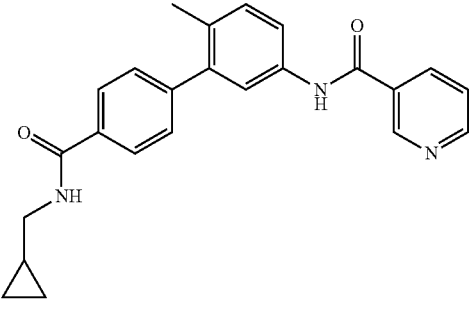 [SMILES: Cc1ccc(NC(=O)c2cccnc2)cc1-c1ccc(C(=O)NCC2CC2)cc1] |
| | 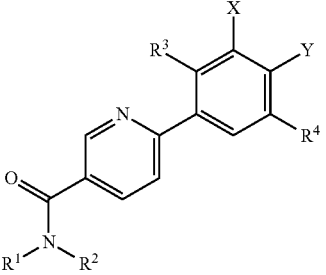 |
| | 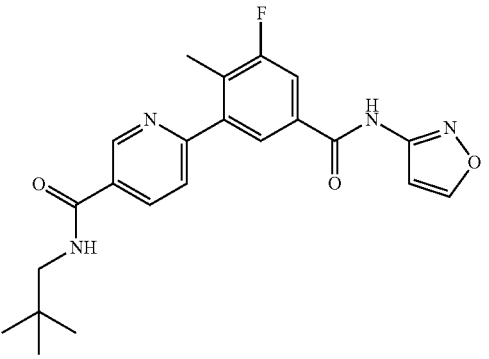 [SMILES: Cc1c(F)cc(C(=O)Nc2ccon2)cc1-c1ccc(C(=O)NCC(C)(C)C)cn1] |
| | 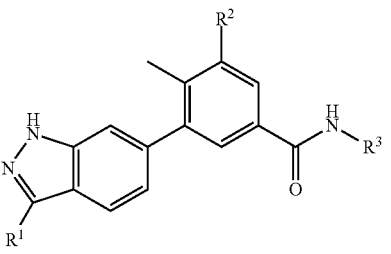 |

TABLE 1-continued

Inhibitors of Mapk14 activity

| name | Chemical name or structure |
|------|---------------------------|
| | (structures only) |

TABLE 1-continued
Inhibitors of Mapk14 activity
| name | Chemical name or structure |
|---|---|
| | 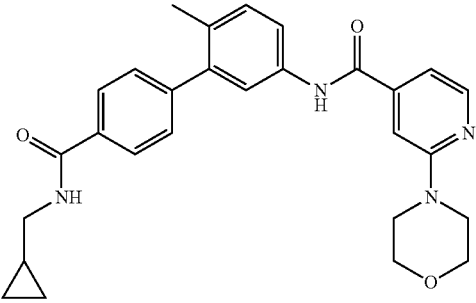 [SMILES: Cc1ccc(NC(=O)c2ccnc(N3CCOCC3)c2)cc1-c1ccc(C(=O)NCC2CC2)cc1] |
| BMS (WO04043912) | 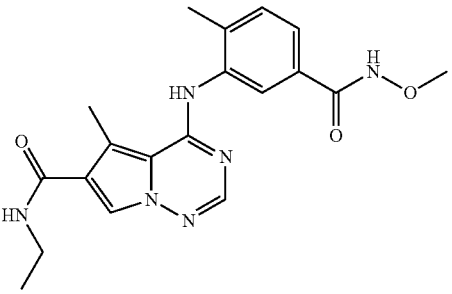 [SMILES: CCNC(=O)c1cn2ncnc(Nc3cc(C(=O)NOC)ccc3C)c2c1C] |
| | 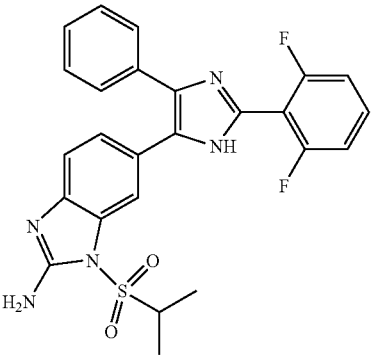 [SMILES: CC(C)S(=O)(=O)n1c(N)nc2ccc(-c3[nH]c(-c4c(F)cccc4F)nc3-c3ccccc3)cc21] |
| | 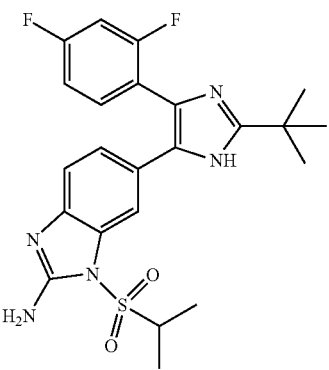
IC50 = 4.4 nM |

TABLE 1-continued
Inhibitors of Mapk14 activity
| name | Chemical name or structure |
|---|---|
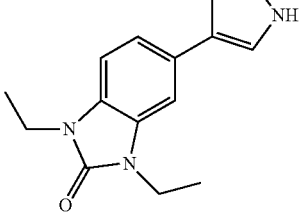
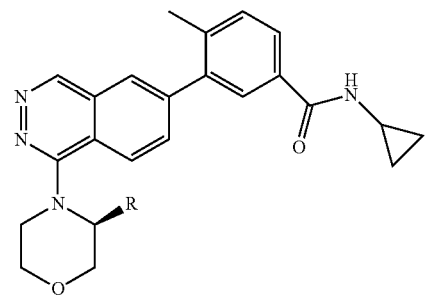
R = CH₃
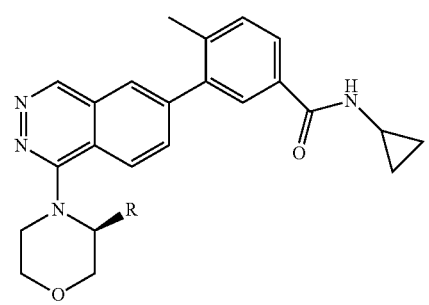
R = H
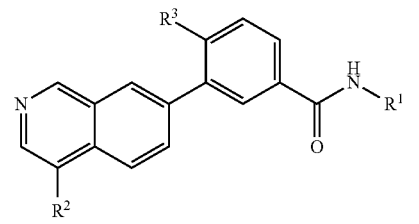
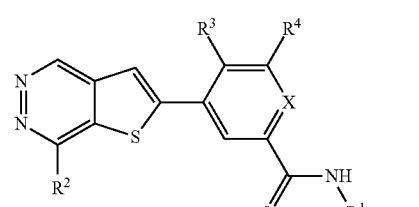

TABLE 1-continued

Inhibitors of Mapk14 activity

| name | Chemical name or structure |
|---|---|

IC50 = 2.4 nM

TABLE 1-continued
Inhibitors of Mapk14 activity
| name | Chemical name or structure |
| --- | --- |
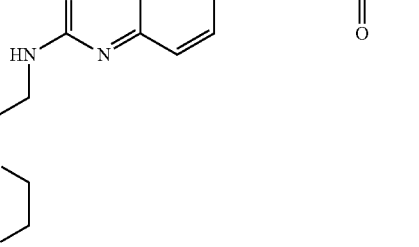
R¹ = m-CF₃Ph
IC50 = 2.7 nM
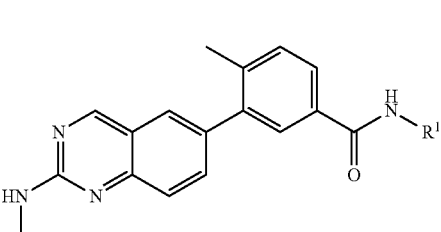
R1 = cyclopropyl
IC50 = 2 nM
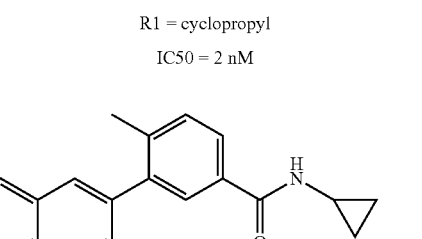
R² = I-morpholino
IC50 = 1.2 nM
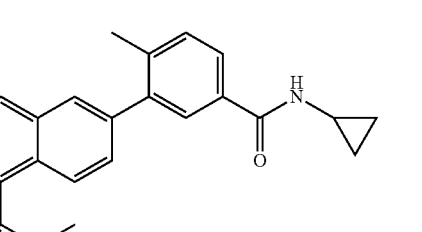
IC50 = 0.8 nM TABLE 1-continued
Inhibitors of Mapk14 activity
| name | Chemical name or structure |
|------|---------------------------|
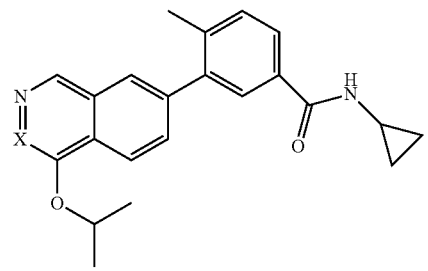
X = N
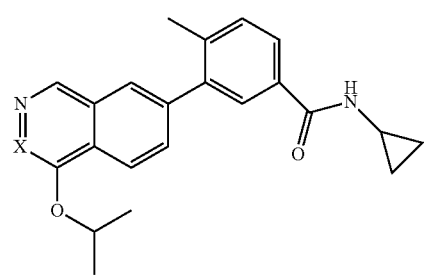
X = CH
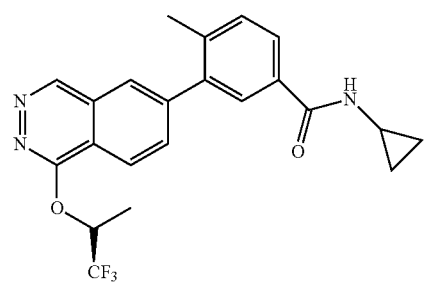
IC50 = 1 nM
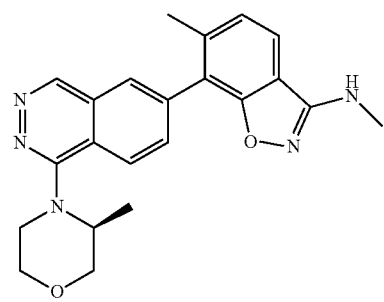 [SMILES: CNc1noc2c(-c3ccc4c(N5CCOC[C@@H]5C)nncc4c3)c(C)ccc12]
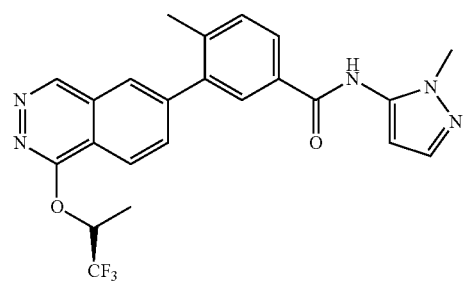 [SMILES: Cc1ccc(C(=O)Nc2ccnn2C)cc1-c1ccc2c(O[C@@H](C)C(F)(F)F)nncc2c1]

TABLE 1-continued
Inhibitors of Mapk14 activity
| name | Chemical name or structure |
|------|----------------------------|
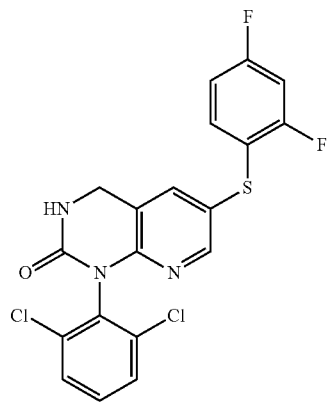
IC50 = 25 nM
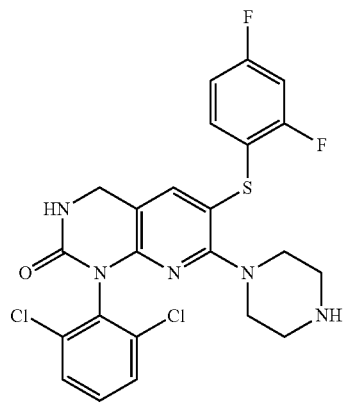
IC50 = 0.2 nM
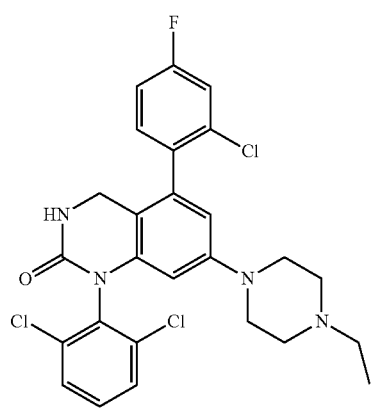
IC50 = 0.5 nM TABLE 1-continued
Inhibitors of Mapk14 activity
| name | Chemical name or structure |
|------|----------------------------|
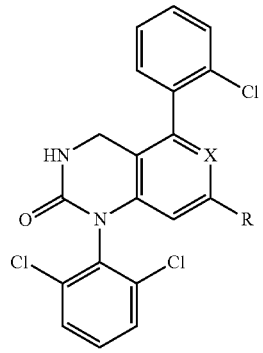
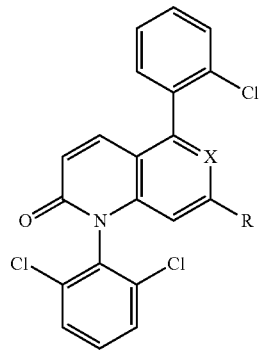
(X = CH, N)
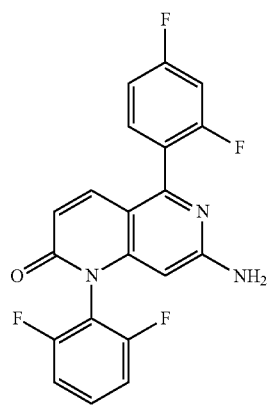
IC50 = 0.69 nM TABLE 1-continued
Inhibitors of Mapk14 activity
| name | Chemical name or structure |
|------|----------------------------|
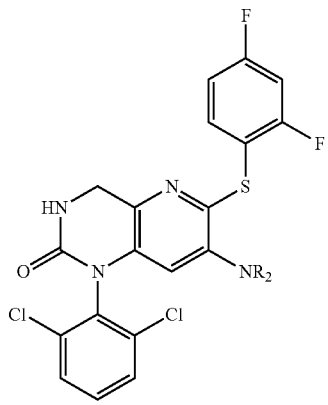
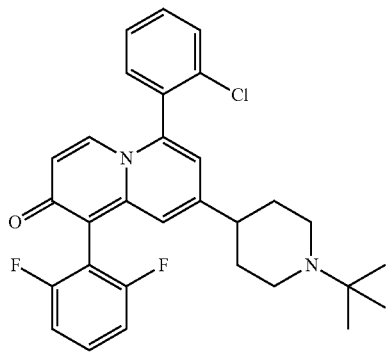 [SMILES: CC(C)(C)N1CCC(c2cc(-c3ccccc3Cl)n3ccc(=O)c(-c4c(F)cccc4F)c3c2)CC1]
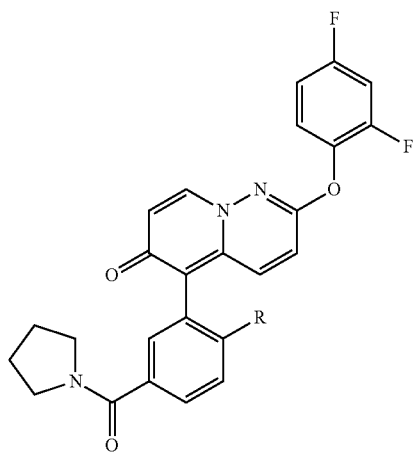
(R = OMe)

TABLE 1-continued
Inhibitors of Mapk14 activity
| name | Chemical name or structure |
|---|---|
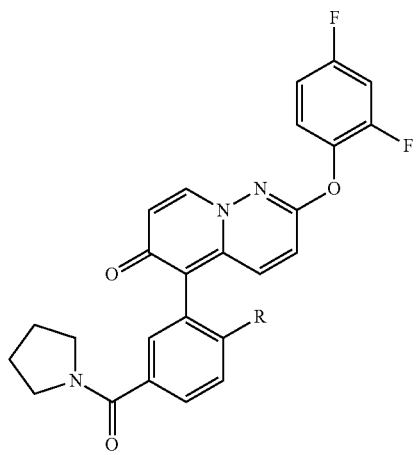
(R = Et)
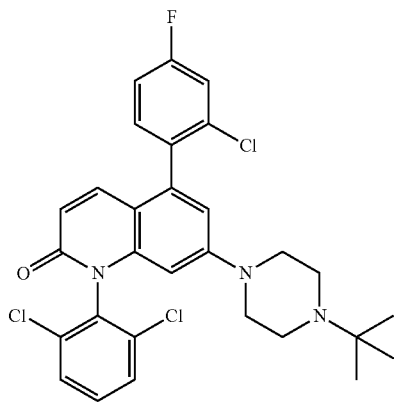 [SMILES: CC(C)(C)N1CCN(c2cc(-c3ccc(F)cc3Cl)c3ccc(=O)n(-c4c(Cl)cccc4Cl)c3c2)CC1]
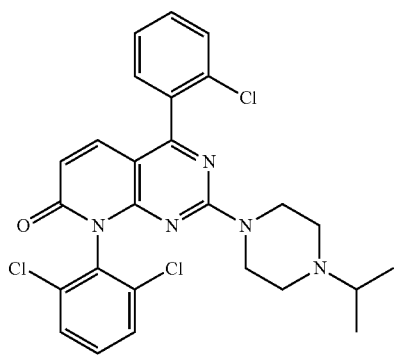 [SMILES: CC(C)N1CCN(c2nc(-c3ccccc3Cl)c3ccc(=O)n(-c4c(Cl)cccc4Cl)c3n2)CC1]

TABLE 1-continued
Inhibitors of Mapk14 activity
| name | Chemical name or structure |
|---|---|
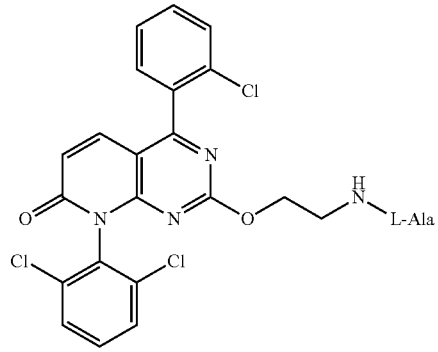
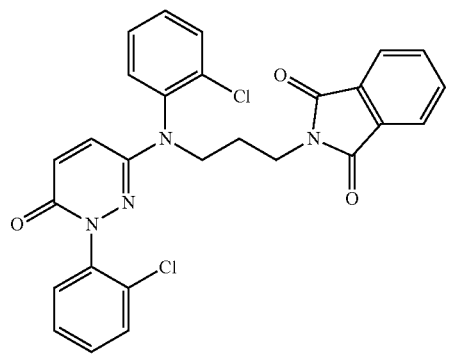
IC50 = 5 nM
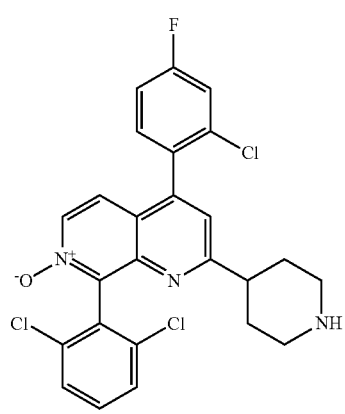

TABLE 1-continued
Inhibitors of Mapk14 activity
| name | Chemical name or structure |
|---|---|
| | 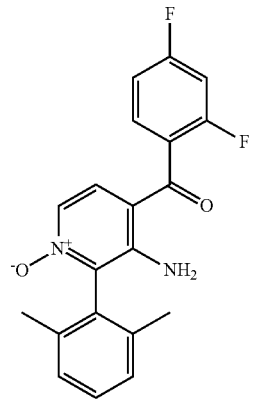
IC50 = 6 nM |
| | 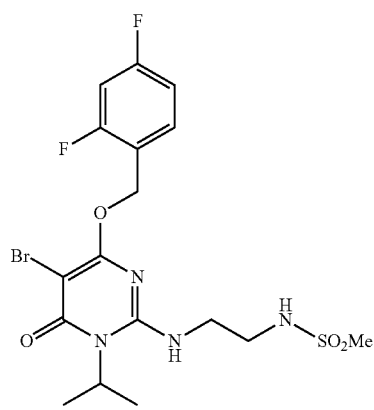
IC50 = 1.7 nM |
| | 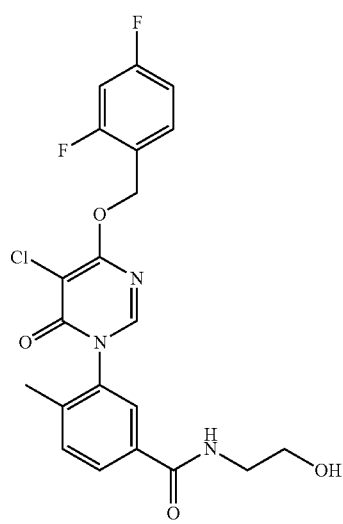 [SMILES: Cc1ccc(C(=O)NCCO)cc1-n1cnc(OCc2ccc(F)cc2F)c(Cl)c1=O] |

TABLE 1-continued
Inhibitors of Mapk14 activity
| name | Chemical name or structure |
|------|---------------------------|
|  | 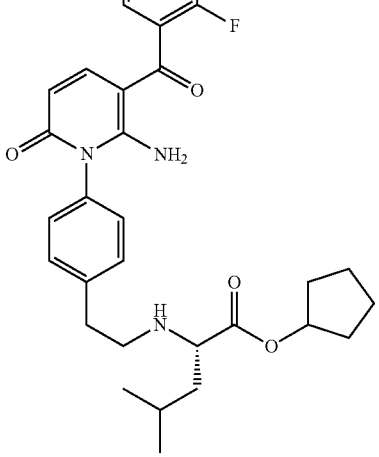<br>IC50 < 50 nM |
|  | 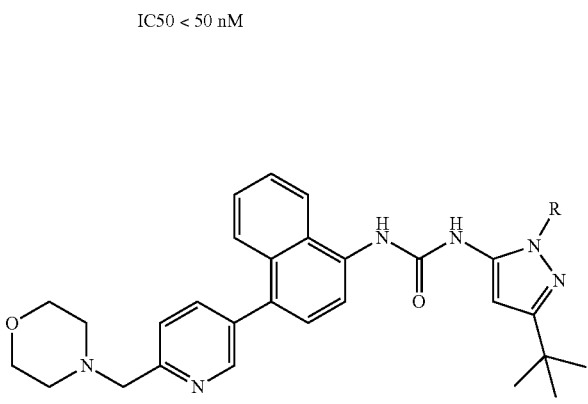<br>(R = 4-tolyl) |
|  | 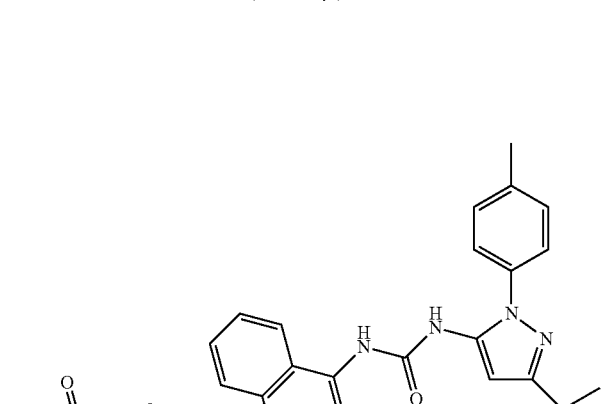<br>IC50 = 34 nM |

TABLE 1-continued
Inhibitors of Mapk14 activity
| name | Chemical name or structure |
|------|---------------------------|
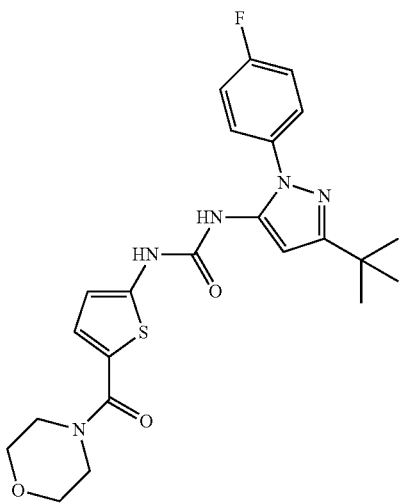 [SMILES: CC(C)(C)c1cc(NC(=O)Nc2ccc(C(=O)N3CCOCC3)s2)n(-c2ccc(F)cc2)n1]
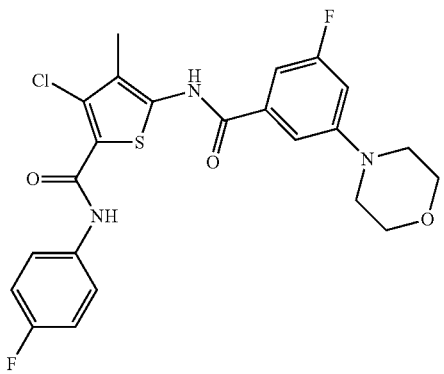 [SMILES: Cc1c(NC(=O)c2cc(F)cc(N3CCOCC3)c2)sc(C(=O)Nc2ccc(F)cc2)c1Cl]
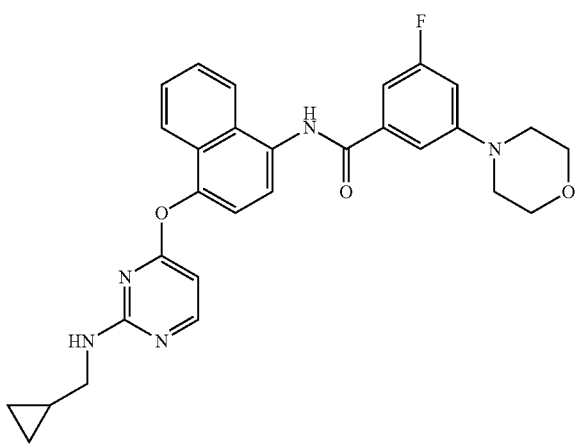
IC50 = 2.5 nM TABLE 1-continued
Inhibitors of Mapk14 activity
| name | Chemical name or structure |
|------|----------------------------|
|      | 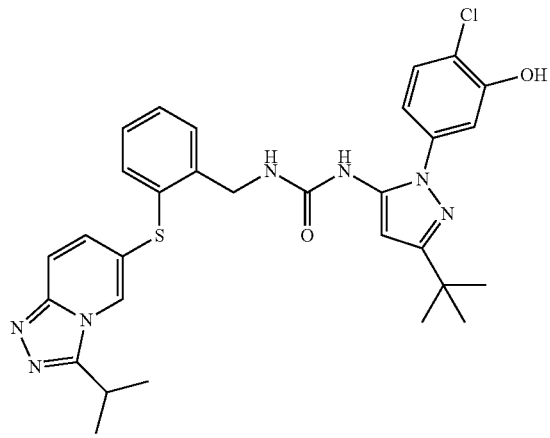 IC50 = 0.8 nM |
|      | 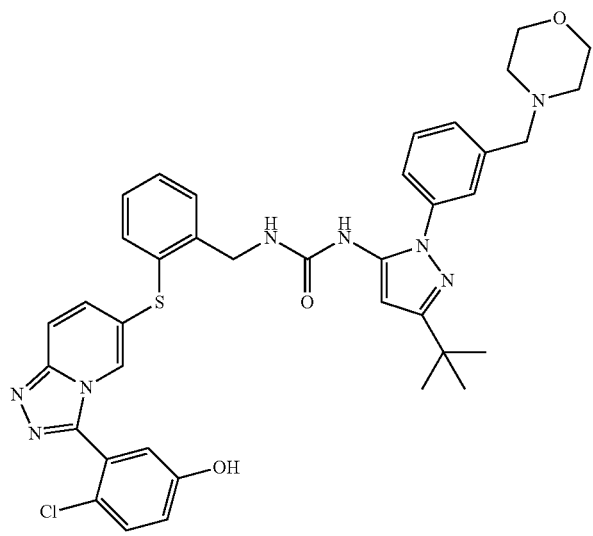 IC50 = 1.8 nM |
|      | 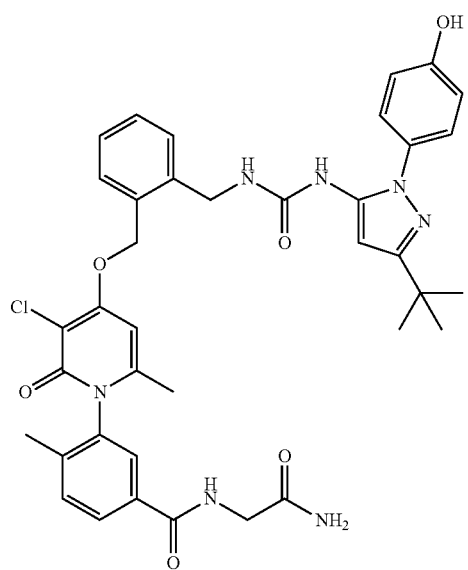 [SMILES: Cc1ccc(C(=O)NCC(N)=O)cc1-n1c(C)cc(OCc2ccccc2CNC(=O)Nc2cc(C(C)(C)C)nn2-c2ccc(O)cc2)c(Cl)c1=O] |

TABLE 1-continued
Inhibitors of Mapk14 activity
| name | Chemical name or structure |
|------|---------------------------|
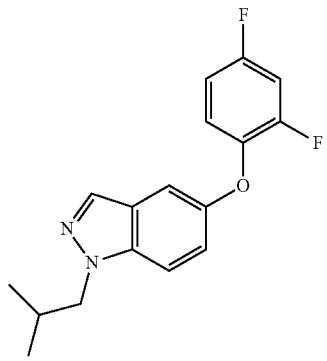
IC50 = 45 nM
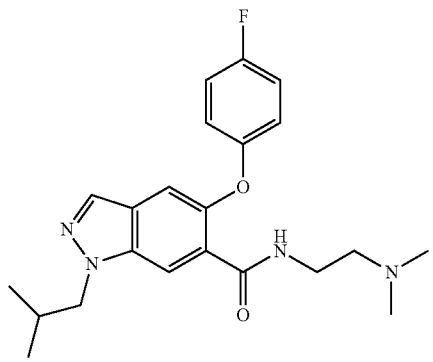
IC50 = 27 nM
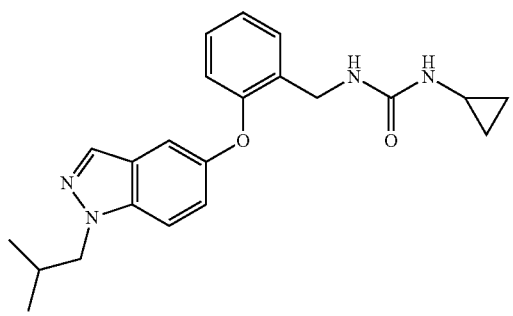
IC50 = 12 nM TABLE 1-continued
Inhibitors of Mapk14 activity
| name | Chemical name or structure |
|---|---|
| | 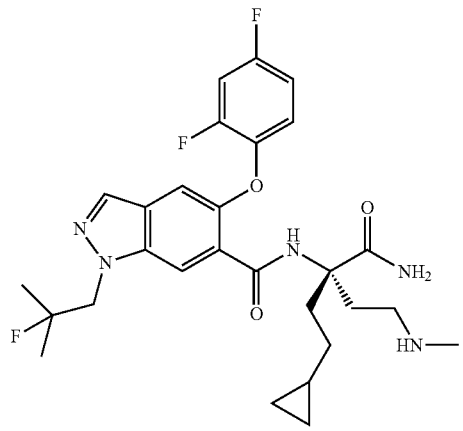<br>IC50 < 20 nM |
| RPR203494 | 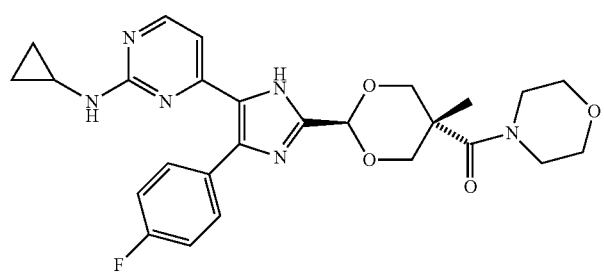 |
| | 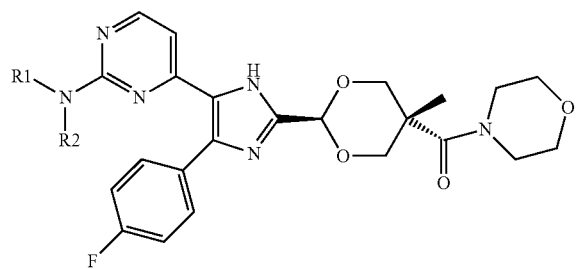 |
| R1 | R2 |
|---|---|
| Methyl | H |
| Methyl | Methyl |
| Cyclopropyl | H |
| Cyclohexyl | H |
| —CH$_2$—(CH$_2$)$_3$—CH$_2$— | |
| Carboxymethyl | H |
| Carboxyethyl | H |
| Aminoethyl | H |
| N,N-Dimethylaminoethyl | H |
| N,N-Dimethylaminopropyl | H |

TABLE 1-continued

Inhibitors of Mapk14 activity

| name | Chemical name or structure | | |
|---|---|---|---|
| | Hydroxyethyl | H | |
| | Hydroxypropyl | H | |
| | 3-Methoxypropyl | H | |
| | H | H | |
| | Allyl | H | |
| | Cyclopropylmethyl | H | |
| | Cyanoethyl | H | |
| | Propyl | H | |
| | Benzyl | H | |
| | 2-Thienyl-methyl | H | |
| | (R)-α-Methyl-benzyl | H | |
| | (S)-α-Methyl-benzyl | H | |
| | 2-Pyridyl-methyl | H | |
| | 2-Methoxybenzyl | H | |
| | 4-Fluorobenzyl | H | |
| | Phenyl | H | |
| | 3-Pyridinyl | H | |
| | 4-Pyridinyl | H | |
| | 3-Methoxyphenyl | H | |
| ARRY 797 | IC50 < 5 nM | | |
| ARRY-371797 | | | |
| ARRY-614 | | | |
| ARQ 101 | | | |
| AR00182263 | | | |
| AZD6703 | | | |
| RPR200765A | | | |
| RPR203494 | trans-N-cyclopropyl-4-[4-(4-fluorophenyl)-2-[5-methyl-5-(4-morpholinylcarbonyl)-1,3-dioxan-2-yl]-1H-imidazol-5-yl]pyrimidin-2-amine, IC50 = 9 nM | | |
| R04402257 | | | |
| 803201195 | | | |
| KC706 | | | |
| SC-80036 | | | |
| SCI-496 | | | |
| SX001 | IC50 = 9 nM | | |
| Semapimod | | | |

103 104
TABLE 1-continued
Inhibitors of Mapk14 activity
| name | Chemical name or structure |
|---|---|
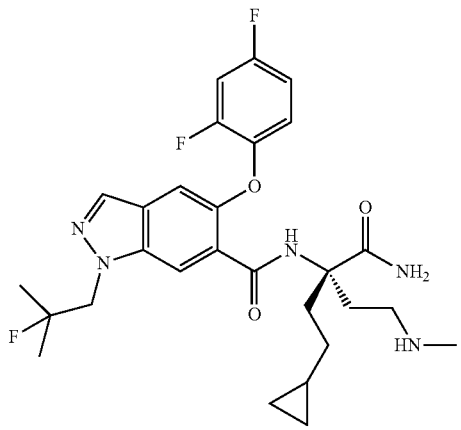
IC50 < 20 nM
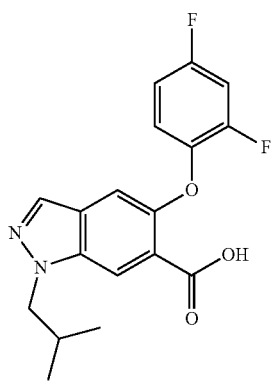
IC50 < 20 nM
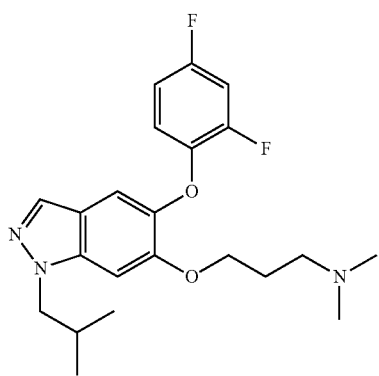
IC50 < 20 nM TABLE 1-continued
Inhibitors of Mapk14 activity
| name | Chemical name or structure |
|------|---------------------------|
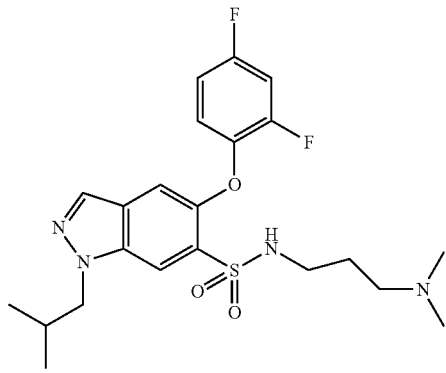
IC50 < 20 nM
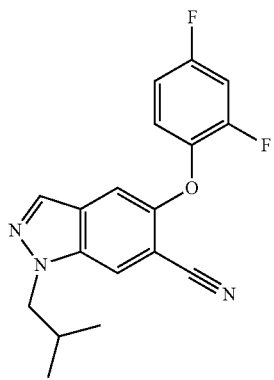 [SMILES: CC(C)Cn1ncc2cc(Oc3ccc(F)cc3F)c(C#N)cc21]
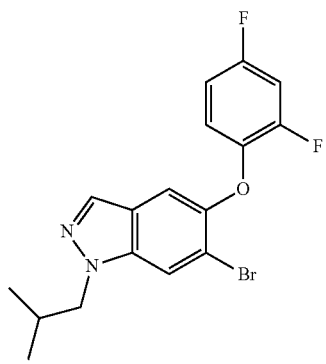 [SMILES: CC(C)Cn1ncc2cc(Oc3ccc(F)cc3F)c(Br)cc21]
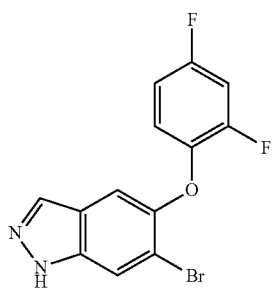 [SMILES: Fc1ccc(Oc2cc3cn[nH]c3cc2Br)c(F)c1]

TABLE 1-continued
Inhibitors of Mapk14 activity
| name | Chemical name or structure |
|---|---|
| | 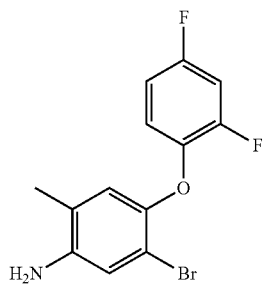 |
| | 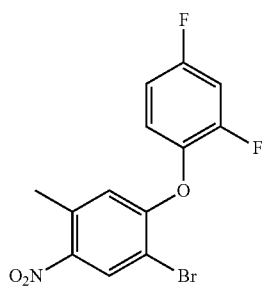 [SMILES: Cc1cc(Oc2ccc(F)cc2F)c(Br)cc1[N+](=O)[O-]] |
| | 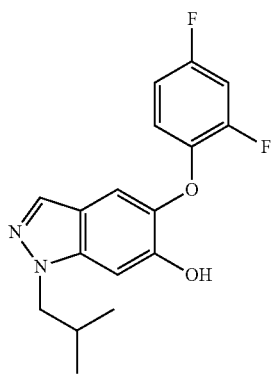 [SMILES: CC(C)Cn1ncc2cc(Oc3ccc(F)cc3F)c(O)cc21] |
| | 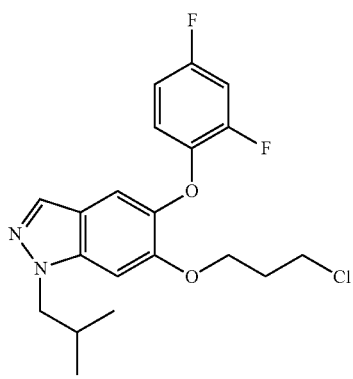 [SMILES: CC(C)Cn1ncc2cc(Oc3ccc(F)cc3F)c(OCCCCl)cc21] |

TABLE 1-continued
Inhibitors of Mapk14 activity
| name | Chemical name or structure |
|------|----------------------------|
|      | 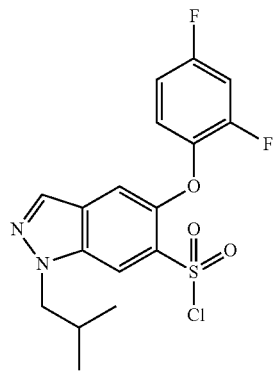 [SMILES: CC(C)Cn1ncc2cc(Oc3ccc(F)cc3F)c(S(=O)(=O)Cl)cc21]       |
|      | 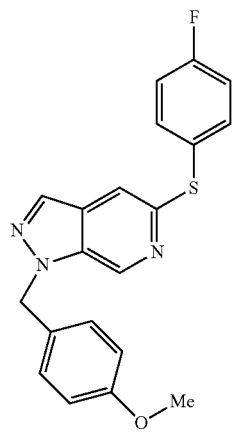 [SMILES: COc1ccc(Cn2ncc3cc(Sc4ccc(F)cc4)ncc32)cc1]       |
|      | 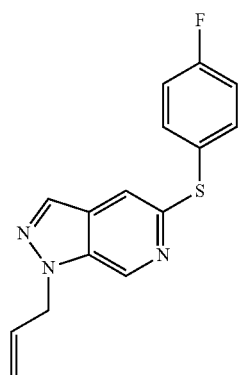 [SMILES: C=CCn1ncc2cc(Sc3ccc(F)cc3)ncc21]       |
|      | 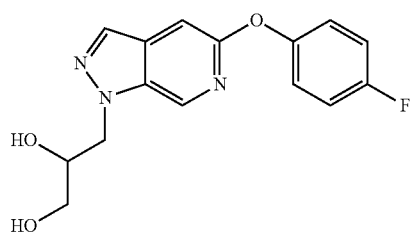 [SMILES: OCC(O)Cn1ncc2cc(Oc3ccc(F)cc3)ncc21]       |

TABLE 1-continued

Inhibitors of Mapk14 activity

| name | Chemical name or structure |
|---|---|
| | |
| 7b | 7b1: R = CH$_2$CH=CH$_2$<br>7b2: R = CH$_2$CH$_2$CH$_2$NMe$_2$<br>7b3: R = CH$_2$CH$_2$CH$_2$NHBoc |
| | |

TABLE 1-continued
Inhibitors of Mapk14 activity
| name | Chemical name or structure |
|---|---|
| | 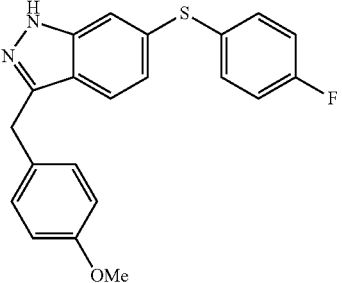 [SMILES: COc1ccc(Cc2n[nH]c3cc(Sc4ccc(F)cc4)ccc23)cc1] |
| | 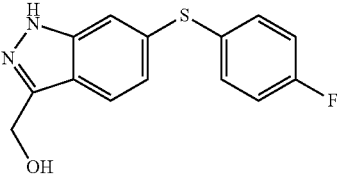 [SMILES: OCc1n[nH]c2cc(Sc3ccc(F)cc3)ccc12] |
| | 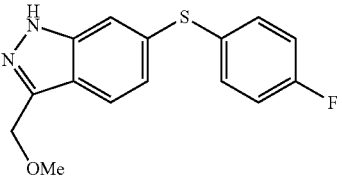 [SMILES: COCc1n[nH]c2cc(Sc3ccc(F)cc3)ccc12] |
| | 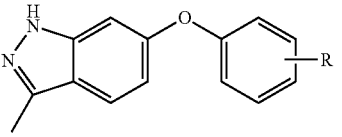<br>18c<br>18c-1: R = 4-Cl<br>18c-2: R = 4-F<br>18c-3: R = 3-Me<br>18c-4: R = 3-F<br>18c-5: R = 3-Cl<br>18c-6: R = 3-SMe<br>18c-7: R = 3-SO$_2$Me<br>18c-8: R = 3-Me, 4-F |
| | 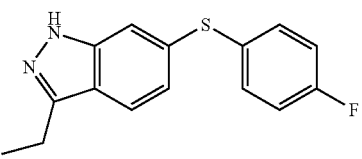 [SMILES: CCc1n[nH]c2cc(Sc3ccc(F)cc3)ccc12] |
| | 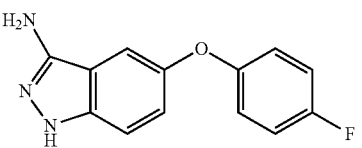 [SMILES: Nc1n[nH]c2ccc(Oc3ccc(F)cc3)cc12] |

TABLE 1-continued
Inhibitors of Mapk14 activity
| name | Chemical name or structure |
|---|---|
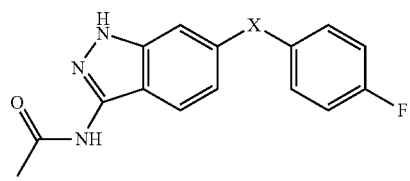
38c
38c-1: X = O
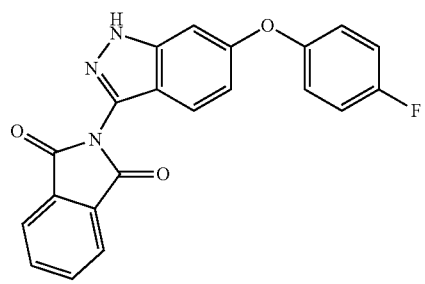 [SMILES: O=C1c2ccccc2C(=O)N1c1n[nH]c2cc(Oc3ccc(F)cc3)ccc12]
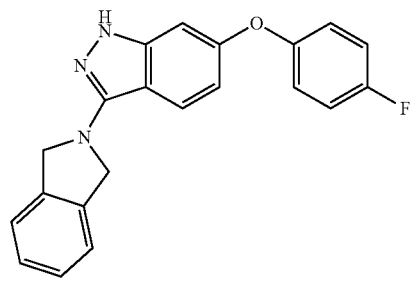 [SMILES: Fc1ccc(Oc2ccc3c(N4Cc5ccccc5C4)n[nH]c3c2)cc1]
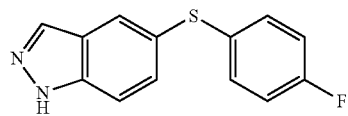 [SMILES: Fc1ccc(Sc2ccc3[nH]ncc3c2)cc1]
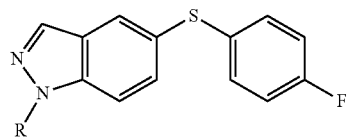
R = CHCH₃CH₃
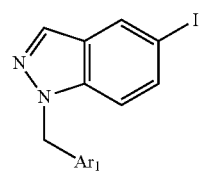
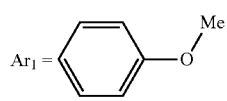

TABLE 1-continued
Inhibitors of Mapk14 activity
| name | Chemical name or structure |
|---|---|
| | 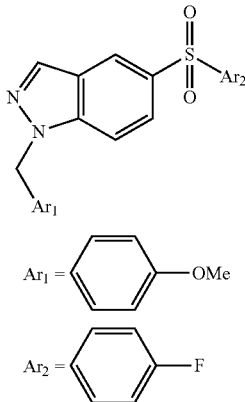 |
| | 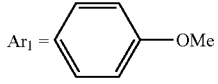 |
| | 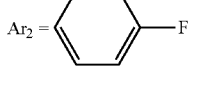 |
| 8e | 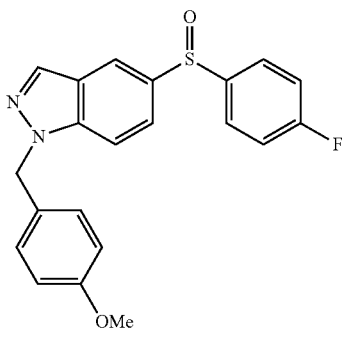 [SMILES: COc1ccc(Cn2ncc3cc(S(=O)c4ccc(F)cc4)ccc32)cc1]  8e-1: $Ar_2$ = Ph |
| 9e | 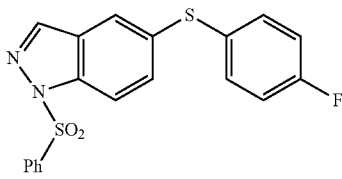 [SMILES: O=S(=O)(c1ccccc1)n1ncc2cc(Sc3ccc(F)cc3)ccc21]  9e-1: $Ar_1$ = Ph    $Ar_2$ = Ph |

TABLE 1-continued

Inhibitors of Mapk14 activity

| name | Chemical name or structure |
|------|----------------------------|

10e 10e-1: Ar₁ = 4-MeO—Ph
Ar₂ = Ph

7f 7f-1: R₁ = CH₂CH(CH₃)₂, R₂ = H, Ar = 2,4-FPh
7f-2: R₁ = CH₂CH(CH₃)₂, R₂ = H, Ar = 4-FPh
7f-3: R₁ = CH₂CH(CH₃)₂, R₂ = Et, Ar = 2,4-FPh
7f-4: R₁ = CH₂CH(CH₃)₂, R₂ = Et, Ar = 4-FPh
7f-5: R₁ = CH₂CH(CH₃)₂, R₂ = CH₂CH₂NHBoc, Ar = 2,4-FPh
7f-6: R₁ = CH₂CH(CH₃)₂, R₂ = CH₂CH₂NHBoc, Ar = 4-FPh
7f-7: R₁ = CH₂CH(CH₃)₂, R₂ = CH₂PH, Ar = 2,4-FPh
7f-8: R₁ = CH₂CH(CH₃)₂, R₂ = CH₂CH₂NH₂, Ar = 2,4-FPh
7f-9: R₁ = CH₂CH(CH₃)₂, R₂ = Me, Ar = 4-FPh
7f-10: R₁ = CH₂CH(CH₃)₂, R₂ = CH₂CH₂NH, Ar = 4-FPh

|       | R1           | R2   | Ar     |
|-------|--------------|------|--------|
| 7f-11 | CH₃          | CH₃  | 2,4 FPh |
| 7f-12 | CH₂CF₃       | H    | 2,4 FPh |
| 7f-13 | CH₂CF₃       | CH₃  | 2,4 FPh |
| 7f-14 | SO₂Me        | H    | 2,4 FPh |
| 7f-15 | SO₂Me        | CH₃  | 2,4 FPh |
| 7f-16 | H            | CH₃  | 2,4 FPh |
| 7f-17 | CH₂CH=CH₂    | H    | 2,4 FPh |
| 7f-18 | CH₂CH=CH₂    | CH₃  | 2,4 FPh |

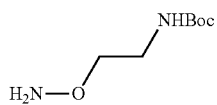

TABLE 1-continued
Inhibitors of Mapk14 activity
| name | Chemical name or structure |
|---|---|
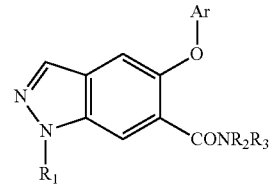
11g
| | R₁ | NR₂R₃ |
|---|---|---|
| 11g-1: | CH₂CH(CH₃)₃ | NH₂ |
| 11g-2: | CH₂CH(CH₃)₃ |  |
| 11g-3: | CH₂CH(CH₃)₃ |  |
| 11g-4: | CH₂CH(CH₃)₃ | 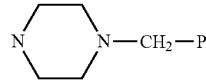 |
| 11g-5: | CH₂CH(CH₃)₃ | 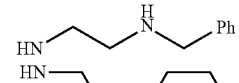 |
| 11g-6: | CH₂CH(CH₃)₃ | 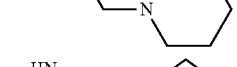 |
| 11g-7: | CH₂CH(CH₃)₃ |  |
| 11g-8: | CH₂CH(CH₃)₃ | 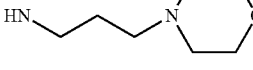 |
| 11g-9: | CH₂CH(CH₃)₃ | 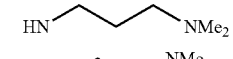 |
| 11g-10: | CH₂CH(CH₃)₃ | 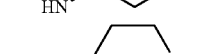 |
| 11g-11: | CH₂CH(CH₃)₃ | 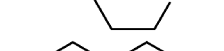 |
| 11g-12: | CH₂CH(CH₃)₃ | 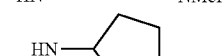 |
| 11g-13: | CH₂CH(CH₃)₃ | 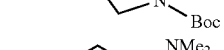 |
| 11g-14: | CH₂CF₃ | 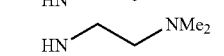 |
| 11g-15: | CH₃ | 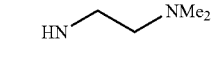 |
| 11g-16: | H |  |

TABLE 1-continued

Inhibitors of Mapk14 activity

| name | Chemical name or structure |
|---|---|

4f 4f-1: $R_1$ = $CH_2CH(CH_3)_2$, Ar = 2,4-FPh
4f-2: $R_1$ = $CH_2CH(CH_3)_2$, Ar = 4-FPh
4f-7: $R_1$ = $CH_2CH(CH_3)_2$, Ar = 2-F, 4-ClPh
4f-8: $R_1$ = $CH_2CH(CH_3)_2$, Ar = 2-Cl, 4-FPh
4f-9: $R_1$ = $CH_2CH(CH_3)_2$, Ar = 2,4-ClPh
4f-10: $R_1$ = $CH_2CH(CH_3)_2$, Ar = 2-MePh

5f 5f-1: R = $CH_2CH(CH_3)_2$, Ar = 2,4-FPh
5f-2: R = $CH_2CH(CH_3)_2$, Ar = 4-FPh
5f-7: R = $CH_2CH(CH_3)_2$, Ar = 2-F, 4-ClPh
5f-8: R = $CH_2CH(CH_3)_2$, Ar = 2-Cl, 4-FPh
5f-9: R = $CH_2CH(CH_3)_2$, Ar = 2,4-ClPh
5f-10: R = $CH_2CH(CH_3)_2$, Ar = 2-MePh
5f-11: R = $CH_2CF_3$, Ar = 2,4 FPh
5f-12: R = $CH_2CH=CH_2$, Ar = 2,4 FPh

2h 2h-1: $R_1$ = $CH_2CH(CH_3)_2$, Ar = 2,4-FPh
2h-2: $R_1$ = $CH_2CH(CH_3)_2$, Ar = 4-FPh
2h-9: $R_1$ = $CH_2CH(CH_3)_2$, Ar = 2,4-ClPh
2h-10: $R_1$ = $CH_2CH(CH_3)_2$, Ar = 2-MePh

TABLE 1-continued
Inhibitors of Mapk14 activity
| name | Chemical name or structure |
|---|---|
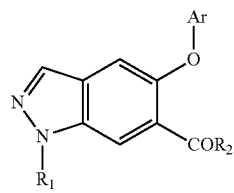
1j
| | R1 | R2 | Ar |
|---|---|---|---|
| 1j-1: | H | HN—CH(CO$_2$Me)—CH$_2$CH$_2$—NHBoc | 4-FPh |
| 1j-2: | H | HN—CH(CO$_2$Me)—CH$_2$CH$_2$—NH$_2$ | 4-FPh |
| 1j-3: | CH$_2$CF$_3$ | HN—CH(CO$_2$Me)—CH$_2$CH$_2$—NHBoc | 4-FPh |
| 1j-4: | CH$_2$CF$_3$ | HN—CH(CO$_2$Me)—CH$_2$CH$_2$—NH$_2$ | 4-FPh |
| 1j-5: | CH$_3$ | HN—CH(CO$_2$Me)—CH$_2$CH$_2$—NHBoc | 4-FPh |
| 1j-6: | CH$_3$ | HN—CH(CO$_2$Me)—CH$_2$CH$_2$—NH$_2$ | 4-FPh |
| 1j-7: | CH$_2$CH(CH$_3$)$_2$ | HN—CH(CO$_2$Me)—CH$_2$CH$_2$—NHBoc | 4-FPh |

TABLE 1-continued

Inhibitors of Mapk14 activity

| name | Chemical name or structure |
|------|----------------------------|

1k

| | R₁ | R₂ | R₃ |
|---|----|----|----|
| 1k-1: | CH₂CH(CH₃)₂ | H | ⁓⁓NMe₂ |
| 1k-2: | CH₂CH(CH₃)₂ | SO₂CH₃ | ⁓⁓NMe₂ |
| 1k-3: | CH₂CH(CH₃)₂ | (C=O)CH₃ | ⁓⁓NMe₂ |

1m 1m-1: R₁ = CH₂CH(CH₃)₂

TABLE 1-continued
Inhibitors of Mapk14 activity
| name | Chemical name or structure |
|------|----------------------------|
|  | 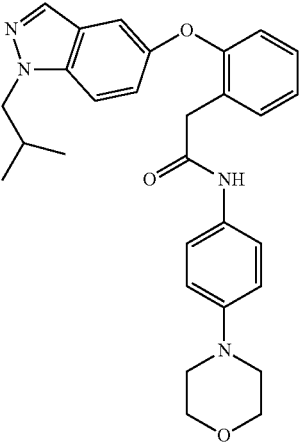 [SMILES: CC(C)Cn1ncc2cc(Oc3ccccc3CC(=O)Nc3ccc(N4CCOCC4)cc3)ccc21] |
|  | 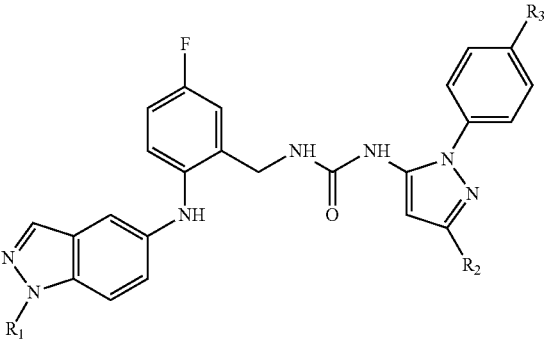<br>9q-1: $R_1$ = $CH_3$; $R_2$ = cyclopropyl; $R_3$ = $CF_3$<br>9q-2: $R_1$ = cyclobutylmethyl; $R_2$ = tBu; $R_3$ = $CH_3$ |
|  | 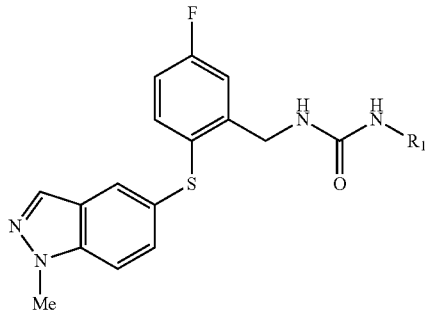<br>6r-1: $R_1$ = 5-cyclopropyl-2-(4′-chlorophenyl)-2H-pyrazol-3-yl<br>6r-2: $R_1$ = 5-t-Butyl-2-(4′-chlorophenyl)-2H-pyrazol-3-yl |
|  | 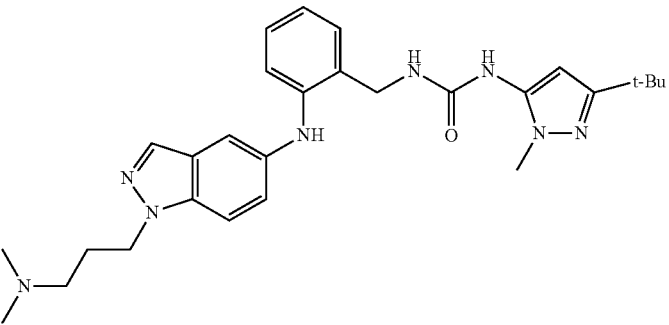 [SMILES: CN(C)CCCn1ncc2cc(Nc3ccccc3CNC(=O)Nc3cc(C(C)(C)C)nn3C)ccc21] |

TABLE 1-continued
Inhibitors of Mapk14 activity
| name | Chemical name or structure |
|------|----------------------------|
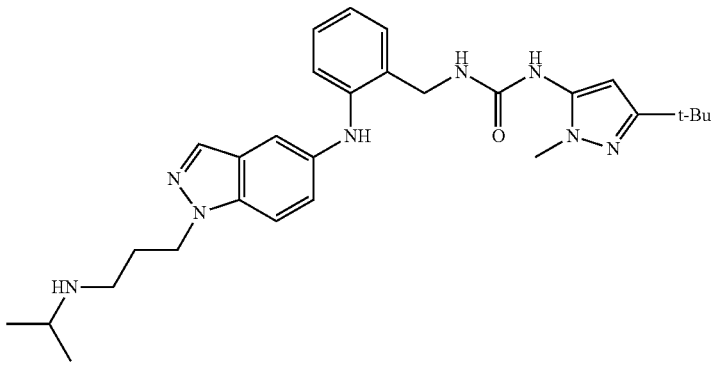 [SMILES: CC(C)NCCCn1ncc2cc(Nc3ccccc3CNC(=O)Nc3cc(C(C)(C)C)nn3C)ccc21]
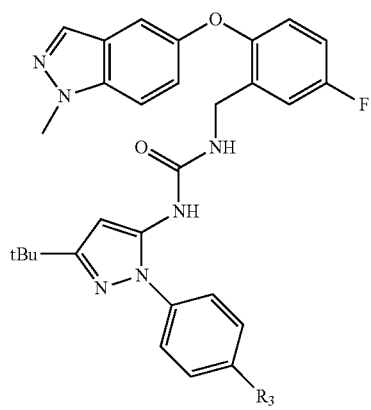
7t-1: R$_3$ = CH$_3$
7t-2: R$_3$ = Cl
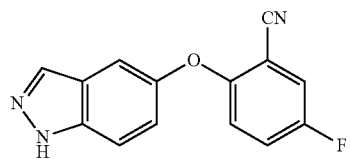 [SMILES: N#Cc1cc(F)ccc1Oc1ccc2[nH]ncc2c1]
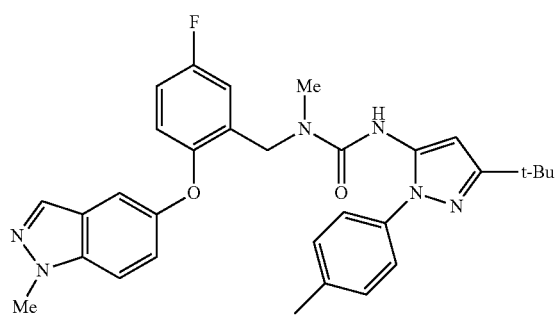 [SMILES: Cc1ccc(-n2nc(C(C)(C)C)cc2NC(=O)N(C)Cc2cc(F)ccc2Oc2ccc3c(cnn3C)c2)cc1]

TABLE 1-continued

Inhibitors of Mapk14 activity

| name | Chemical name or structure |
|------|---------------------------|

7v: R = CH₃

8v: R = —C₆H₄—CH₃ (p-tolyl)

TABLE 1-continued

Inhibitors of Mapk14 activity

| name | Chemical name or structure |
|---|---|

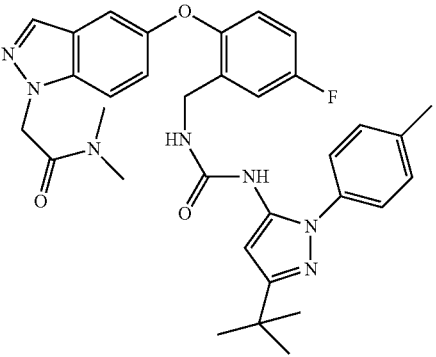

IC50 < 20 nM

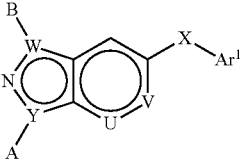

wherein is Y is C, N;
W is C, N, S, or O, provided that W is N, S, or O when Y is C, and W is C or N when Y is N;
U is CH or N;
V is C-E or N;
X is O, S, SO, $SO_2$, $NR^7$, C=O, $CHR^7$, —C=$NOR^1$, —C=$CHR^1$, or $CHOR^1$;
$Ar^1$ is substituted or unsubstituted aryl or heteroaryl;
B is H, $NH_2$, or substituted or unsubstituted methyl;
A is H, OH, an amine protecting group, $Z_n$—$NR^2R^3$, $Z_n$—$NR^2(C=O)R^2$, $Z_n$—$SO_2R^2$, $Z_n$—$SOR^2$, $Z_n$—$SR^2$, $Z_n$—$OR^2$, $Z_n$—(C=O)$R^2$, $Z_n$—(C=O)$OR^2$, $Z_n$—O—(C=O)$R^2$, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted;
n is 0 or 1,

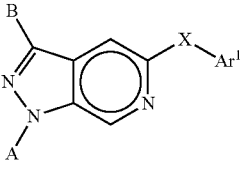

X is O, S, SO, $SO_2$, $NR^7$, C=O, $CHR^7$, —C=$NOR^1$, —C=$CHR^1$, or $CHOR^1$;
B is H, $NH_2$, or substituted or unsubstituted methyl;
A is H, OH, an amine protecting group, $Z_n$—$NR^2R^3$, $Z_n$—$NR^2(C=O)R^2$, $Z_n$—$SO_2R^2$, $Z_n$—$SOR^2$, $Z_n$—$SR^2$, $Z_n$—$OR^2$, $Z_n$—(C=O)$R^2$, $Z_n$—(C=O)$OR^2$, $Z_n$—O—(C=O)$R^2$, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted;
$R^2$ and $R^3$ are independently H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted, or $R^2$ together with $R^3$ and N forms a saturated or partially unsaturated heterocycle having 1 or more heteroatoms, wherein said heterocycle may be substituted or unsubstituted and wherein said heterocycle may be fused to an aromatic ring;
Z is alkylene having from 1 to 4 carbons, or alkenylene or alkynylene each having from 2 to 4 carbons, wherein said alkylene, alkenylene, or alkynylene may be substituted or unsubstituted;
$Ar^1$ is substituted or unsubstituted aryl or heteroaryl;
n is 0 or 1, TABLE 1-continued Inhibitors of Mapk14 activity

| name | Chemical name or structure |
|---|---|
| | 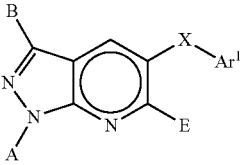 |

X is O, S, SO, $SO_2$, $NR^7$, C=O, $CHR^7$, —C=$NOR^1$, —C=$CHR^1$, or $CHOR^1$;
B is H, $NH_2$, or substituted or unsubstituted methyl;
A is H, OH, an amine protecting group, $Z_n$—$NR^2R^3$, $Z_n$—$NR^2(C=O)R^2$, $Z_n$—$SO_2R^2$, $Z_n$—$SOR^2$, $Z_n$—$SR^2$, $Z_n$—$OR^2$, $Z_n$—(C=O)$R^2$, $Z_n$—(C=O)$OR^2$, $Z_n$—O—(C=O)$R^2$, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted;
$R^2$ and $R^3$ are independently H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted, or $R^2$ together with $R^3$ and N forms a saturated or partially unsaturated heterocycle having 1 or more heteroatoms, wherein said heterocycle may be substituted or unsubstituted and wherein said heterocycle may be fused to an aromatic ring;
Z is alkylene having from 1 to 4 carbons, or alkenylene or alkynylene each having from 2 to 4 carbons, wherein said alkylene, alkenylene, or alkynylene may be substituted or unsubstituted;
$Ar^1$ is substituted or unsubstituted aryl or heteroaryl;
E is H, $Z_n$—$NR^2R^3$, $Z_n$—(C=O)$R^4$, $Z_n$—(C=O)$R^5$, $Z_n$—$NR^5(C=O)R^5$, $Z_n$—O(C=O)$R^5$, $Z_n$—$OR^5$, $Z_n$—$SO_2R^5$, $Z_n$—$SOR^5$, $Z_n$—$SR^5$, $Z_n$—NH(C=O)$NHR^5$, or $R^5$;
$R^4$ is a substituted or unsubstituted natural or unnatural amino acid, a protected natural or unnatural amino acid, $NH(CHR^6)(CH_2)_mOR^5$ where m is an integer from 1 to 4, or $NR^2R^3$;
$R^5$ is H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted;
n is 0 or 1,

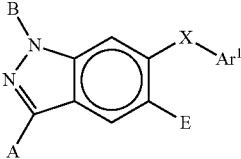

X is O, S, SO, $SO_2$, $NR^7$, C=O, $CHR^7$, —C=$NOR^1$, —C=$CHR^1$, or $CHOR^1$;
B is H, $NH_2$, or substituted or unsubstituted methyl;
A is H, OH, an amine protecting group, $Z_n$—$NR^2R^3$, $Z_n$—$NR^2(C=O)R^2$, $Z_n$—$SO_2R^2$, $Z_n$—$SOR^2$, $Z_n$—$SR^2$, $Z_n$—$OR^2$, $Z_n$—(C=O)$R^2$, $Z_n$—(C=O)$OR^2$, $Z_n$—O—(C=O)$R^2$, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted;
$R^2$ and $R^3$ are independently H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted, or $R^2$ together with $R^3$ and N forms a saturated or partially unsaturated heterocycle having 1 or more heteroatoms, wherein said heterocycle may be substituted or unsubstituted and wherein said heterocycle may be fused to an aromatic ring;
Z is alkylene having from 1 to 4 carbons, or alkenylene or alkynylene each having from 2 to 4 carbons, wherein said alkylene, alkenylene, or alkynylene may be substituted or unsubstituted;
$Ar^1$ is substituted or unsubstituted aryl or heteroaryl;
E is H, $Z_n$—$NR^2R^3$, $Z_n$—(C=O)$R^4$, $Z_n$—(C=O)$R^5$, $Z_n$—$NR^5(C=O)R^5$, $Z_n$—O(C=O)$R^5$, $Z_n$—$OR^5$, $Z_n$—$SO_2R^5$, $Z_n$—$SOR^5$, $Z_n$—$SR^5$, $Z_n$—NH(C=O)$NHR^5$, or $R^5$;
$R^4$ is a substituted or unsubstituted natural or unnatural amino acid, a protected natural or unnatural amino acid, $NH(CHR^6)(CH_2)_mOR^5$ where m is an integer from 1 to 4, or $NR^2R^3$;
$R^5$ is H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted;
n is 0 or 1, TABLE 1-continued Inhibitors of Mapk14 activity

| name | Chemical name or structure |
|---|---| where A, B, X, E and $Ar^1$ are as defined above, provided that when B is H and A is $CH=CH-R^8$ where $R^8$ is a substituted or unsubstituted alkyl, alkenyl, cycloalkyl, heterocycloalkyl, aryl, or heteroaryl, then $X-Ar^1$ is a substituent where $Ar^1$ is other than substituted or unsubstituted aryl, heteroaryl, NH-alkyl, NH-cycloalkyl, NH-heterocycloalkyl, NH-aryl, NH-heteroaryl, NH-alkoxy, or NH-dialkylamide when X is O, S, C=O, S=O, $C=CH_2$, $CO_2$, NH, or $N(C_1-C_8\text{-alkyl})$.

[Chemical structure: benzisoxazole with substituents A, X-$Ar^1$, E]

X is O, S, SO, $SO_2$, $NR^7$, C=O, $CHR^7$, $-C=NOR^1$, $-C=CHR^1$, or $CHOR^1$;
A is H, OH, an amine protecting group, $Z_n-NR^2R^3$, $Z_n-NR^2(C=O)R^2$, $Z_n-SO_2R^2$, $Z_n-SOR^2$, $Z_n-SR^2$, $Z_n-OR^2$, $Z_n-(C=O)R^2$, $Z_n-(C=O)OR^2$, $Z_n-O-(C=O)R^2$, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n-Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n-Ar^1$ may be substituted or unsubstituted;
$R^2$ and $R^3$ are independently H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n-Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n-Ar^1$ may be substituted or unsubstituted, or $R^2$ together with $R^3$ and N forms a saturated or partially unsaturated heterocycle having 1 or more heteroatoms, wherein said heterocycle may be substituted or unsubstituted and wherein said heterocycle may be fused to an aromatic ring;
Z is alkylene having from 1 to 4 carbons, or alkenylene or alkynylene each having from 2 to 4 carbons, wherein said alkylene, alkenylene, or alkynylene may be substituted or unsubstituted;
$Ar^1$ is substituted or unsubstituted aryl or heteroaryl;
E is H, $Z_n-NR^2R^3$, $Z_n-(C=O)R^4$, $Z_n-(C=O)R^5$, $Z_n-NR^5(C=O)R^5$, $Z_n-O(C=O)R^5$, $Z_n-OR^5$, $Z_n-SO_2R^5$, $Z_n-SOR^5$, $Z_n-SR^5$, $Z_n-NH(C=O)NHR^5$, or $R^5$;
$R^4$ is a substituted or unsubstituted natural or unnatural amino acid, a protected natural or unnatural amino acid, $NH(CHR^6)(CH_2)_mOR^5$ where m is an integer from 1 to 4, or $NR^2R^3$;
$R^5$ is H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n-Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n-Ar^1$ may be substituted or unsubstituted;
n is 0 or 1,

[Chemical structure: indazole with substituents B, A, O-$Ar^1$, E]

B is H, $NH_2$, or substituted or unsubstituted methyl;
A is H, OH, an amine protecting group, $Z_n-NR^2R^3$, $Z_n-NR^2(C=O)R^2$, $Z_n-SO_2R^2$, $Z_n-SOR^2$, $Z_n-SR^2$, $Z_n-OR^2$, $Z_n-(C=O)R^2$, $Z_n-(C=O)OR^2$, $Z_n-O-(C=O)R^2$, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n-Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n-Ar^1$ may be substituted or unsubstituted;
$R^2$ and $R^3$ are independently H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n-Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n-Ar^1$ may be substituted or unsubstituted, or $R^2$ together with $R^3$ and N forms a saturated or partially unsaturated heterocycle having 1 or more heteroatoms, wherein said heterocycle may be substituted or unsubstituted and wherein said heterocycle may be fused to an aromatic ring;
Z is alkylene having from 1 to 4 carbons, or alkenylene or alkynylene each having from 2 to 4 carbons, wherein said alkylene, alkenylene, or alkynylene may be substituted or unsubstituted;
$Ar^1$ is substituted or unsubstituted aryl or heteroaryl;
E is H, $Z_n-NR^2R^3$, $Z_n-(C=O)R^4$, $Z_n-(C=O)R^5$, $Z_n-NR^5(C=O)R^5$, $Z_n-O(C=O)R^5$, $Z_n-OR^5$, $Z_n-SO_2R^5$, $Z_n-SOR^5$, $Z_n-SR^5$, $Z_n-NH(C=O)NHR^5$, or $R^5$;
$R^4$ is a substituted or unsubstituted natural or unnatural amino acid, a protected natural or unnatural amino acid, $NH(CHR^6)(CH_2)_mOR^5$ where m is an integer from 1 to 4, or $NR^2R^3$;
$R^5$ is H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n-Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n-Ar^1$ may be substituted or unsubstituted;
n is 0 or 1, TABLE 1-continued Inhibitors of Mapk14 activity

| name | Chemical name or structure |
|---|---|

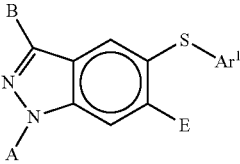

B is H, $NH_2$, or substituted or unsubstituted methyl;
A is H, OH, an amine protecting group, $Z_n$—$NR^2R^3$, $Z_n$—$NR^2(C$=$O)R^2$, $Z_n$—$SO_2R^2$, $Z_n$—$SOR^2$, $Z_n$—$SR^2$, $Z_n$—$OR^2$, $Z_n$—(C=O)$R^2$, $Z_n$—(C=O)$OR^2$, $Z_n$—O—(C=O)$R^2$, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted;
$R^2$ and $R^3$ are independently H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted, or $R^2$ together with $R^3$ and N forms a saturated or partially unsaturated heterocycle having 1 or more heteroatoms, wherein said heterocycle may be substituted or unsubstituted and wherein said heterocycle may be fused to an aromatic ring;
Z is alkylene having from 1 to 4 carbons, or alkenylene or alkynylene each having from 2 to 4 carbons, wherein said alkylene, alkenylene, or alkynylene may be substituted or unsubstituted;
$Ar^1$ is substituted or unsubstituted aryl or heteroaryl;
E is H, $Z_n$—$NR^2R^3$, $Z_n$—(C=O)$R^4$, $Z_n$—(C=O)$R^5$, $Z_n$—$NR^5(C$=$O)R^5$, $Z_n$—O(C=O)$R^5$, $Z_n$—$OR^5$, $Z_n$—$SO_2R^5$, $Z_n$—$SOR^5$, $Z_n$—$SR^5$, $Z_n$—NH(C=O)$NHR^5$, or $R^5$;
$R^4$ is a substituted or unsubstituted natural or unnatural amino acid, a protected natural or unnatural amino acid, $NH(CHR^6)(CH_2)_mOR^5$ where m is an integer from 1 to 4, or $NR^2R^3$;
$R^5$ is H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted;
n is 0 or 1,

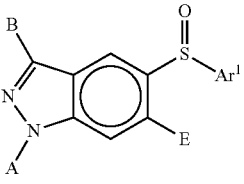

B is H, $NH_2$, or substituted or unsubstituted methyl;
A is H, OH, an amine protecting group, $Z_n$—$NR^2R^3$, $Z_n$—$NR^2(C$=$O)R^2$, $Z_n$—$SO_2R^2$, $Z_n$—$SOR^2$, $Z_n$—$SR^2$, $Z_n$—$OR^2$, $Z_n$—(C=O)$R^2$, $Z_n$—(C=O)$OR^2$, $Z_n$—O—(C=O)$R^2$, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted;
$R^2$ and $R^3$ are independently H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted, or $R^2$ together with $R^3$ and N forms a saturated or partially unsaturated heterocycle having 1 or more heteroatoms, wherein said heterocycle may be substituted or unsubstituted and wherein said heterocycle may be fused to an aromatic ring;
Z is alkylene having from 1 to 4 carbons, or alkenylene or alkynylene each having from 2 to 4 carbons, wherein said alkylene, alkenylene, or alkynylene may be substituted or unsubstituted;
$Ar^1$ is substituted or unsubstituted aryl or heteroaryl;
E is H, $Z_n$—$NR^2R^3$, $Z_n$—(C=O)$R^4$, $Z_n$—(C=O)$R^5$, $Z_n$—$NR^5(C$=$O)R^5$, $Z_n$—O(C=O)$R^5$, $Z_n$—$OR^5$, $Z_n$—$SO_2R^5$, $Z_n$—$SOR^5$, $Z_n$—$SR^5$, $Z_n$—NH(C=O)$NHR^5$, or $R^5$;
$R^4$ is a substituted or unsubstituted natural or unnatural amino acid, a protected natural or unnatural amino acid, $NH(CHR^6)(CH_2)_mOR^5$ where m is an integer from 1 to 4, or $NR^2R^3$;
$R^5$ is H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted;
n is 0 or 1, TABLE 1-continued Inhibitors of Mapk14 activity

| name | Chemical name or structure |
|---|---|

[Structure: indazole with substituent B at 3-position, A on N1, and a sulfonyl group ($SO_2Ar^1$) on the benzene ring, with E substituent]

B is H, $NH_2$, or substituted or unsubstituted methyl;
A is H, OH, an amine protecting group, $Z_n$—$NR^2R^3$, $Z_n$—$NR^2(C=O)R^2$, $Z_n$—$SO_2R^2$, $Z_n$—$SOR^2$, $Z_n$—$SR^2$, $Z_n$—$OR^2$, $Z_n$—$(C=O)R^2$, $Z_n$—$(C=O)OR^2$, $Z_n$—O—$(C=O)R^2$, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted;
$R^2$ and $R^3$ are independently H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted, or $R^2$ together with $R^3$ and N forms a saturated or partially unsaturated heterocycle having 1 or more heteroatoms, wherein said heterocycle may be substituted or unsubstituted and wherein said heterocycle may be fused to an aromatic ring;
Z is alkylene having from 1 to 4 carbons, or alkenylene or alkynylene each having from 2 to 4 carbons, wherein said alkylene, alkenylene, or alkynylene may be substituted or unsubstituted;
$Ar^1$ is substituted or unsubstituted aryl or heteroaryl;
E is H, $Z_n$—$NR^2R^3$, $Z_n$—$(C=O)R^4$, $Z_n$—$(C=O)R^5$, $Z_n$—$NR^5(C=O)R^5$, $Z_n$—$O(C=O)R^5$, $Z_n$—$OR^5$, $Z_n$—$SO_2R^5$, $Z_n$—$SOR^5$, $Z_n$—$SR^5$, $Z_n$—$NH(C=O)NHR^5$, or $R^5$;
$R^4$ is a substituted or unsubstituted natural or unnatural amino acid, a protected natural or unnatural amino acid, $NH(CHR^6)(CH_2)_mOR^5$ where m is an integer from 1 to 4, or $NR^2R^3$;
$R^5$ is H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted;
n is 0 or 1,

[Structure: indazole with substituent B at 3-position, A on N1, and a CH(OH)$Ar^1$ group on the benzene ring, with E substituent]

B is H, $NH_2$, or substituted or unsubstituted methyl;
A is H, OH, an amine protecting group, $Z_n$—$NR^2R^3$, $Z_n$—$NR^2(C=O)R^2$, $Z_n$—$SO_2R^2$, $Z_n$—$SOR^2$, $Z_n$—$SR^2$, $Z_n$—$OR^2$, $Z_n$—$(C=O)R^2$, $Z_n$—$(C=O)OR^2$, $Z_n$—O—$(C=O)R^2$, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, Zn-heterocycloalkyl, or $Z_n$—$Ar^1$ may be substituted or unsubstituted;
$R^2$ and $R^3$ are independently H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted, or $R^2$ together with $R^3$ and N forms a saturated or partially unsaturated heterocycle having 1 or more heteroatoms, wherein said heterocycle may be substituted or unsubstituted and wherein said heterocycle may be fused to an aromatic ring;
Z is alkylene having from 1 to 4 carbons, or alkenylene or alkynylene each having from 2 to 4 carbons, wherein said alkylene, alkenylene, or alkynylene may be substituted or unsubstituted;
$Ar^1$ is substituted or unsubstituted aryl or heteroaryl;
E is H, $Z_n$—$NR^2R^3$, $Z_n$—$(C=O)R^4$, $Z_n$—$(C=O)R^5$, $Z_n$—$NR^5(C=O)R^5$, $Z_n$—$O(C=O)R^5$, $Z_n$—$OR^5$, $Z_n$—$SO_2R^5$, $Z_n$—$SOR^5$, $Z_n$—$SR^5$, $Z_n$—$NH(C=O)NHR^5$, or $R^5$;
$R^4$ is a substituted or unsubstituted natural or unnatural amino acid, a protected natural or unnatural amino acid, $NH(CHR^6)(CH_2)_mOR^5$ where m is an integer from 1 to 4, or $NR^2R^3$;
$R^5$ is H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted;
n is 0 or 1, TABLE 1-continued Inhibitors of Mapk14 activity

| name | Chemical name or structure |
| --- | --- |

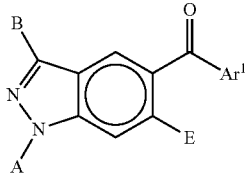

B is H, $NH_2$, or substituted or unsubstituted methyl;
A is H, OH, an amine protecting group, $Z_n$—$NR^2R^3$, $Z_n$—$NR^2(C$=$O)R^2$, $Z_n$—$SO_2R^2$, $Z_n$—$SOR^2$, $Z_n$—$SR^2$, $Z_n$—$OR^2$, $Z_n$—$(C$=$O)R^2$, $Z_n$—$(C$=$O)OR^2$, $Z_n$—$O$—$(C$=$O)R^2$, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted;
$R^2$ and $R^3$ are independently H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted, or $R^2$ together with $R^3$ and N forms a saturated or partially unsaturated heterocycle having 1 or more heteroatoms, wherein said heterocycle may be substituted or unsubstituted and wherein said heterocycle may be fused to an aromatic ring;
Z is alkylene having from 1 to 4 carbons, or alkenylene or alkynylene each having from 2 to 4 carbons, wherein said alkylene, alkenylene, or alkynylene may be substituted or unsubstituted;
$Ar^1$ is substituted or unsubstituted aryl or heteroaryl;
E is H, $Z_n$—$NR^2R^3$, $Z_n$—$(C$=$O)R^4$, $Z_n$—$(C$=$O)R^5$, $Z_n$—$NR^5(C$=$O)R^5$, $Z_n$—$O(C$=$O)R^5$, $Z_n$—$OR^5$, $Z_n$—$SO_2R^5$, $Z_n$—$SOR^5$, $Z_n$—$SR^5$, $Z_n$—$NH(C$=$O)NHR^5$, or $R^5$;
$R^4$ is a substituted or unsubstituted natural or unnatural amino acid, a protected natural or unnatural amino acid, $NH(CHR^6)(CH_2)_mOR^5$ where m is an integer from 1 to 4, or $NR^2R^3$;
$R^5$ is H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted;
n is 0 or 1,

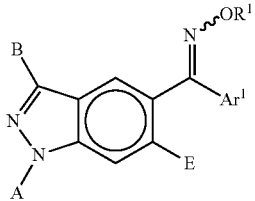

B is H, $NH_2$, or substituted or unsubstituted methyl;
A is H, OH, an amine protecting group, $Z_n$—$NR^2R^3$, $Z_n$—$NR^2(C$=$O)R^2$, $Z_n$—$SO_2R^2$, $Z_n$—$SOR^2$, $Z_n$—$SR^2$, $Z_n$—$OR^2$, $Z_n$—$(C$=$O)R^2$, $Z_n$—$(C$=$O)OR^2$, $Z_n$—$O$—$(C$=$O)R^2$, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted;
$R^2$ and $R^3$ are independently H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted, or $R^2$ together with $R^3$ and N forms a saturated or partially unsaturated heterocycle having 1 or more heteroatoms, wherein said heterocycle may be substituted or unsubstituted and wherein said heterocycle may be fused to an aromatic ring;
Z is alkylene having from 1 to 4 carbons, or alkenylene or alkynylene each having from 2 to 4 carbons, wherein said alkylene, alkenylene, or alkynylene may be substituted or unsubstituted;
$Ar^1$ is substituted or unsubstituted aryl or heteroaryl;
E is H, $Z_n$—$NR^2R^3$, $Z_n$—$(C$=$O)R^4$, $Z_n$—$(C$=$O)R^5$, $Z_n$—$NR^5(C$=$O)R^5$, $Z_n$—$O(C$=$O)R^5$, $Z_n$—$OR^5$, $Z_n$—$SO_2R^5$, $Z_n$—$SOR^5$, $Z_n$—$SR^5$, $Z_n$—$NH(C$=$O)NHR^5$, or $R^5$;
$R^4$ is a substituted or unsubstituted natural or unnatural amino acid, a protected natural or unnatural amino acid, $NH(CHR^6)(CH_2)_mOR^5$ where m is an integer from 1 to 4, or $NR^2R^3$;
$R^5$ is H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted;

TABLE 1-continued

Inhibitors of Mapk14 activity

| name | Chemical name or structure |
|---|---|

R$^1$ is H, PO$_3$H$_2$, SO$_3$H$_2$, alkyl, allyl, alkenyl, alkynyl, heteroalkyl, heteroallyl, heteroalkenyl, heteroalkynyl, alkoxy, heteroalkoxy, Z$_n$-cycloalkyl, Z$_n$-heterocycloalkyl, or Z$_n$—Ar$^1$, wherein said alkyl, allyl, alkenyl, alkynyl, heteroalkyl, heteroallyl, heteroalkenyl, heteroalkynyl, alkoxy, heteroalkoxy, Z$_n$-cycloalkyl, Z$_n$-heterocycloalkyl, or Z$_n$—Ar$^1$ may be substituted or unsubstituted;
n is 0 or 1,

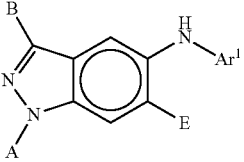

B is H, NH$_2$, or substituted or unsubstituted methyl;
A is H, OH, an amine protecting group, Z$_n$—NR$^2$R$^3$, Z$_n$—NR$^2$(C=O)R$^2$, Z$_n$—SO$_2$R$^2$, Z$_n$—SOR$^2$, Z$_n$—SR$^2$, Z$_n$—OR$^2$, Z$_n$—(C=O)R$^2$, Z$_n$—(C=O)OR$^2$, Z$_n$—O—(C=O)R$^2$, alkyl, allyl, alkenyl, alkynyl, heteroalkyl, heteroallyl, heteroalkenyl, heteroalkynyl, alkoxy, heteroalkoxy, Z$_n$-cycloalkyl, Z$_n$-heterocycloalkyl, or Z$_n$—Ar$^1$, wherein said alkyl, allyl, alkenyl, alkynyl, heteroalkyl, heteroallyl, heteroalkenyl, heteroalkynyl, alkoxy, heteroalkoxy, Z$_n$-cycloalkyl, Z$_n$-heterocycloalkyl, or Z$_n$—Ar$^1$ may be substituted or unsubstituted;
Ar$^1$ is substituted or unsubstituted aryl or heteroaryl;
R$^2$ and R$^3$ are independently H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, Z$_n$-cycloalkyl, Z$_n$-heterocycloalkyl, or Z$_n$—Ar$^1$, wherein said alkyl, allyl, alkenyl, alkynyl, heteroalkyl, heteroallyl, heteroalkenyl, heteroalkynyl, alkoxy, heteroalkoxy, Z$_n$-cycloalkyl, Z$_n$-heterocycloalkyl, or Z$_n$—Ar$^1$ may be substituted or unsubstituted, or R$^2$ together with R$^3$ and N forms a saturated or partially unsaturated heterocycle having 1 or more heteroatoms, wherein said heterocycle may be substituted or unsubstituted and wherein said heterocycle may be fused to an aromatic ring;
Z is alkylene having from 1 to 4 carbons, or alkenylene or alkynylene each having from 2 to 4 carbons, wherein said alkylene, alkenylene, or alkynylene may be substituted or unsubstituted;
Ar$^1$ is substituted or unsubstituted aryl or heteroaryl;
E is H, Z$_n$—NR$^2$R$^3$, Z$_n$—(C=O)R$^4$, Z$_n$—(C=O)R$^5$, Z$_n$—NR$^5$(C=O)R$^5$, Z$_n$—O(C=O)R$^5$, Z$_n$—OR$^5$, Z$_n$—SO$_2$R$^5$, Z$_n$—SOR$^5$, Z$_n$—SR$^5$, Z$_n$—NH(C=O)NHR$^5$, or R$^5$;
R$^4$ is a substituted or unsubstituted natural or unnatural amino acid, a protected natural or unnatural amino acid, NH(CHR$^6$)(CH$_2$)$_m$OR$^5$ where m is an integer from 1 to 4, or NR$^2$R$^3$;
R$^5$ is H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, Z$_n$-cycloalkyl, Z$_n$-heterocycloalkyl, or Z$_n$—Ar$^1$, wherein said alkyl, allyl, alkenyl, alkynyl, heteroalkyl, heteroallyl, heteroalkenyl, heteroalkynyl, alkoxy, heteroalkoxy, Z$_n$-cycloalkyl, Z$_n$-heterocycloalkyl, or Z$_n$—Ar$^1$ may be substituted or unsubstituted;
n is 0 or 1,

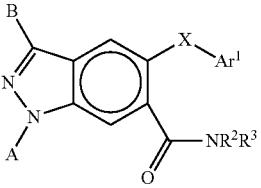

B is H, NH$_2$, or substituted or unsubstituted methyl;
A is H, OH, an amine protecting group, Z$_n$—NR$^2$R$^3$, Z$_n$—NR$^2$(C=O)R$^2$, Z$_n$—SO$_2$R$^2$, Z$_n$—SOR$^2$, Z$_n$—SR$^2$, Z$_n$—OR$^2$, Z$_n$—(C=O)R$^2$, Z$_n$—(C=O)OR$^2$, Z$_n$—O—(C=O)R$^2$, alkyl, allyl, alkenyl, alkynyl, heteroalkyl, heteroallyl, heteroalkenyl, heteroalkynyl, alkoxy, heteroalkoxy, Z$_n$-cycloalkyl, Z$_n$-heterocycloalkyl, or Z$_n$—Ar$^1$, wherein said alkyl, allyl, alkenyl, alkynyl, heteroalkyl, heteroallyl, heteroalkenyl, heteroalkynyl, alkoxy, heteroalkoxy, Z$_n$-cycloalkyl, Z$_n$-heterocycloalkyl, or Z$_n$—Ar$^1$ may be substituted or unsubstituted;
Ar$^1$ is substituted or unsubstituted aryl or heteroaryl;
R$^2$ and R$^3$ are independently H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, Z$_n$-cycloalkyl, Z$_n$-heterocycloalkyl, or Z$_n$—Ar$^1$, wherein said alkyl, allyl, alkenyl, alkynyl, heteroalkyl, heteroallyl, heteroalkenyl, heteroalkynyl, alkoxy, heteroalkoxy, Z$_n$-cycloalkyl, Z$_n$-heterocycloalkyl, or Z$_n$—Ar$^1$ may be substituted or unsubstituted, or R$^2$ together with R$^3$ and N forms a saturated or partially unsaturated heterocycle having 1 or more heteroatoms, wherein said heterocycle may be substituted or unsubstituted and wherein said heterocycle may be fused to an aromatic ring;
Z is alkylene having from 1 to 4 carbons, or alkenylene or alkynylene each having from 2 to 4 carbons, wherein said alkylene, alkenylene, or alkynylene may be substituted or unsubstituted;
Ar$^1$ is substituted or unsubstituted aryl or heteroaryl;
R$^4$ is a substituted or unsubstituted natural or unnatural amino acid, a protected natural or unnatural amino acid, NH(CHR$^6$)(CH$_2$)$_m$OR$^5$ where m is an integer from 1 to 4, or NR$^2$R$^3$;

TABLE 1-continued

Inhibitors of Mapk14 activity

| name | Chemical name or structure |
|---|---|

$R^5$ is H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted;

X is O, S, SO, $SO_2$, $NR^7$, C=O, $CHR^7$, —C=$NOR^1$, —C=$CHR^1$, or $CHOR^1$;

n is 0 or 1,

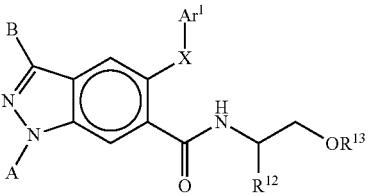

B is H, $NH_2$, or substituted or unsubstituted methyl;
A is H, OH, an amine protecting group, $Z_n$—$NR^2R^3$, $Z_n$—$NR^2$(C=O)$R^2$, $Z_n$—$SO_2R^2$, $Z_n$—$SOR^2$, $Z_n$—$SR^2$, $Z_n$—$OR^2$, $Z_n$—(C=O)$R^2$, $Z_n$—(C=O)$OR^2$, $Z_n$—O—(C=O)$R^2$, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted;
$Ar^1$ is substituted or unsubstituted aryl or heteroaryl;
$R^2$ and $R^3$ are independently H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted, or $R^2$ together with $R^3$ and N forms a saturated or partially unsaturated heterocycle having 1 or more heteroatoms, wherein said heterocycle may be substituted or unsubstituted and wherein said heterocycle may be fused to an aromatic ring;
Z is alkylene having from 1 to 4 carbons, or alkenylene or alkynylene each having from 2 to 4 carbons, wherein said alkylene, alkenylene, or alkynylene may be substituted or unsubstituted;
X is O, S, SO, $SO_2$, $NR^7$, C=O, $CHR^7$, —C=$NOR^1$, —C=$CHR^1$, or $CHOR^1$;
where A, B, X, and $Ar^1$ are defined as above, and $R^{12}$ and $R^{13}$ are independently alkyl, allyl, alkenyl, alkynyl, cycloalkyl, heterocycloalkyl, aryl, or heteroaryl, wherein said alkyl, allyl, alkenyl, alkynyl, cycloalkyl, heterocycloalkyl, aryl, or heteroaryl may be substituted or unsubstituted.
n is 0 or 1,

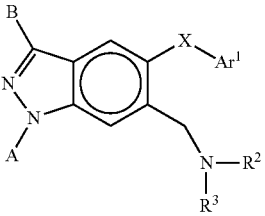

B is H, $NH_2$, or substituted or unsubstituted methyl;
A is H, OH, an amine protecting group, $Z_n$—$NR^2R^3$, $Z_n$—$NR^2$(C=O)$R^2$, $Z_n$—$SO_2R^2$, $Z_n$—$SOR^2$, $Z_n$—$SR^2$, $Z_n$—$OR^2$, $Z_n$—(C=O)$R^2$, $Z_n$—(C=O)$OR^2$, $Z_n$—O—(C=O)$R^2$, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted;
$R^2$ and $R^3$ are independently H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$—$Ar^1$ may be substituted or unsubstituted, or $R^2$ together with $R^3$ and N forms a saturated or partially unsaturated heterocycle having 1 or more heteroatoms, wherein said heterocycle may be substituted or unsubstituted and wherein said heterocycle may be fused to an aromatic ring;
Z is alkylene having from 1 to 4 carbons, or alkenylene or alkynylene each having from 2 to 4 carbons, wherein said alkylene, alkenylene, or alkynylene may be substituted or unsubstituted;
$Ar^1$ is substituted or unsubstituted aryl or heteroaryl;
X is O, S, SO, $SO_2$, $NR^7$, C=O, $CHR^7$, —C=$NOR^1$, —C=$CHR^1$, or $CHOR^1$;
n is 0 or 1, TABLE 1-continued Inhibitors of Mapk14 activity

| name | Chemical name or structure |
|------|---------------------------|

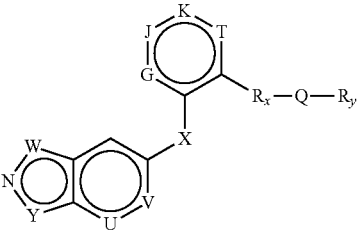

where Y is $CR^1$, O, S, or $NR^2$;
W is $CR^3$, N, $NR^4$, S or O, provided that W is $NR^4$, S, or O when Y is $CR^1$ and W is $CR^3$ or N when Y is $NR^2$;
$R^3$ is H, $NH_2$, F, Cl, methyl or substituted methyl;
$R^4$ is H, or methyl or substituted methyl;
$R^1$ and $R^2$ are independently H, OH, an amine protecting group, $Z_n$—$NR^aR^b$, $Z_n$—$NR^a(C=O)R^b$, $Z_n$—$SO_2R^a$, $Z_n$—$SOR^a$, $Z_n$—$SR^a$, $Z_n$—$OR^a$, $Z_n$—$(C=O)R^a$, $Z_n$—$(C=O)OR^a$, $Z_n$—O—$(C=O)R^a$, alkyl, allyl, alkenyl, alkynyl, heteroalkyl, heteroallyl, heteroalkenyl, heteroalkynyl, alkoxy, heteroalkoxy, $Z_n$-cycloalkyl wherein said cycloalkyl is saturated or partially unsaturated, $Z_n$-heterocycloalkyl wherein said heterocycloalkyl is saturated or partially unsaturated, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, and $Z_n$—$Ar^1$ may be substituted or unsubstituted;
$Ar^1$ is aryl or heteroaryl, each of which may be substituted or unsubstituted;
$R^a$ and $R^b$ are independently H, OH, an amine protecting group, an alcohol protecting group, an acid protecting group, a sulfur protecting group, alkyl, allyl, alkenyl, alkynyl, heteroalkyl, heteroallyl, heteroalkenyl, heteroalkynyl, alkoxy, heteroalkoxy, $Z_n$-cycloalkyl wherein said cycloalkyl is saturated or partially unsaturated, $Z_n$-heterocycloalkyl wherein said heterocycloalkyl is saturated or partially unsaturated, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, and $Z_n$—$Ar^1$ may be substituted or unsubstituted,
or $R^a$ and $R^b$ together with the atoms to which they are both attached form a saturated or partially unsaturated heterocycle ring having 1 or more heteroatoms in said ring, wherein said heterocycle may be substituted or unsubstituted and wherein said heterocycle may be fused to an aromatic ring;
Z is alkylene having from 1 to 4 carbons, or alkenylene or alkynylene each having from 2 to 4 carbons, wherein said alkylene, alkenylene, or alkynylene may be substituted or unsubstituted;
n is 0 or 1;
U is $CR^c$ or N;
V is $CR^c$ or N;
$R^c$ is H, F, Cl, methyl or substituted methyl;
X is O, S, SO, $SO_2$, $NR^5$, C=O, $CH_2$, $CH_2Z_n$—OH, or C=$NOR^d$;
$R^5$ is H, methyl, or substituted methyl;
$R^d$ is H, $PO_3H_2$, $SO_3H_2$, alkyl, allyl, alkenyl, alkynyl, heteroalkyl, heteroallyl, heteroalkenyl, heteroalkynyl, alkoxy, heteroalkoxy, $Z_n$-cycloalkyl wherein said cycloalkyl is saturated or partially unsaturated, $Z_n$-heterocycloalkyl wherein said heterocycloalkyl is saturated or partially unsaturated, or $Z_n$—$Ar^1$, said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl and $Z_n$—$Ar^1$ may be substituted or unsubstituted;
G, H, J, and T independently are N or $CR^z$, provided that when any of said G, H, J, and T are N the total number of G, H, J, or T that is N does not exceed 2;
$R^z$ is H, F, Cl, Br, $CF_3$, $OR^6$, $SR^6$, lower alkyl ($C_1$-$C_4$), CN, or $NR^6R^7$;
$R^6$ and $R^7$ are independently H, $CF_3$, lower alkyl ($C_1$-$C_4$) or lower heteroalkyl ($C_1$-$C_4$);
Q is —$NR^8$CONH—, —NHCO—, —$NR^8SO_2$NH—, —$NHSO_2$—, —$CONR^{11}$—;
$R^8$ is H or lower ($C_1$-$C_4$) alkyl;
$R^{11}$ is H or lower ($C_1$-$C_4$) alkyl;
$R_x$ is —$(CR^9R^{10})_m$—, —$O(CR^9R^{10})_m$—, $NH(CR^9R^{10})_m$—, or —$S(CR^9R^{10})_m$-provided that Q is —$CONR^{11}$— when $R^x$ is —$O(CR^9R^{10})_m$—, —$NH(CR^9R^{10})_m$—, or —$S(CR^9R^{10})_m$—;
$R^9$ and $R^{10}$ are independently H, or lower alkyl, or $R^9$ and $R^{10}$ together with the atoms to which they are both attached form a cycloalkyl ring which may be saturated or partially unsaturated;
m is 1-3;
$R_y$ is H, $PO_3H$, an amine protecting group, an oxygen protecting group, alkyl, allyl, alkenyl, alkynyl, heteroalkyl, heteroallyl, heteroalkenyl, heteroalkynyl, alkoxy, heteroalkoxy, $Z_n$-cycloalkyl wherein said cycloalkyl is saturated or partially unsaturated, $Z_n$-heterocycloalkyl wherein said heterocycloalkyl is saturated or partially unsaturated, or $Z_n$—$Ar^2$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$—$Ar^2$ and $Z_n$-heterocycloalkyl may be substituted or unsubstituted;
$Ar^2$ is aryl or heteroaryl, each of which may be substituted or unsubstituted, wherein said substitution can be 1-3 substituents independently selected from F, Cl, Br, $CF_3$, CN, alkyl, allyl, alkenyl, alkynyl, heteroalkyl, heteroallyl, heteroalkenyl, heteroalkynyl, —$OR^{12}$, —$SR^{12}$, —$SO_2R^{12}$, —$SO_2NR^{13}R^{12}$, $NR^{13}SO_2R^{12}$, $Z_n$-cycloalkyl wherein said cycloalkyl is saturated or partially unsaturated, $Z_n$-heterocycloalkyl wherein said heterocycloalkyl is saturated or partially unsaturated, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl and $Z_n$—$Ar^1$ may be substituted or unsubstituted;
$R^{12}$ and $R^{13}$ are independently H, alkyl, allyl, alkenyl, alkynyl, heteroalkyl, heteroallyl, heteroalkenyl, heteroalkynyl, $Z_n$-cycloalkyl wherein said cycloalkyl is saturated or partially unsaturated, $Z_n$-heterocycloalkyl wherein said heterocycloalkyl is saturated or partially unsaturated, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl and $Z_n$—$Ar^1$ may be substituted or unsubstituted;
wherein when $Ar^2$ is substituted with —$SO_2NR^{13}R^{12}$, $R^{12}$ and $R^{13}$ can form a cycloalkyl ring or heterocycloalkyl ring that may be substituted or unsubstituted wherein said substitution can be substituents selected from alkyl, allyl, alkenyl, alkynyl, heteroalkyl, heteroallyl, heteroalkenyl, heteroalkynyl, alkoxy, heteroalkoxy, $Z_n$-cycloalkyl wherein

TABLE 1-continued

Inhibitors of Mapk14 activity

| name | Chemical name or structure |
|------|----------------------------|
| | said cycloalkyl is saturated or partially unsaturated, —$COR^{12}$, —$SO_2R^{12}$, $Z_n$-heterocycloalkyl wherein said heterocycloalkyl is saturated or partially unsaturated, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl and $Z_n$—$Ar^1$ may be substituted or unsubstituted;<br>wherein when Q is —$CONR^{11}$, $R_y$ in combination with $R^{11}$ is additionally cycloalkyl ring or heterocycloalkyl ring that may be substituted or unsubstituted with groups selected from alkyl, allyl, alkenyl, alkynyl, heteroalkyl, heteroallyl, heteroalkenyl, heteroalkynyl, alkoxy, heteroalkoxy, $Z_n$-cycloalkyl wherein said cycloalkyl is saturated or partially unsaturated, $Z_n$-heterocycloalkyl wherein said heterocycloalkyl is saturated or partially unsaturated, $Z_n$—$Ar^1$, —$COR^{14}$, or —$SO_2R^{14}$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, $Z_n$—$Ar^1$, —$COR^{14}$, and —$SO_2R^{14}$ may be substituted or unsubstituted; and<br>$R^{14}$ is alkyl, allyl, alkenyl, alkynyl, heteroalkyl, heteroallyl, heteroalkenyl, heteroalkynyl, $Z_n$-cycloalkyl wherein said cycloalkyl is saturated or partially unsaturated, $Z_n$-heterocycloalkyl wherein said heterocycloalkyl is saturated or partially unsaturated, or $Z_n$—$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, and $Z_n$—$Ar^1$ may be substituted or unsubstituted.<br>n is 0 or 1,<br><br>5-(4-fluorophenoxy)-1-isobutyl-1H-indazole-6-carboxylic acid amide<br>[5-(4-fluorophenoxy)-1-isobutyl-1H-indazol-6-yl]morpholin-4-yl-methanone<br>[5-(4-fluorophenoxy)-1-isobutyl-1H-indazol-6-yl]-(4-methylpiperazin-1-yl)-methanone<br>5-(4-fluorophenoxy)-1-isobutyl-1H-indazole-6-carboxylic acid (1-benzyl-piperidin-4-yl)amide<br>5-(4-fluorophenoxy)-1-isobutyl-1H-indazole-6-carboxylic acid (2-benzylaminoethyl)amide<br>5-(4-fluorophenoxy)-1-isobutyl-1H-indazole-6-carboxylic acid (2-piperidin-yl-ethyl)amide<br>5-(4-fluorophenoxy)-1-isobutyl-1H-indazole-6-carboxylic acid (2-pyrrolidin-1-yl-ethyl)amide<br>5-(4-fluorophenoxy)-1-isobutyl-1H-indazole-6-carboxylic acid (3-morpholin-4-yl-propyl)amide<br>5-(4-fluorophenoxy)-1-isobutyl-1H-indazole-6-carboxylic acid (3-demethylaminopropyl)amide<br>5-(4-fluorophenoxy)-1-isobutyl-1H-indazole-6-carboxylic acid (2-dimethylaminoethyl)amide<br>5-(4-fluorophenoxy)-1-isobutyl-1H-indazole-6-carboxylic acid methyl-(1-methylpiperidin-4-yl)amide<br>5-(4-fluorophenoxy)-1-isobutyl-1H-indazole-6-carboxylic acid [3-(methylphenylamino)-propyl]amide<br>3-{[5-(4-fluorophenoxy)-1-isobutyl-1H-indazole-6-carbonyl]-amino}-pyrrolidine-1-carboxylic acid tert-butyl ester<br>5-(4-fluorophenoxy)-1-(2,2,2-trifluoroethyl)-1H-indazole-6-carboxylic acid (2-dimethylaminoethyl)amide<br>5-(4-fluorophenoxy)-1-methyl-1H-indazole-6-carboxylic acid (2-dimethyl-aminoethyl)amide<br>5-(4-fluorophenoxy)-1H-indazole-6-carboxylic acid (2-dimethyl-aminoethyl)amide<br>4-amino-2-{[5-(4-fluorophenoxy)-1-isobutyl-1H-indazole-6-carbonyl]-amino} butyric acid methyl ester<br>4-amino-2-{[5-(4-fluorophenoxy)-1-(2,2,2-trifluoroethyl)-1H-indazole-6-carbonyl]-amino} butyric acid methyl ester<br>4-amino-2-{[5-(4-fluorophenoxy)-1-methyl-1H-indazole-6-carbonyl]-amino} butyric acid methyl ester<br>(S)-N-(4-amino-1-hydroxybutan-2-yl)5-(4-fluorophenoxy)-1-isobutyl-1H-indazole-6-carboxamide<br>(S)-methyl 2-(5-(2,4-difluorophenoxy)-1-isobutyl-1H-indazole-6-carboxamido)-4-(dimethylamino)butanoate<br>(S)-5-(2,4-difluorophenoxy)-N-(4-(dimethylamino)-1-hydroxybutan-2-yl)-1-isobutyl-1H-indazole-6-carboxamide<br>(S)-5-(2,4-difluorophenoxy)-1-isobutyl-1H-indazole-6-carboxylic acid (1-hydroxymethyl-3-isopropylaminopropyl)amide<br>(S)-2-{[5-(2,4-difluorophenoxy)-1-isobutyl-1H-indazole-6-carbonyl]-amino}-4-dimethylaminobutyric acid<br>(S)-5-(2,4-difluorophenoxy)-1-isobutyl-1H-indazole-6-carboxylic acid (1-hydroxymethyl-3-piperidin-1-yl-propyl)amide<br>(S)-5-(2,4-difluorophenoxy)-1-isobutyl-1H-indazole-6-carboxylic acid (3-dimethylamino-1-dimethylcarbamoyl-propyl)amide<br>(S)-5-(2,4-difluorophenoxy)-1-isobutyl-1H-indazole-6-carboxylic acid (1-carbamoyl-3-dimethylaminopropyl)amide<br>(S)-5-(2,4-difluorophenoxy)-1-isobutyl-1H-indazole-6-carboxylic acid [1-(2-dimethylaminoethyl-2-hydroxy-2-methylpropyl]amide<br>(S)-5-(2,4-difluorophenoxy)-1-isobutyl-1H-indazole-6-carboxylic acid (1-hydroxymethyl-3-[(2-methoxyethyl)methyl-amino]propyl}amide<br>(S)-5-(2,4-difluorophenoxy)-1-isobutyl-1H-indazole-6-carboxylic acid [3-dimethylamino-1-(2-hydroxyethyl-carbamoyl)propyl]amide<br>5-(2,4-difluorophenoxy)-1-isobutyl-1H-indazole-6-sulfonic acid (3-dimethylaminopropyl) amide<br>(S)-methyl 2-(5-(2,4-difluorophenoxy)-1-isobutyl-1H-indazole-6-sulfonamido)-4-(dimethylamino)butanoate<br>5-(2,4-difluorophenoxy)-1-isobutyl-1H-indazole-6-sulfonic acid [2-(1-methylpyrrolidin-2-yl)-ethyl]amide<br>5-(2,4-difluorophenoxy)-1-isobutyl-1H-indazole-6-sulfonic acid [2-dimethylaminoethyl)amide<br>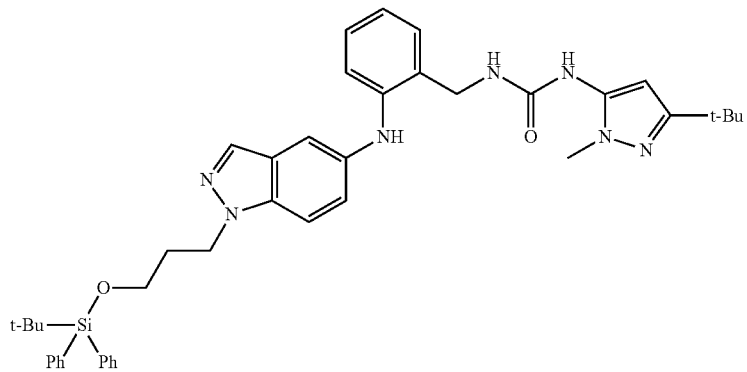 [SMILES: Cn1nc(C(C)(C)C)cc1NC(=O)NCc1ccccc1Nc1ccc2c(cnn2CCCO[Si](c2ccccc2)(c2ccccc2)C(C)(C)C)c1] |

TABLE 1-continued
Inhibitors of Mapk14 activity
| name | Chemical name or structure |
|---|---|
| | 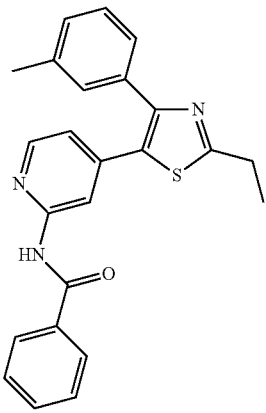 [SMILES: CCc1nc(-c2cccc(C)c2)c(-c2ccnc(NC(=O)c3ccccc3)c2)s1] |
| | 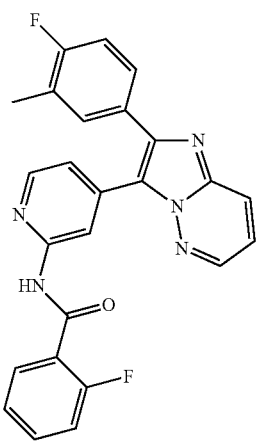 [SMILES: Cc1cc(-c2nc3cccnn3c2-c2ccnc(NC(=O)c3ccccc3F)c2)ccc1F] |
| | 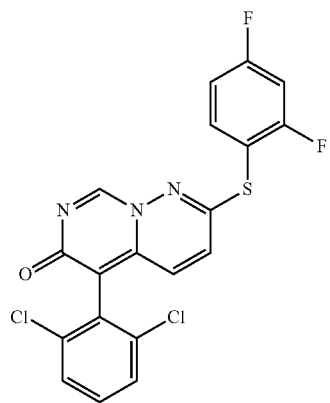<br>IC50 = 5 nM, |

TABLE 1-continued
Inhibitors of Mapk14 activity
| name | Chemical name or structure |
|---|---|
| | 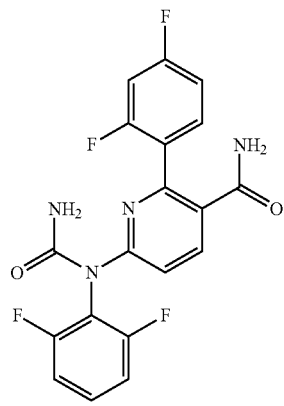 [SMILES: NC(=O)c1ccc(N(C(N)=O)c2c(F)cccc2F)nc1-c1ccc(F)cc1F] |
| | 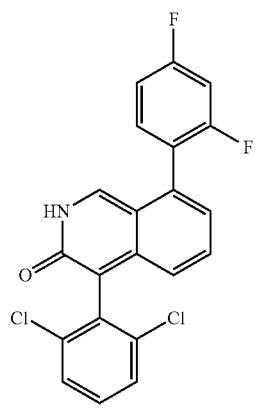 [SMILES: O=c1[nH]cc2c(-c3ccc(F)cc3F)cccc2c1-c1c(Cl)cccc1Cl] |
| | 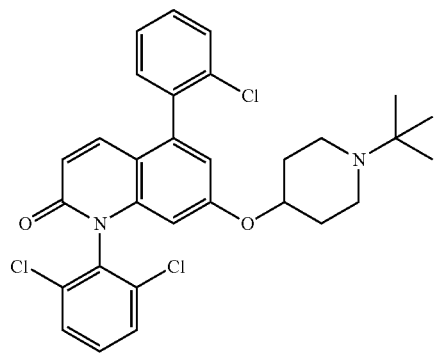 [SMILES: CC(C)(C)N1CCC(Oc2cc(-c3ccccc3Cl)c3ccc(=O)n(-c4c(Cl)cccc4Cl)c3c2)CC1] |

TABLE 1-continued
Inhibitors of Mapk14 activity
| name | Chemical name or structure |
| --- | --- |
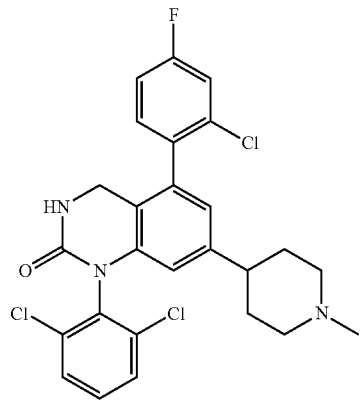
IC50 p38 α = 0.5 nM (kinase enzyme assay)
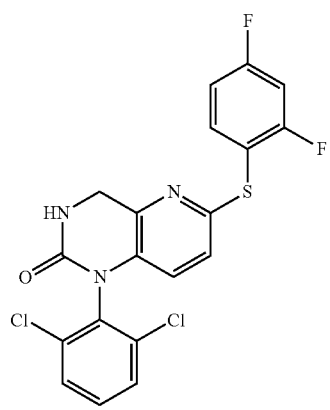 [SMILES: O=C1NCc2nc(Sc3ccc(F)cc3F)ccc2N1c1c(Cl)cccc1Cl]
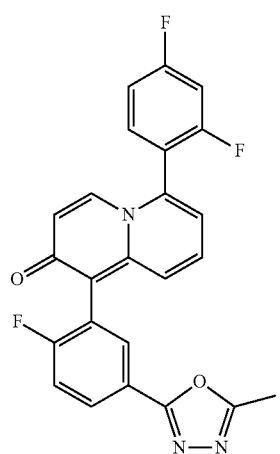
IC50 p38α = 15 nM TABLE 1-continued
Inhibitors of Mapk14 activity
| name | Chemical name or structure |
| --- | --- |
| | 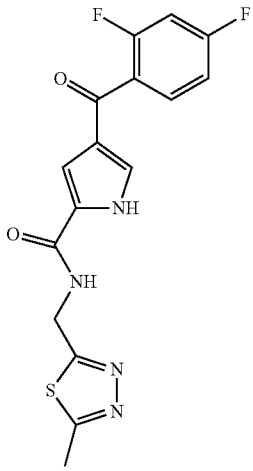 [SMILES: Cc1nnc(CNC(=O)c2cc(C(=O)c3ccc(F)cc3F)c[nH]2)s1] |
| | 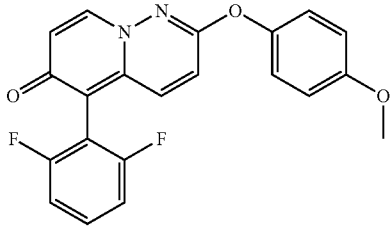 [SMILES: COc1ccc(Oc2ccc3c(-c4c(F)cccc4F)c(=O)ccn3n2)cc1] |
| | 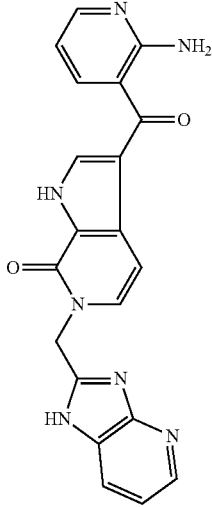 [SMILES: Nc1ncccc1C(=O)c1c[nH]c2c(=O)n(Cc3nc4ncccc4[nH]3)ccc12] |
| | 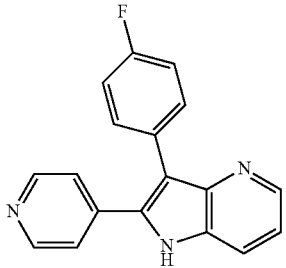 [SMILES: Fc1ccc(-c2c(-c3ccncc3)[nH]c3cccnc23)cc1] |

163 164
TABLE 1-continued
Inhibitors of Mapk14 activity
| name | Chemical name or structure |
|---|---|
| | 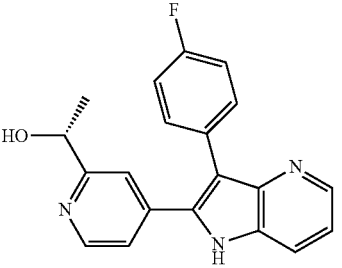 [SMILES: C[C@@H](O)c1cc(-c2[nH]c3cccnc3c2-c2ccc(F)cc2)ccn1] |
| | 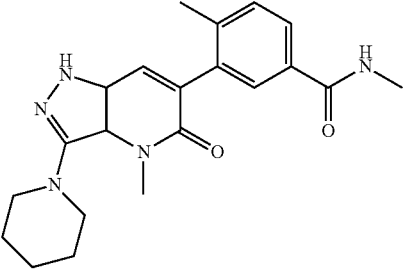 [SMILES: CNC(=O)c1ccc(C)c(C2=CC3NN=C(N4CCCCC4)C3N(C)C2=O)c1] |
| | 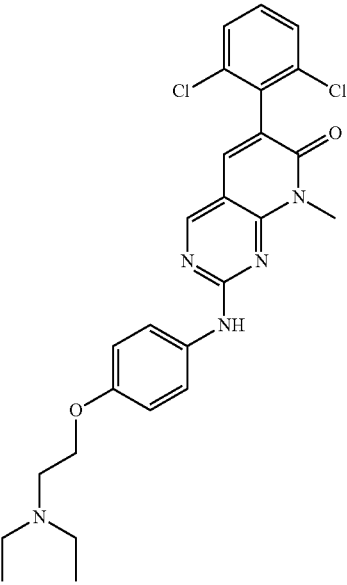 [SMILES: CCN(CC)CCOc1ccc(Nc2ncc3cc(-c4c(Cl)cccc4Cl)c(=O)n(C)c3n2)cc1] |
| | 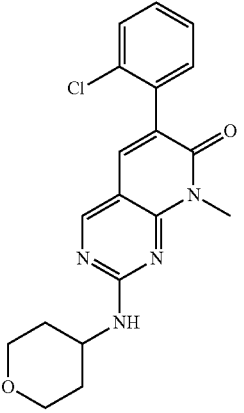 [SMILES: Cn1c(=O)c(-c2ccccc2Cl)cc2cnc(NC3CCOCC3)nc21] |

TABLE 1-continued
Inhibitors of Mapk14 activity
| name | Chemical name or structure |
|---|---|
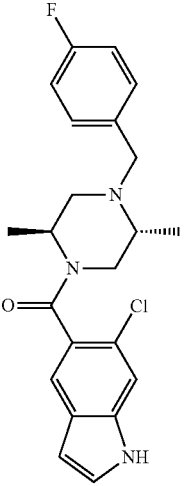
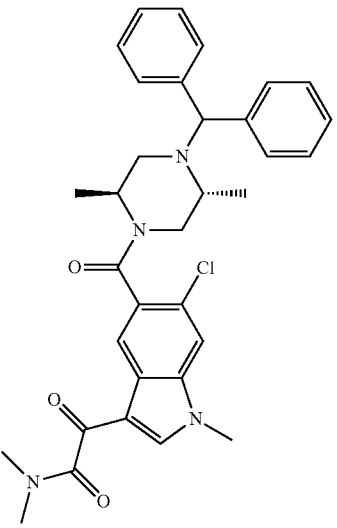 [SMILES: C[C@@H]1CN(C(=O)c2cc3c(C(=O)C(=O)N(C)C)cn(C)c3cc2Cl)[C@@H](C)CN1C(c1ccccc1)c1ccccc1]
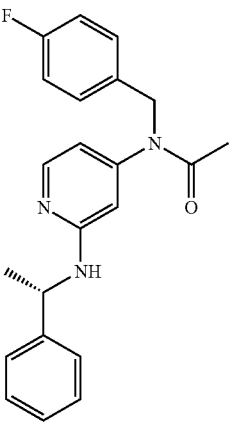 [SMILES: CC(=O)N(Cc1ccc(F)cc1)c1ccnc(N[C@@H](C)c2ccccc2)c1]

TABLE 1-continued
Inhibitors of Mapk14 activity
| name | Chemical name or structure |
|------|---------------------------|
|  | 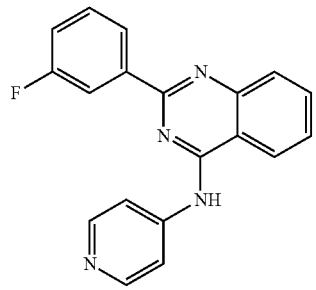 [SMILES: Fc1cccc(-c2nc(Nc3ccncc3)c3ccccc3n2)c1] |
|  | 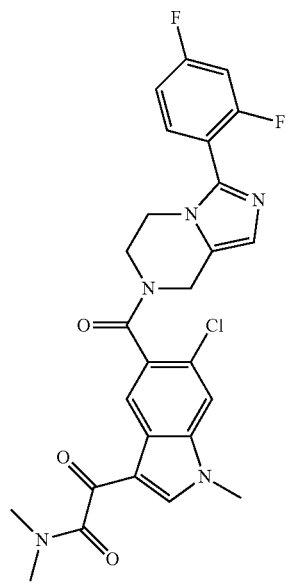<br>IC50 p38α = 11 nM |
|  | 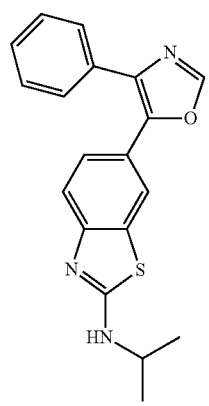 [SMILES: CC(C)Nc1nc2ccc(-c3ocnc3-c3ccccc3)cc2s1] |

TABLE 1-continued

Inhibitors of Mapk14 activity

| name | Chemical name or structure |
|------|----------------------------|

IC50 p38α = 3.1 nM

TABLE 1-continued
Inhibitors of Mapk14 activity
| name | Chemical name or structure |
|---|---|
| | 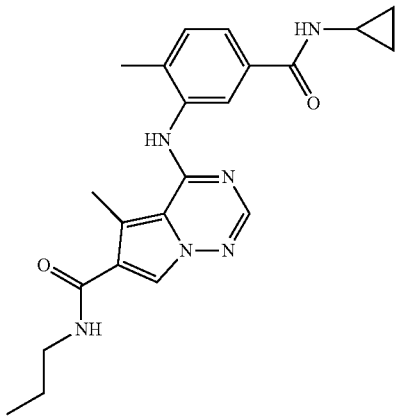 [SMILES: CCCNC(=O)c1cn2ncnc(Nc3cc(C(=O)NC4CC4)ccc3C)c2c1C] |
| | 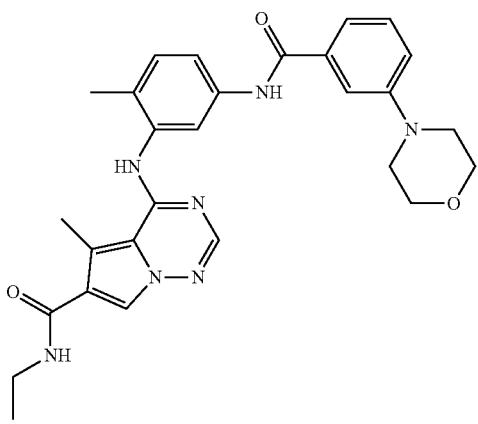 [SMILES: CCNC(=O)c1cn2ncnc(Nc3cc(NC(=O)c4cccc(N5CCOCC5)c4)ccc3C)c2c1C] |
| | 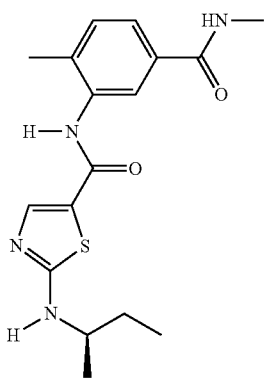 [SMILES: CC[C@@H](C)Nc1ncc(C(=O)Nc2cc(C(=O)NC)ccc2C)s1] |

173 174
TABLE 1-continued
Inhibitors of Mapk14 activity
| name | Chemical name or structure |
| --- | --- |
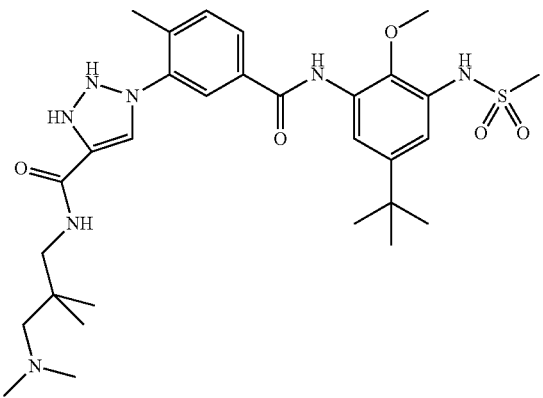
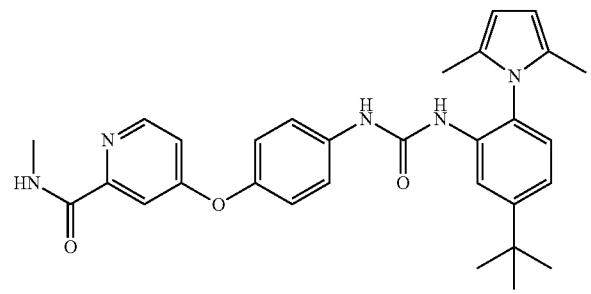
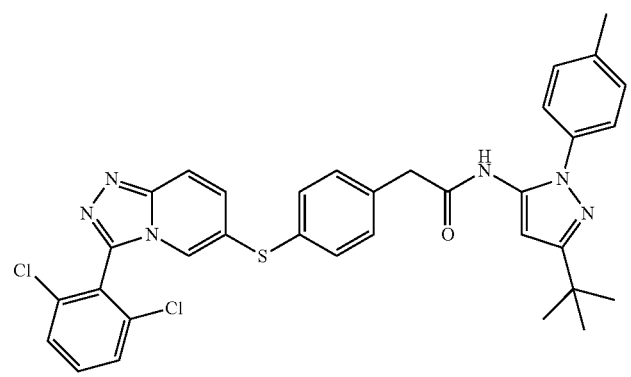
IC50 p38α < 10 nM TABLE 1-continued
Inhibitors of Mapk14 activity
| name | Chemical name or structure |
|---|---|
| | 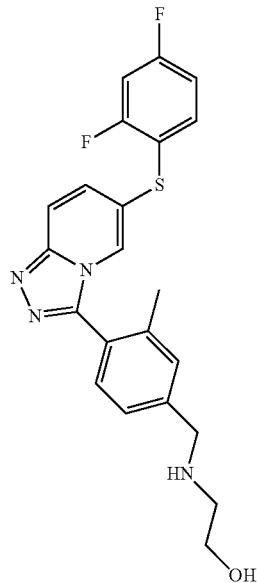 [SMILES: Cc1cc(CNCCO)ccc1-c1nnc2ccc(Sc3ccc(F)cc3F)cn12] |
| | 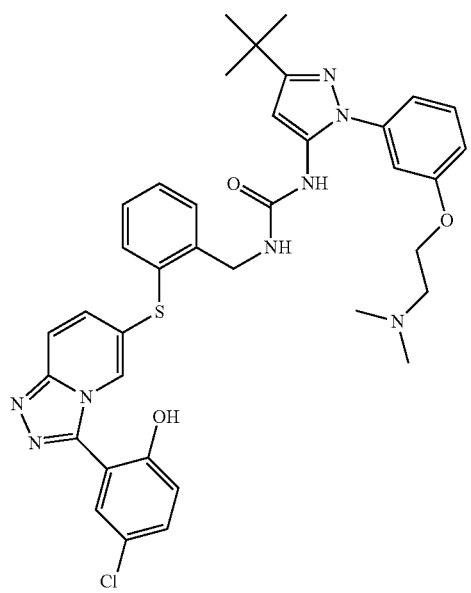 [SMILES: CN(C)CCOc1cccc(-n2nc(C(C)(C)C)cc2NC(=O)NCc2ccccc2Sc2ccc3nnc(-c4cc(Cl)ccc4O)n3c2)c1] |

TABLE 1-continued
Inhibitors of Mapk14 activity
| name | Chemical name or structure |
|------|----------------------------|
|      | 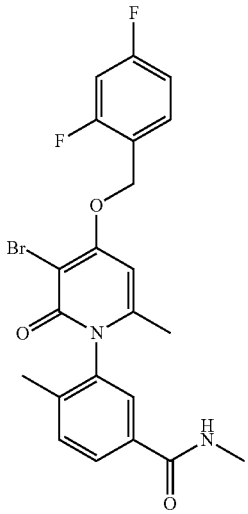 [SMILES: CNC(=O)c1ccc(C)c(-n2c(C)cc(OCc3ccc(F)cc3F)c(Br)c2=O)c1] |
|      | 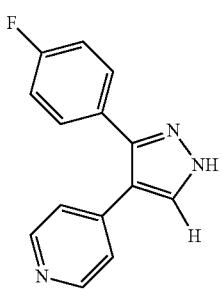 [SMILES: Fc1ccc(-c2n[nH]cc2-c2ccncc2)cc1] |
|      | 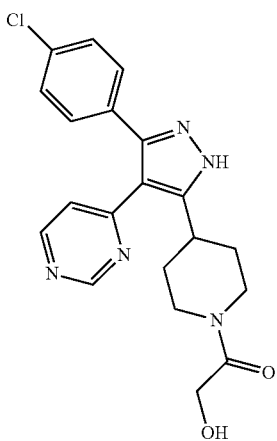 [SMILES: O=C(CO)N1CCC(c2[nH]nc(-c3ccc(Cl)cc3)c2-c2ccncn2)CC1] |

TABLE 1-continued
Inhibitors of Mapk14 activity
| name | Chemical name or structure |
|---|---|
| | 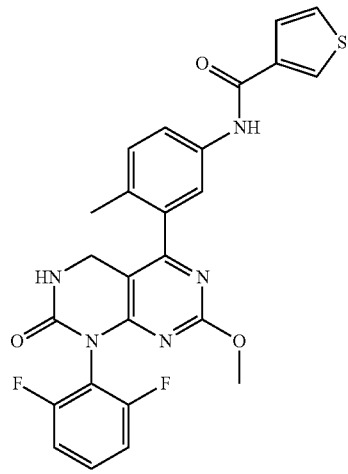 [SMILES: COc1nc(-c2cc(NC(=O)c3ccsc3)ccc2C)c2c(n1)N(c1c(F)cccc1F)C(=O)NC2] |
| | 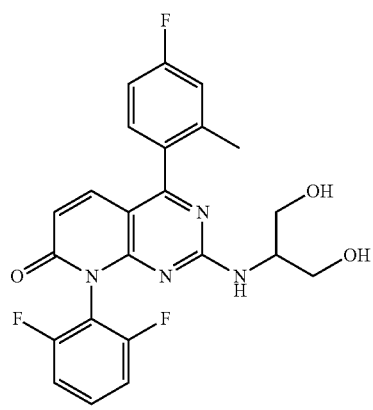 [SMILES: Cc1cc(F)ccc1-c1nc(NC(CO)CO)nc2c1ccc(=O)n2-c1c(F)cccc1F] |
| | 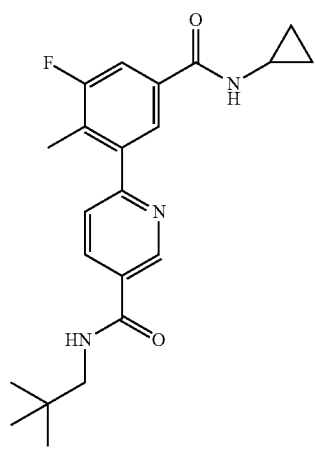 [SMILES: Cc1c(F)cc(C(=O)NC2CC2)cc1-c1ccc(C(=O)NCC(C)(C)C)cn1] |

TABLE 1-continued

Inhibitors of Mapk14 activity

| name | Chemical name or structure |
|---|---|

TABLE 1-continued
Inhibitors of Mapk14 activity
| name | Chemical name or structure |
|---|---|
| | 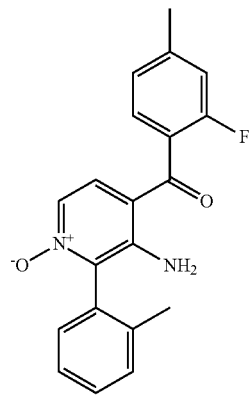<br>IC50 p38α = 21 nM |
| | 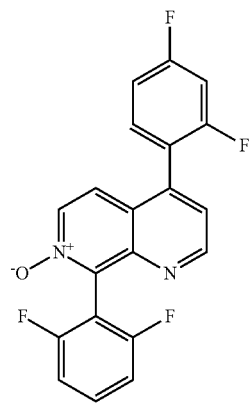 |
| | 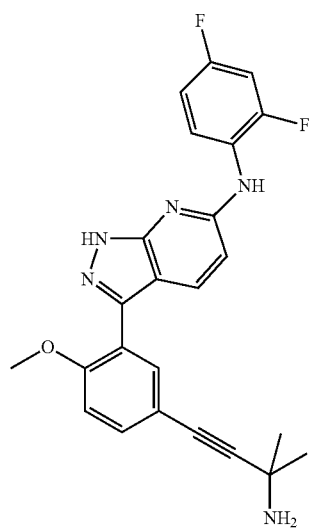 [SMILES: COc1ccc(C#CC(C)(C)N)cc1-c1n[nH]c2nc(Nc3ccc(F)cc3F)ccc12] |

TABLE 1-continued
Inhibitors of Mapk14 activity
| name | Chemical name or structure |
|---|---|
| | 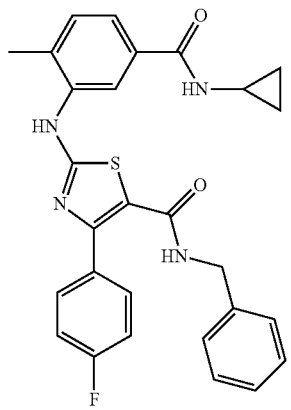 [SMILES: Cc1ccc(C(=O)NC2CC2)cc1Nc1nc(-c2ccc(F)cc2)c(C(=O)NCc2ccccc2)s1] |
| | 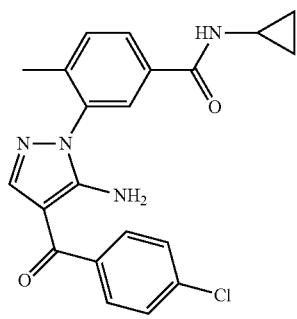 [SMILES: Cc1ccc(C(=O)NC2CC2)cc1-n1ncc(C(=O)c2ccc(Cl)cc2)c1N] |
| | 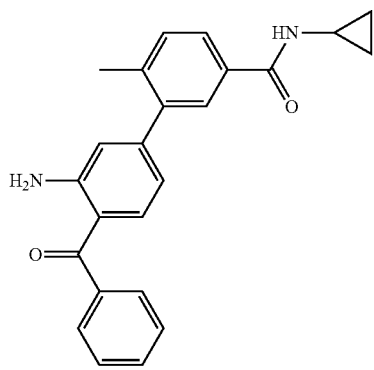 [SMILES: Cc1ccc(C(=O)NC2CC2)cc1-c1ccc(C(=O)c2ccccc2)c(N)c1] |
| | 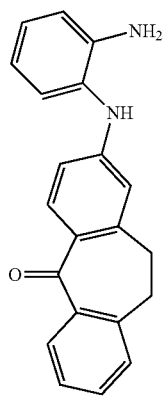 [SMILES: Nc1ccccc1Nc1ccc2c(c1)CCc1ccccc1C2=O] |

187
188
TABLE 1-continued
Inhibitors of Mapk14 activity
| name | Chemical name or structure |
|------|----------------------------|
|      | 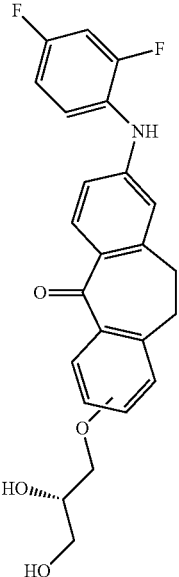       |
|      | 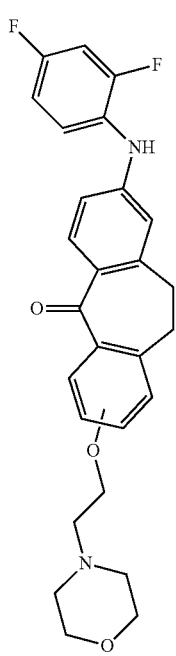       |

TABLE 1-continued

Inhibitors of Mapk14 activity

| name | Chemical name or structure |
|---|---|

TABLE 1-continued

Inhibitors of Mapk14 activity

| name | Chemical name or structure |
|---|---|
| BMS-582949 | |
| Skepinone-L | 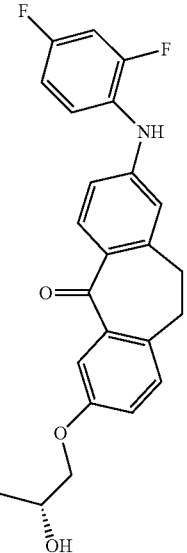<br>IC50 = 25 nM |

Unless otherwise defined, substituents R1 to R14 can be selected independently from the group comprising $CH_3$, $CH_2CH_3$, $CH_2CH_3CH_3$, $CH_2(CH_2)_2CH_3$, $CH_2$=$CH_2$, H, F, Cl, Br, I, $SO_2$, $CF_3$, $N_3$, OH, $NH_2$, =O, $N(CH_3)_2$, OMe, OEt, $SO_2Me$. In Table 1, IC50 values are for Mapk14.

In the above Table, references to tradenames, trivial names and especially to publication number of patents or patent applications include the subject-matter of such references and publications into the present application, especially in respect of characterizations and methods for synthesis of the compounds.

It was found in in vitro assays using cultivated liver cancer cells of both murine and human origin, respectively, that the efficacy of Sorafenib against liver cancer cells was increased in the presence of an inhibitor of Mapk14 activity. As examples for inhibitors of Mapk14 activity, BIRB-796, SB 202190, or SX 011 were used, which are kinase inhibitors that act upon and/or are specific for Mapk14 protein.

DETAILED DESCRIPTION OF THE INVENTION

Figure 2:
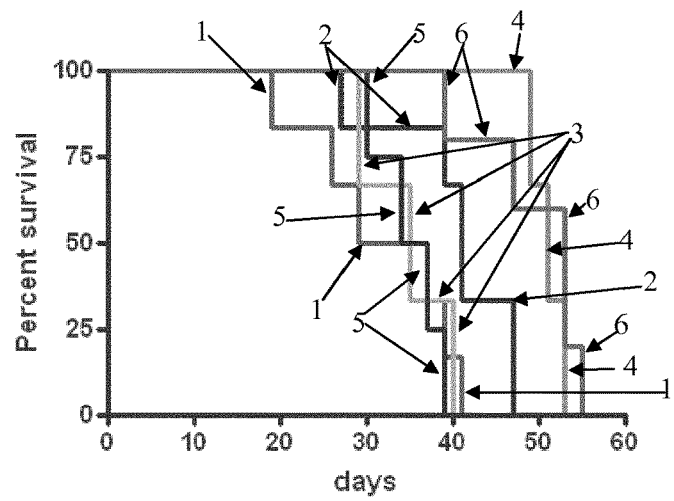
Figure 3:
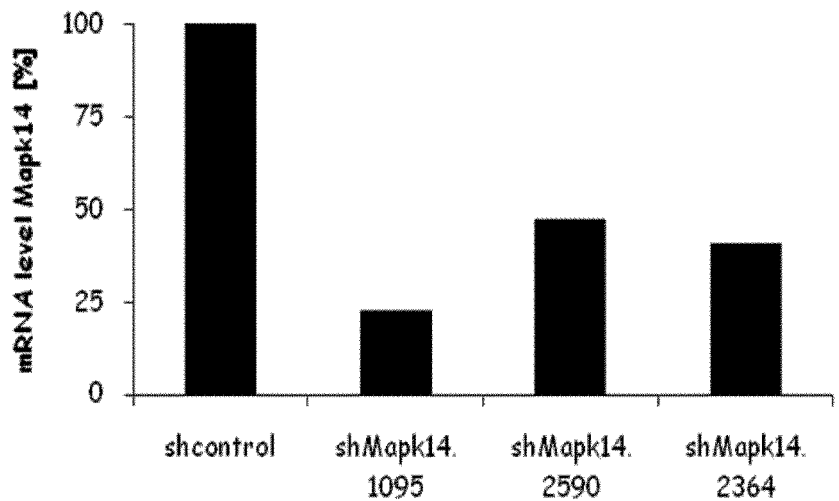
Figure 4:
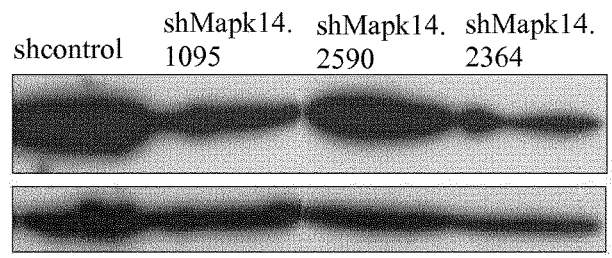
Figure 5:
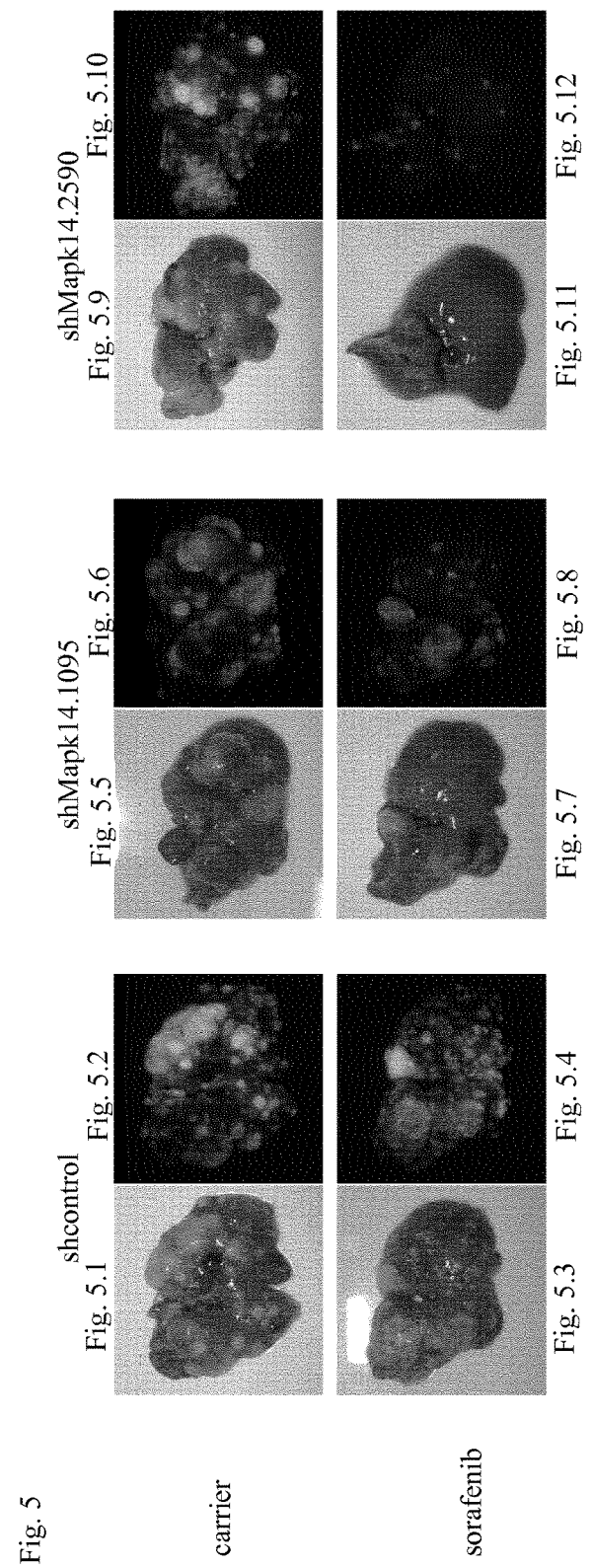
Figure 6:
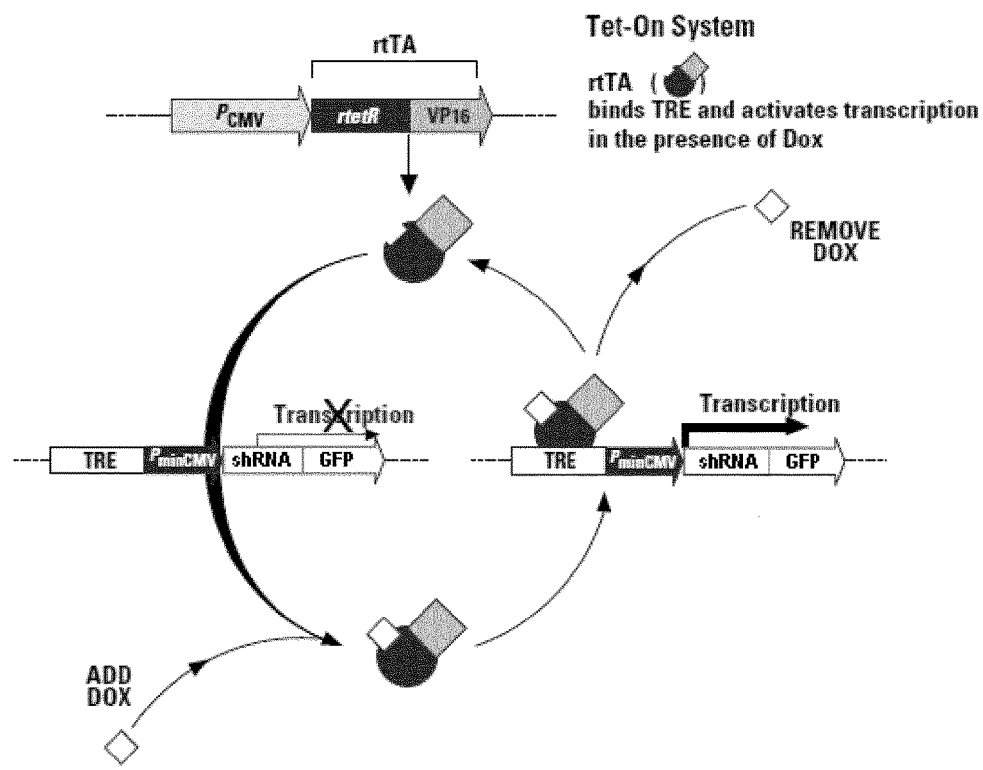

The invention is now described by way of examples with reference to the figures, wherein FIG. 1 schematically shows the constructs used for genetically manipulating mice for generation of liver carcinomas with concurrent expression of shRNAs which can be non-specific or specific for the mRNA encoding Mapk14, FIG. 2 shows the survival rates of mice expressing different shRNA molecules with and without administration of Sorafenib, FIG. 3 shows the detected levels of mRNA specific for Mapk14 with expression of shRNAs which are non-specific or specific for the mRNA encoding Mapk14, FIG. 4 shows a Western blot with specific detection for Mapk14 protein levels from cells expressing shRNA with or without specificity for Mapk14 mRNA, and with detection for α-tubulin as a loading control, FIG. 5 shows micrographs and GFP images of explanted mouse livers with and without administration of Sorafenib and expression of shRNAs specific for Mapk14 mRNA and controls, FIG. 6 schematically depicts the mechanism of the doxycycline dependent transcription of shRNAs and the GFP marker gene.

Figure 7:
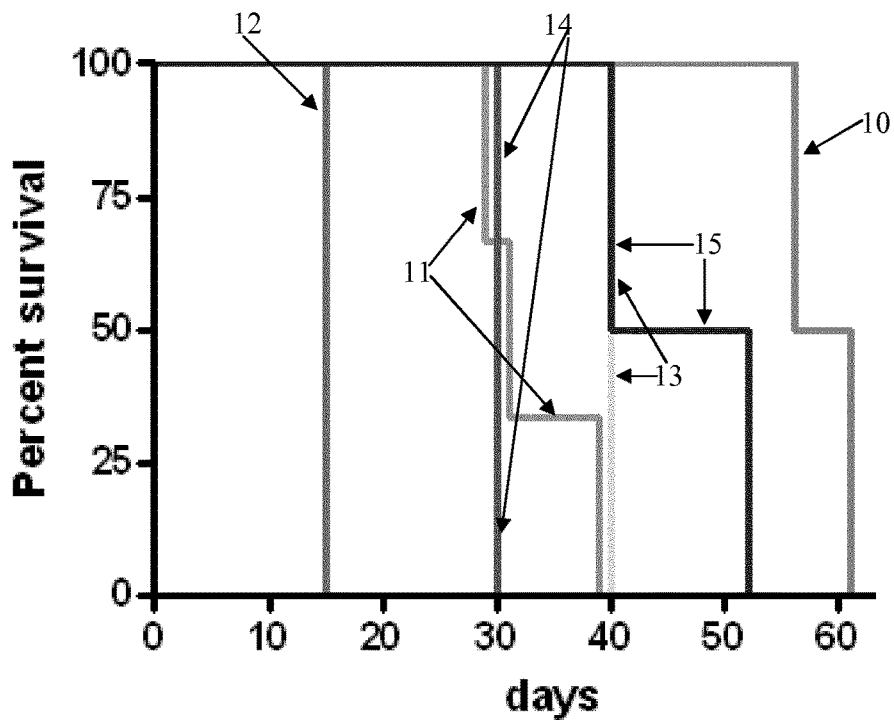

FIG. 7 shows the survival rates of mice treated with Sorafenib or a control compound (carrier) in the presence of the shRNA specific for the mRNA encoding Mapk14, (which transcription was activated 5 days after tumor development) and in the absence of the shRNA specific for the mRNA encoding Mapk14, as well as control shRNAs.

Figure 8:
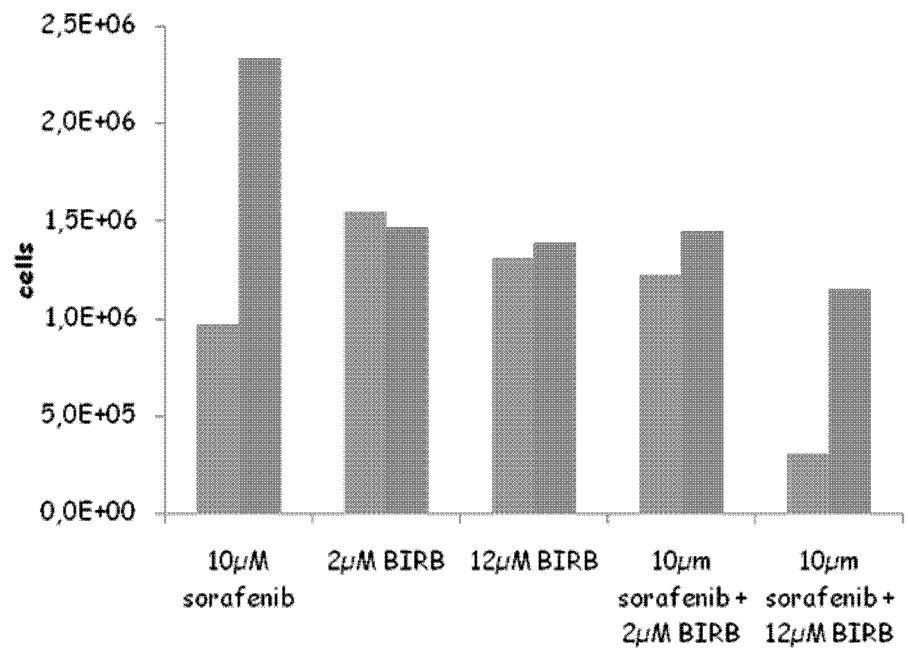
Figure 9:
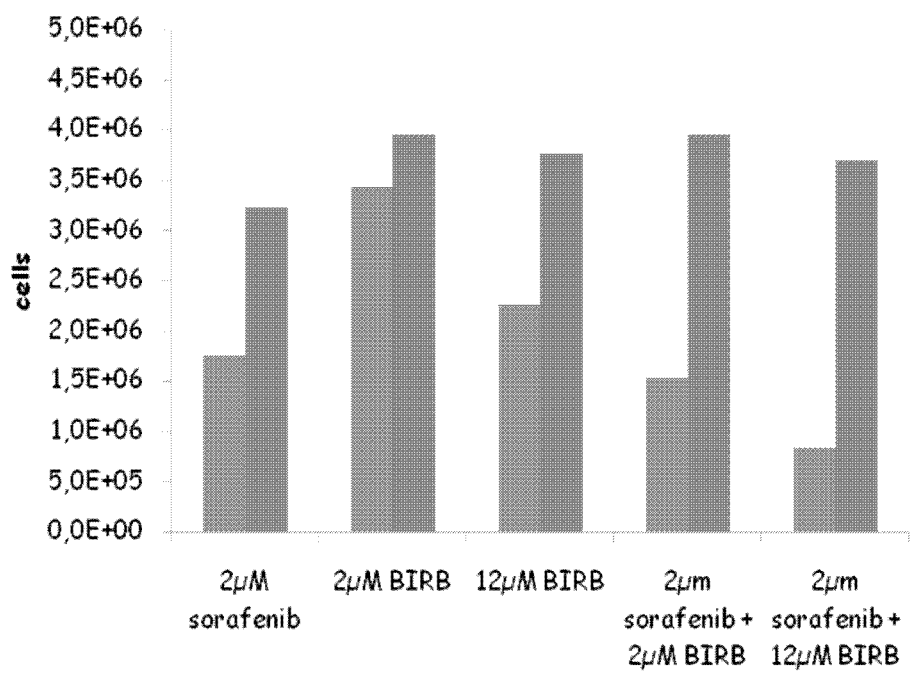
Figure 10:
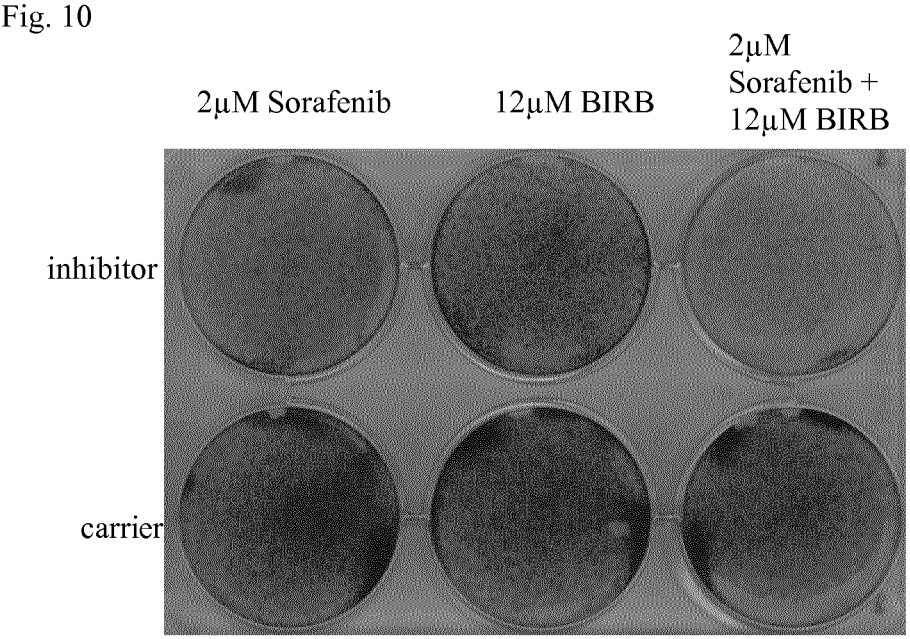
Figure 11:
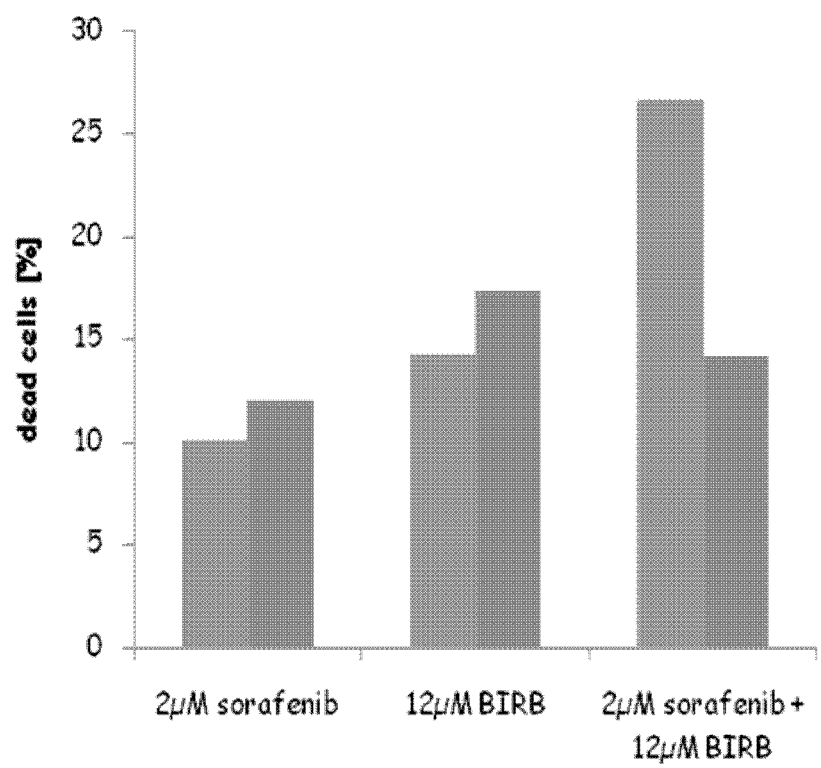
Figure 12:
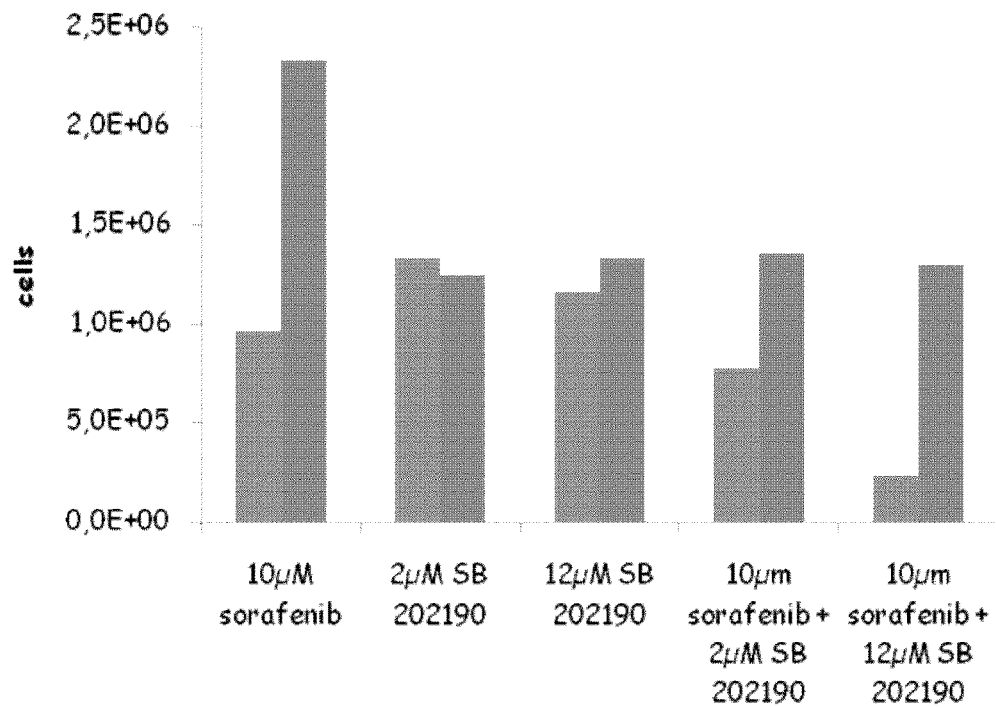
Figure 13:
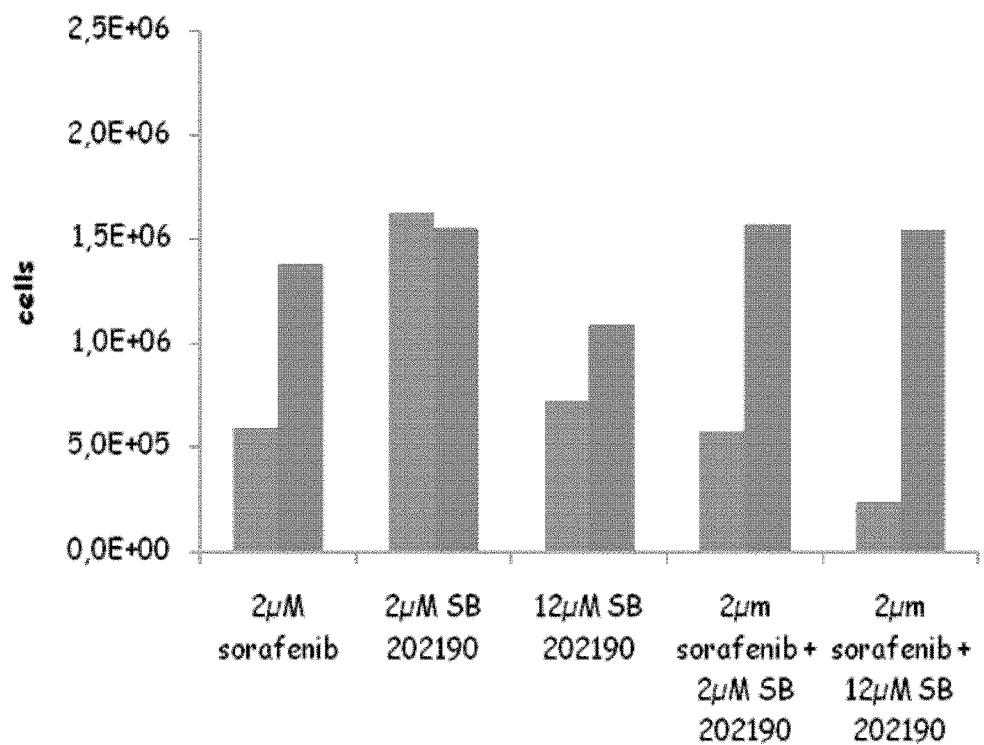
Figure 14:
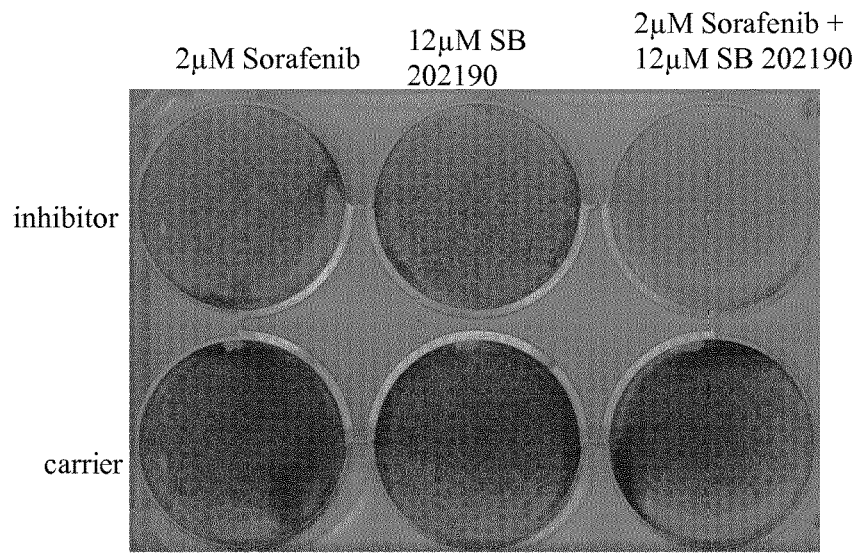
Figure 15:
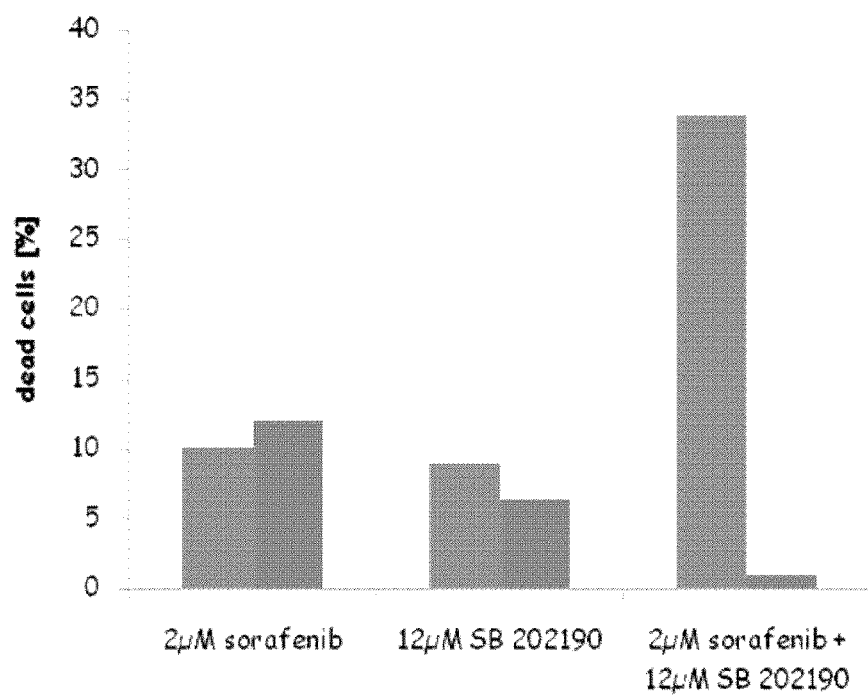
Figure 16:
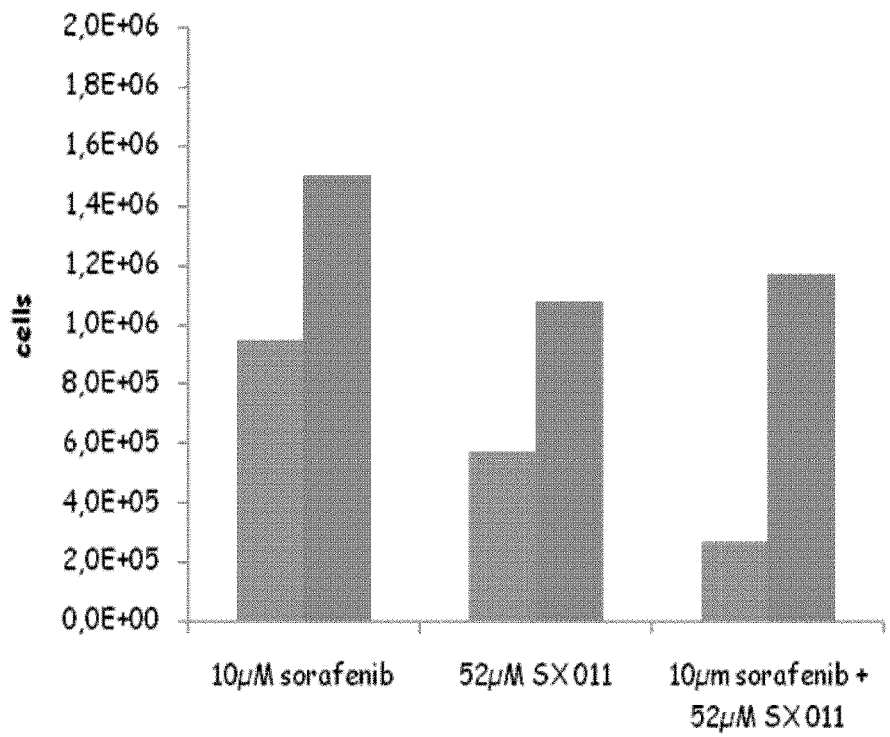
Figure 17:
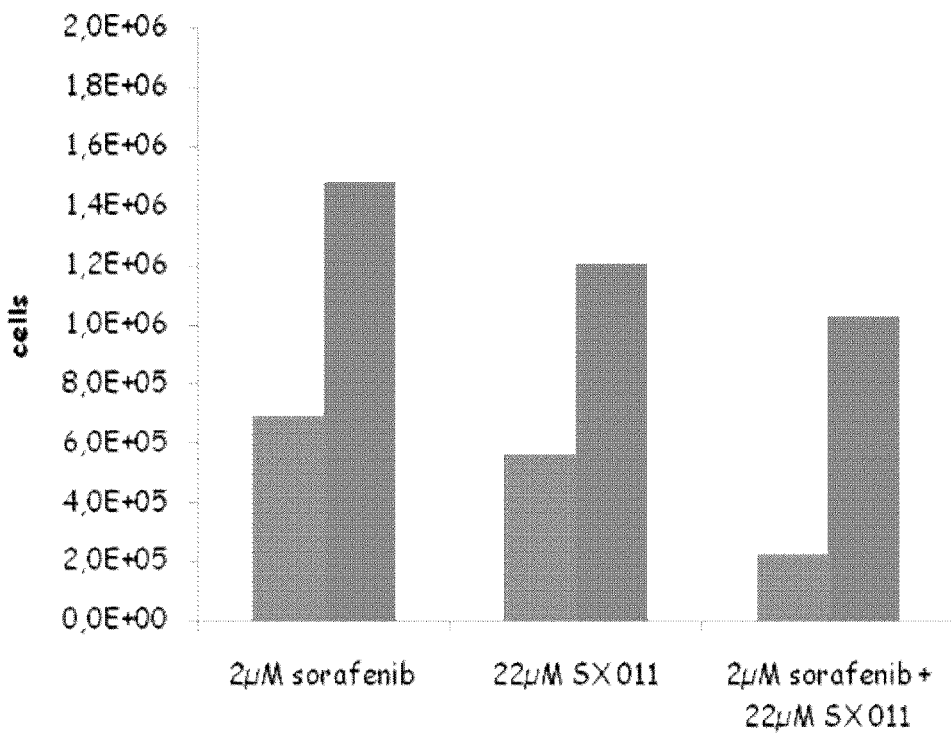

FIG. 8 shows the number of cells (as an indicator of proliferative activity) in an in vitro assay in which murine liver cancer cells were treated with Sorafenib in combination with the Mapk14 inhibitor BIRB-796, FIG. 9 shows the number of cells (as an indicator of proliferative activity) in an in vitro assay, in which a human liver cancer cell line was treated with Sorafenib in combination with the inhibitor of Mapk14 BIRB-796, FIG. 10 shows a picture of cell staining (cell density as an indicator of proliferative activity) (crystal violet assay) of a human liver cancer cell line after treatment of Sorafenib in combination with the Mapk14-specific inhibitor BIRB-796, FIG. 11 shows the quantification of the number of dead cells (human liver cancer cell line) after treatment with Sorafenib in combination with the Mapk14-specific inhibitor BIRB-796 and controls, respectively, FIG. 12 shows the number of cells in an in vitro assay in which a murine hepatocyte cancer cell line was treated with Sorafenib in combination with the Mapk14 inhibitor SB202190, FIG. 13 shows the number of cells in an in vitro assay, in which a human liver cancer cell line was treated with Sorafenib in combination with the inhibitor of Mapk14 SB202190, FIG. 14 shows a picture of cell staining (cell density as a marker for proliferative activity) of a human liver cancer cell line after treatment of Sorafenib in combination with the Mapk14-specific inhibitor SB202190, FIG. 15 shows the quantification of the number of dead cells (human liver cancer cell line) after treatment with Sorafenib in combination with the Mapk14-specific inhibitor SB202190 and controls, respectively, FIG. 16 shows the number of cells in an in vitro assay in which a murine liver cancer cell line was treated with Sorafenib in combination with the Mapk14 inhibitor SX011, and FIG. 17 shows the number of cells in an in vitro assay, in which a human liver cancer cell line was treated with Sorafenib in combination with the inhibitor of Mapk14 SX011.

EXAMPLE 1

Treatment of Liver Cancer In Vivo

As a representative of a human patient having liver cancer, a genetically manipulated mouse model (p19$^{Arf-/-}$) was generated, in which liver cancers were induced by a constitutive expression of the oncogenic NrasG12V mutant.

The nucleic acid construct for generating liver carcinomas is schematically shown in FIG. 1, containing an expression cassette, wherein the coding sequence for NrasG12V is arranged between a 5' promoter sequence and a 3' polyadenylation site, which expression cassette is flanked by two inverted repeat elements (IR). For intrahepatic delivery of the expression cassette, this nucleic acid construct was administered in combination with a nucleic acid construct containing an expression cassette for the transposase sleeping beauty 13 (SB 13) under the control of the constitutive phosphoglycerate kinase promoter (PGK). The mouse model receiving both nucleic acid constructs shown in FIG. 1 was p19$^{Arf-/-}$, providing the genetic background sufficient for constitutive generation of murine liver cancer. Nucleic acid constructs were introduced into experimental mice using hydrodynamic tail vein injection.

Mice that were genetically conditioned to develop liver cancer were treated with a pharmaceutical composition containing Sorafenib in a carrier, and carrier alone as a control.

The expression cassette in addition to the coding sequence for Nras12V contains the coding sequence for a short hairpin RNA as an example for an siRNA/shRNA. As an shRNA, a non-specific shRNA (shcontrol) was used, an shRNA specific for the murine mRNA encoding murine Mapk14 (shMapk14.1095), and an alternative shRNA specific for the murine mRNA encoding Mapk14 (shMapk14.2590). For each mouse model having one of the nucleic acid constructs, mice were mock-treated with carrier, or with Sorafenib alone.

The survival curves are shown in FIG. 2. A liver cancer patient without a Mapk14 inhibitor is represented by the non-specific shRNA (1, shcontrol+carrier) and with the known treatment of Sorafenib (2, shcontrol+Sorafenib) according to the mouse model has an increased survival rate, whereas both mouse models in which the Mapk14 activity is inhibited by the shRNA specific for the mRNA encoding Mapk14 in combination with Sorafenib (4, shMapk14.1095+Sorafenib, and 6, shMapk14.2590+Sorafenib) have a significantly increased survival rate. In contrast, the inactivation of Mapk14 alone by an shRNA, i.e. without treatment by administration of Sorafenib (3, shMapk14.1095+carrier and 5, shMapk14.2590+carrier) have a survival rate essentially corresponding to the survival rate of mouse models without inactivation of Mapk14 (1, 3, 5).

FIG. 3 shows the levels of mRNA encoding Mapk14 in relation (%) to the non-specific control shRNA (shcontrol). It can be seen that the expression of each of shMapk14.1095 (SEQ ID NO: 1370) and shMapk14.2590 (SEQ ID NO: 1371) and of shMapk14.2364, which hybridize to the mRNA encoding Mapk14 results in a reduction of the mRNA encoding Mapk14 in the liver tissue.

FIG. 4 shows Western blot analyses of murine liver cancer cells with specific detection of Mapk14 and α-tubulin as a loading control. This analysis shows that the expression level of Mapk14 is significantly reduced by expression of shRNA specific for the mRNA encoding Mapk14, exemplified by shMapk14.1095, shMapk14.2590, and shMapk14.2364, whereas there is a drastically higher level of Mapk14 expression in the presence of shRNA (shcontrol) expression.

FIG. 5 shows photographs of livers explanted from the mouse model and the respective GFP—imaging of explanted mouse livers, confirming visually that in mouse models receiving no Sorafenib (top row, FIGS. 5.1, 5.2, 5.5, 5.6, 5.9, and 5.10) (carrier), the expression of a non-specific shRNA (shcontrol, FIGS. 5.1, 5.2) or of an shRNA inactivating Mapk14 (shMapk14.1095, shMapk14.2590, FIGS. 5.5, 5.6, 5.9, and 5.10) essentially do not reduce the development of liver cancer.

In a further experiment it was observed that in further control mice which did not express an shRNA, a similar tumor development and a similar survival rate was found as for the mice expressing the non-specific shRNA (shcontrol).

The lower row of pictures of FIG. 5 (FIGS. 5.3, 5.4, 5.7, 5.8, 5.11, and 5.12) shows that the inactivation of Mapk14, in this assay obtained in vivo by expression of an shRNA specific for the mRNA encoding Mapk14 (5.7, 5.8, 5.11, and 5.12) in the presence of treatment with Sorafenib drastically reduces the occurrence of liver cancer both in relation to the treatment with Sorafenib alone (FIGS. 5.3 and 5.4) and in relation to expression of an inhibitory shRNA alone (FIGS. 5.5, 5.6, 5.9, and 5.10).

The GFP imaging correlates with expression of NrasG12V positive tumors. Decreased GFP activity is observed for shRNAs shMapk14.1095 and shMapk14.2590 in the presence of Sorafenib, indicating reduction of cancer cells that were induced by the expression of Nras.

EXAMPLE 2

Treatment of Liver Cancer

Again, mouse models were used for representing human liver cancer patients in treatment using Sorafenib in combination with an agent inhibiting the activity of Mapk14. As an example for a pharmaceutical agent for the inactivation of the activity of Mapk14, an shRNA (shMapk14.1095) specific for the murine mRNA encoding Mapk14 was used. The shRNA was provided by controlled expression using an expression cassette which is under the control of a tetracycline response element (TRE) of the otherwise constitutive viral promoter ($P_{minCMV}$). The expression cassette contains the coding sequence for a shRNA molecule and the coding sequence of a GFP marker gene. The nucleic acid construct containing the expression cassette for the shRNA molecule and the coding sequence of a GFP marker gene under the control of the Tet-inducible promoter also contains a constitutive expression cassette for rtTA (rtetRVP16), which in the presence of Doxycycline (DOX) binds to the TRE and activates the promoter of the expression cassette encoding a fusion of shRNA and GFP.

FIG. 6 schematically shows the nucleic acid constructs and the mechanism for inducing transcription of shRNA and GFP encoding sequence.

Generally, the nucleic acid construct of FIG. 6 is introduced into experimental mice via retroviral infection of cancer cells which after selection are injected into the liver of wildtype mice. The injected mice then develop liver carcinomas in which Mapk14 can be conditionally inactivated by inducing transcription of the shRNA by addition of DOX.

FIG. 7 shows the result of an experiment using the expression of an shRNA specific for the mRNA encoding murine Mapk14, namely shMapk14.1095, or a non-specific shRNA (shcontrol). The administration of DOX induces inactivation of Mapk14 by inducing transcription of the shRNA and GFP. The administration of DOX in combination with Sorafenib significantly increased survival rates (10, shMapk14.1095+DOX+Sorafenib), whereas in the absence of the inactivation of Mapk14, represented by the lack of induction of shMapk14 in the absence of DOX (14, shMapk14.1095−DOX+Sorafenib) or in the presence of a non-specific shRNA (12, shcontrol+DOX+Sorafenib) showed a lower survival rate as expected for treatment by Sorafenib alone. For control, the absence of a specific inhibitory shRNA and without Sorafenib (15, shMapk14.1095−DOX−Sorafenib), in the absence of non-specific shRNA and without Sorafenib (13, shcontrol−DOX−Sorafenib), and with presence of Mapk14 specific shRNA without Sorafenib but carrier (11, shMapk14.1095+DOX+carrier) were tested.

EXAMPLE 3

Inactivation of Mapk14 by a Specific Kinase Inhibitor Increases the Efficacy of Sorafenib Against Liver Cancer Cell Lines As an example for a medicament containing Sorafenib in combination with an inhibitor specific for Mapk14 kinase, BIRB-796, SB 202190 and SX 001 were tested in an in vitro assay. These in vitro experiments show the increased efficacy of Sorafenib when administered in combination with an inhibitor of Mapk14 kinase protein on the example of cultivated murine and human liver cancer cell lines.

In the assay, murine liver cancer cells (Nras arf−/−) were cultivated. Cultivated cells were treated with 10 µM Sorafenib, 2 µM BIRB, 12 µM BIRB and with a combination of 10 µM Sorafenib+2 µM BIRB, or a combination of 10 µM Sorafenib+12 µM BIRB. For each of these assays, a parallel assay was made, replacing Sorafenib or Mapk14 inhibitors by formulation agents without pharmaceutical active agent (carrier).

FIG. 8 shows the results of the viable cell count after two days of treatment of the murine cancer cells and FIG. 9 shows the viable cell count after 7 days of treatment of the cultivated human liver cancer cell line (Hep3B) with the combinations of 2 µM Sorafenib, 2 µM BIRB, 12 µM BIRB, a combination of 2 µM Sorafenib+2 µM BIRB, or a combination of 2 µM Sorafenib+12 µM BIRB, respectively, in the left columns, whereas samples without pharmaceutical active agent (carrier) are shown as right hand columns. These results show that the activity of Sorafenib against liver cancer cells can be reproduced in vitro with cultivated murine and human liver cancer cells, respectively. In detail, the presence of 10 µM or 2 µM Sorafenib as the only pharmaceutical active agent shows a decrease of viable cancer cells after two and seven days, respectively, whereas in murine cells, the inhibitor BIRB-796 only has no significant influence on cultivated murine liver cancer cells, whereas BIRB-796 alone shows a reduction of viable human cancer cells. In murine liver cancer cells, and even more pronounced in human liver cancer cells, the combination of Sorafenib with the inhibitor BIRB-796 shows a marked increase in the efficacy over Sorafenib alone, and the combination of 12 µM BIRB-796 with 2 µM Sorafenib results in a significant decrease in viable cancer cells compared to the reduction of cancer cells by Sorafenib alone.

FIG. 10 shows crystal violet staining of cultivated human liver cancer cells which are cultivated and treated for 7 days with 2 µM Sorafenib, 12 µM BIRB-796, or a combination of 2 µM Sorafenib+12 µM BIRB-796 (upper row), controls without kinase inhibitor are shown in the lower row (carrier). This view of the culture plates makes it evident that the combination of Sorafenib with an inhibitor for Mapk14, represented by BIRB-796, increases the efficacy of Sorafenib.

The dead cell count of FIG. 11, using trypane blue staining of the cultivated human liver cancer cells (Hep3B) shows that the increase in dead cells in the presence of an inhibitor (left hand columns) was more prominent for the combination of Sorafenib with BIRB-796 over Sorafenib or BIRB-796 alone, and over the control (carrier, right hand columns) without a kinase inhibitor.

Similar to the assay for BIRB-796, SB 202190 was tested in an in vitro assay of the murine liver cancer cells (Nras Arf−/−) and the human liver cancer cell line (Hep3B).

FIG. 12 shows the results of the viable cell count after two days of treatment of the murine cancer cells and FIG. 13 shows the viable cell count after 7 days of treatment of the cultivated human liver cancer cell line (Hep3B) with the combinations of 2 µM Sorafenib, 2 µM SB202190, 12 µM SB202190, a combination of 2 µM Sorafenib+2 µM SB202190, or a combination of 2 µM Sorafenib+12 µM SB202190, respectively, in the left columns, whereas samples without pharmaceutical active agent (carrier) are shown as right hand columns.

These results confirm that the activity of Sorafenib against liver cancer cells can be reproduced in vitro with cultivated murine and human cancer cell lines respectively. Further, in murine cancer cells, and even more pronounced in human cancer cells, the combination of Sorafenib with the inhibitor SB202190 shows a marked increase in the efficacy over Sorafenib alone, and the combination of 12 µM SB202190 with 2 µM Sorafenib results in a significant decrease in viable cancer cells compared to the reduction of cancer cells by Sorafenib alone.

FIG. 14 shows the crystal violet staining of cultivated human liver cancer cells which are cultivated and treated for 7 days with 2 µM Sorafenib, 12 µM SB202190, or a combination of 2 µM Sorafenib+12 µM SB202190 (upper row), controls without kinase inhibitor are shown in the lower row (carrier). This view of the culture plates makes it evident that the combination of Sorafenib with an inhibitor for Mapk14, represented by SB202190, increases the efficacy of Sorafenib.

The dead cell count shown in FIG. 15 (left hand columns indicate counts in presence of inhibitor, right hand columns are control with carrier only) supports the finding that the combination of the Mapk14 inhibitor SB202190 with Sorafenib is significantly more effective than Sorafenib or SB202190 alone.

FIG. 16 shows the results of the viable cell counts after two days of treatment of the murine cancer cells, and FIG. 17 shows the viable cell count after 7 days of treatment of the cultivated human liver cancer cell line (Hep3B) with the combinations of 10 µM or 2 µM Sorafenib, 52 µM or 22 µM SX 011, and a combination of 10 or 2 µM Sorafenib+52 or 22 µM SX 011 respectively, in the left hand columns, whereas samples without pharmaceutical active agent (carrier) are shown as right hand columns.

These results confirm that the activity of Sorafenib against liver cancer cells can be reproduced in vitro with cultivated murine and human liver cancer cells, respectively. Further, in murine cancer cells, and even more pronounced in human cancer cells, the combination of Sorafenib with the inhibitor SX 011 shows a marked increase in the efficacy over Sorafenib alone, and the combination of SX 011 with Sorafenib results in a significant decrease in viable cancer cells compared to the reduction of cancer cells by Sorafenib alone.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10441577B2). An electronic copy of the "Sequence Listing" will also be available from the USPTO upon request and payment of the fee set forth in 37 CFR 1.19(b)(3).

The invention claimed is:

1. A pharmaceutical composition comprising Sorafenib and an inhibitor of the activity of Mapk14 for use as a medicament in the treatment or prevention of liver cancer, wherein the inhibitor is selected from the group consisting of Skepinone,

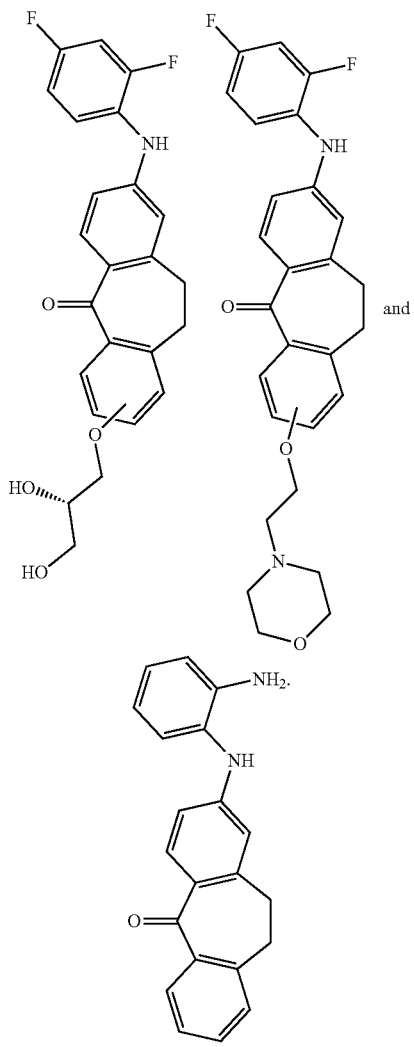

2. The pharmaceutical composition according to claim 1, wherein the inhibitor has an IC50 for Mapk14 of at maximum 30 nM.

3. The pharmaceutical composition according to claim 1, wherein Sorafenib is contained in a formulation for administration separate from a formulation containing the inhibitor of the activity of Mapk14.

4. The pharmaceutical composition according to claim 1, wherein Sorafenib and the inhibitor of the activity of Mapk14 are contained in one composition.

5. A pharmaceutical combination for the treatment of or prevention of liver cancer comprising: a pharmaceutical formulation comprising an inhibitor of the activity of Mapk14 and a separate pharmaceutical formulation comprising Sorafenib, wherein the inhibitor is selected from the group consisting of Skepinone,

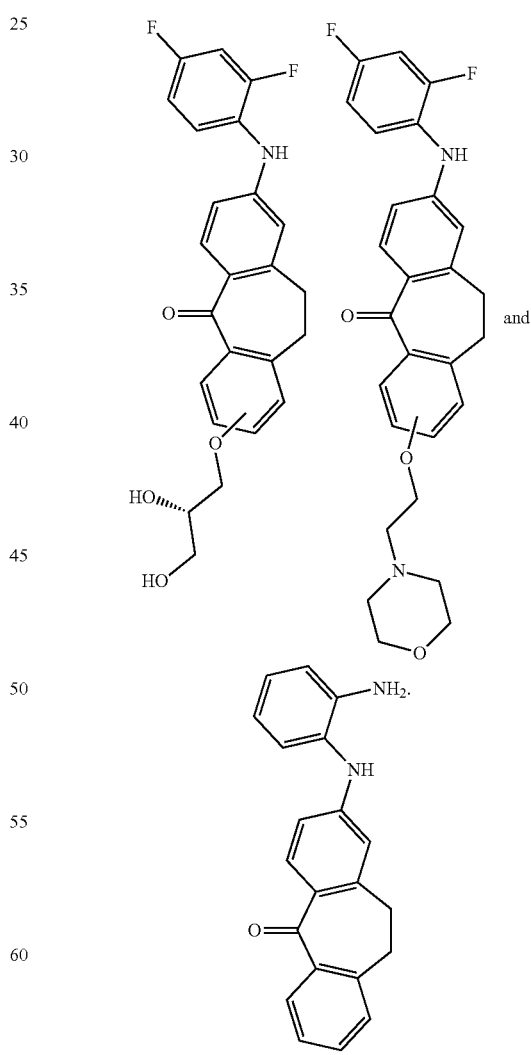

6. The pharmaceutical combination according to claim 5, wherein the pharmaceutical formulation comprising an inhibitor of the activity of Mapk14 is for administration separate from the administration of the pharmaceutical formulation comprising Sorafenib for the treatment or prevention of liver cancer for administration to a patient, wherein the inhibitor is selected from the group consisting of Skepinone,

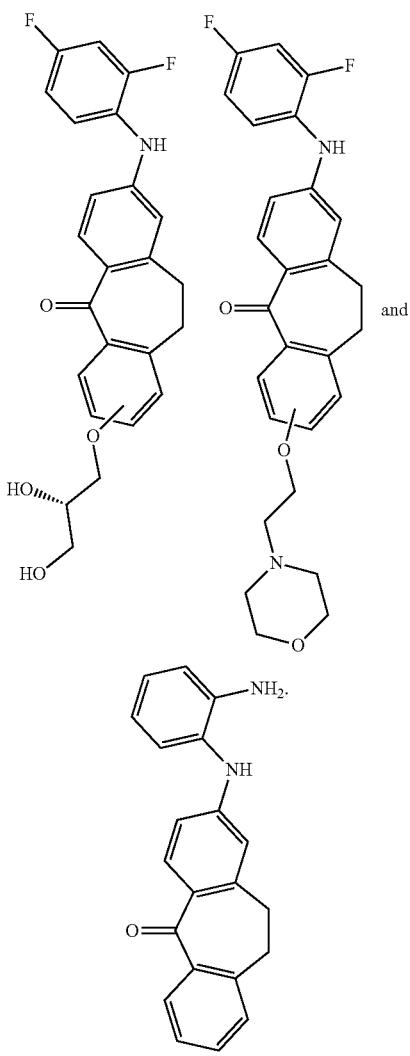

7. A method for treatment or prevention of liver cancer comprising administration of an inhibitor of the activity of Mapk14 in combination with Sorafenib, wherein the inhibitor is selected from the group consisting of Skepinone,

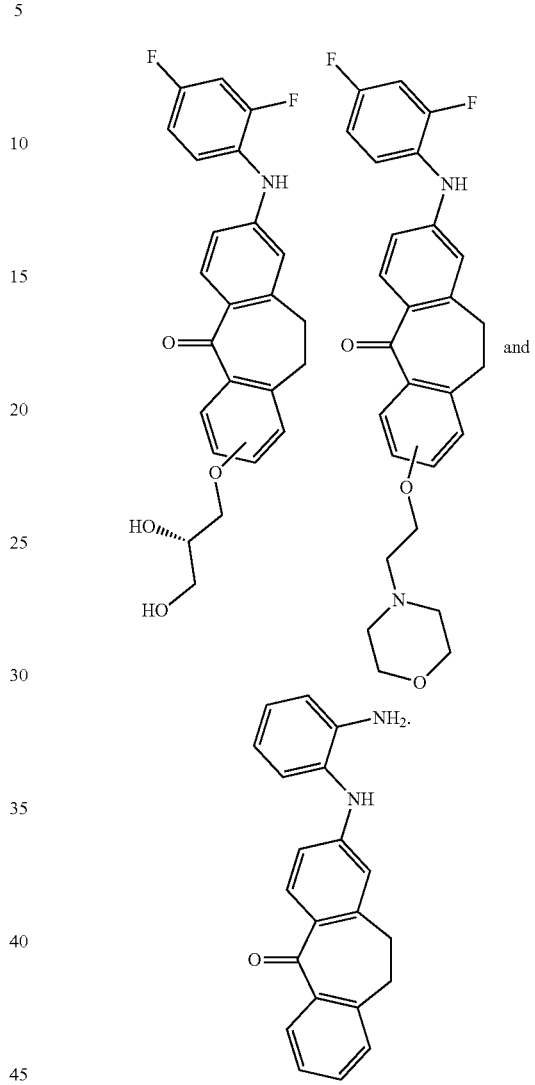

* * * * *